(12) United States Patent
Guichard et al.

(10) Patent No.: US 7,122,193 B1
(45) Date of Patent: Oct. 17, 2006

(54) RETRO PEPTIDES, ANTIBODIES THERETO AND THEIR USES FOR VACCINATION AND IN VITRO DIAGNOSIS

(75) Inventors: Gilles Guichard, Strasbourg (FR); Slyviane Muller, Strasbourg (FR); Jean-Paul Briand, Strasbourg (FR); Marc Regenmortel, Strasbourg (FR)

(73) Assignee: Biomerieux S.A., Marcy-L'Etoile (FR)

( * ) Notice: Subject to any disclaimer, the term of this patent is extended or adjusted under 35 U.S.C. 154(b) by 0 days.

(21) Appl. No.: 09/549,186

(22) Filed: Apr. 13, 2000

Related U.S. Application Data

(63) Continuation-in-part of application No. 08/716,249, filed as application No. PCT/FR95/00292 on Mar. 13, 1995, now Pat. No. 6,455,244.

(30) Foreign Application Priority Data

Mar. 13, 1994 (FR) .................................. 94 02950

(51) Int. Cl.
*A61K 39/125* (2006.01)
(52) U.S. Cl. ............................. 424/216.1; 424/186.1; 530/326
(58) Field of Classification Search ................ 530/300, 530/326; 424/216.1, 186.1
See application file for complete search history.

(56) References Cited

U.S. PATENT DOCUMENTS

| 5,519,115 A | 5/1996 | Mapelli et al. |
| 5,763,408 A | 6/1998 | Nishikawa |
| 5,789,382 A | 8/1998 | Wellstein |
| 6,455,244 B1 | 9/2002 | Guichard et al. |

OTHER PUBLICATIONS

Benkirane, N., et al., 1993, "Antigenicity and immunogenicity of modified synthetic peptides containing D-amino . . . ", J. Biol. Chem. 268(35):26279-26285 (abstract provided).*
Herve, M., et al., 1997, "On the immunogenic properties of retro-inverso peptides . . . ", Mol. Immunol. 34(2):157-163 (abstract provided).*
Muller et al., Peptide Research, vol. 8, No. 3 (1995) pp 138-144.
Briand et al., PNAS, vol. 94, pp. 12545-12550, Nov. 1997.
Meziere et al., The Journal of Immunology 1997, 159: 3230-3237.
Briand et al., JBC, vol. 270, No. 35, Sep. 1995, pp 20686-20691.
Jameson et al., Nature, vol. 368, Apr. 21, 1994, pp 744-746.
Verdoliva et al., JBC, 270, 1995, pp 30422-30427.
Roubi, Jul. 14, 1997, C&EN, 56-57.
McDonnell et al., JACS, 1997, 119, 5321-5328.
Chorer et al., TIBTECH (1995) vol. 13, pp 438-445.
Rule 132 Declaration of Sylviane Muller and Jean-Paul Briand executed Mar. 27, 1999 and Mar. 28, 1999, respectively.
Nargi et al, Vaccine 17 (1999), pp 2888-2893.

\* cited by examiner

*Primary Examiner*—J S Parkin
(74) *Attorney, Agent, or Firm*—Nixon & Vanderhye P.C.

(57) ABSTRACT

The present invention relates to retro peptides, as well as antibodies thereto, and to their uses, chiefly in the field of preparation of pharmaceutical compositions, in particular vaccines, and for in vitro diagnosis of various pathologies.

14 Claims, 20 Drawing Sheets

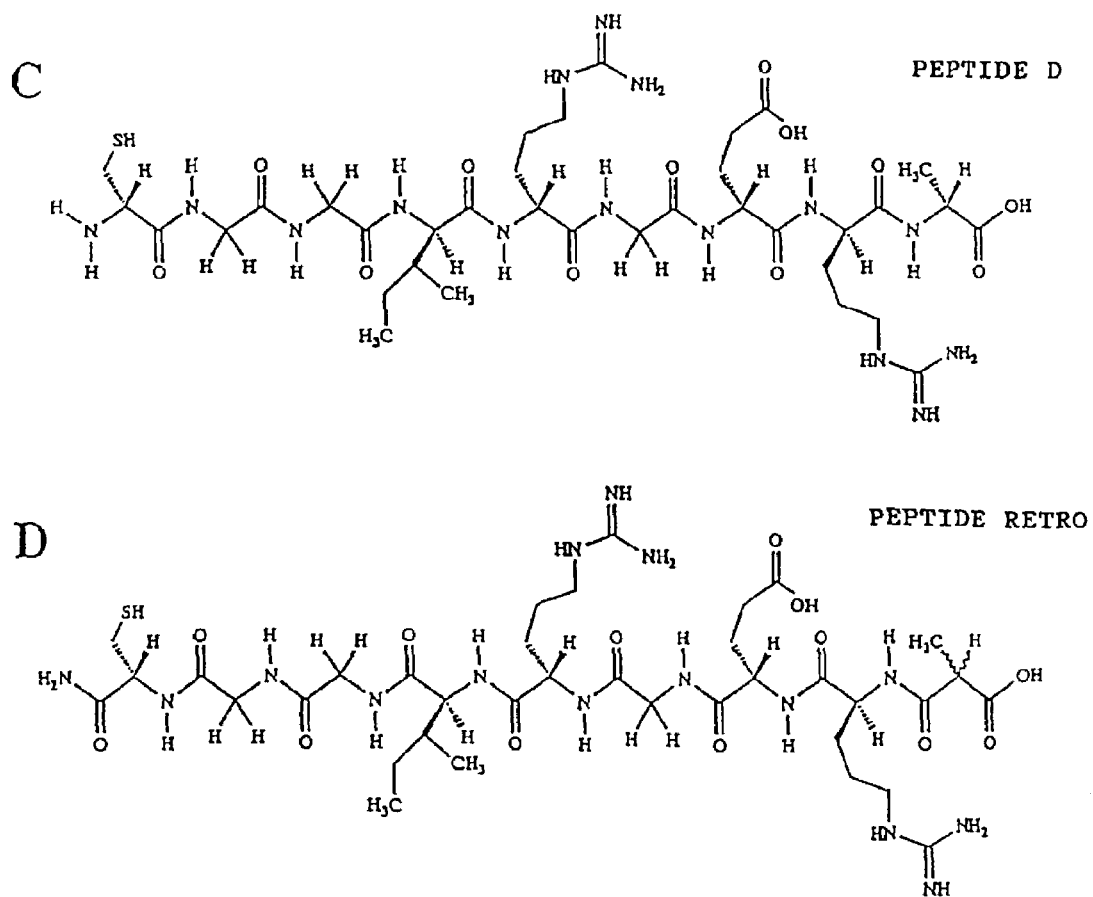
Figure 1 suite a : BOP, HOBT, DIEA /DMF; b : IBTFA, CH3CN/H2O (1:1) ; c : TFA; d : NaOH (1N)/MeOH ;
e : H2, Pd/C.

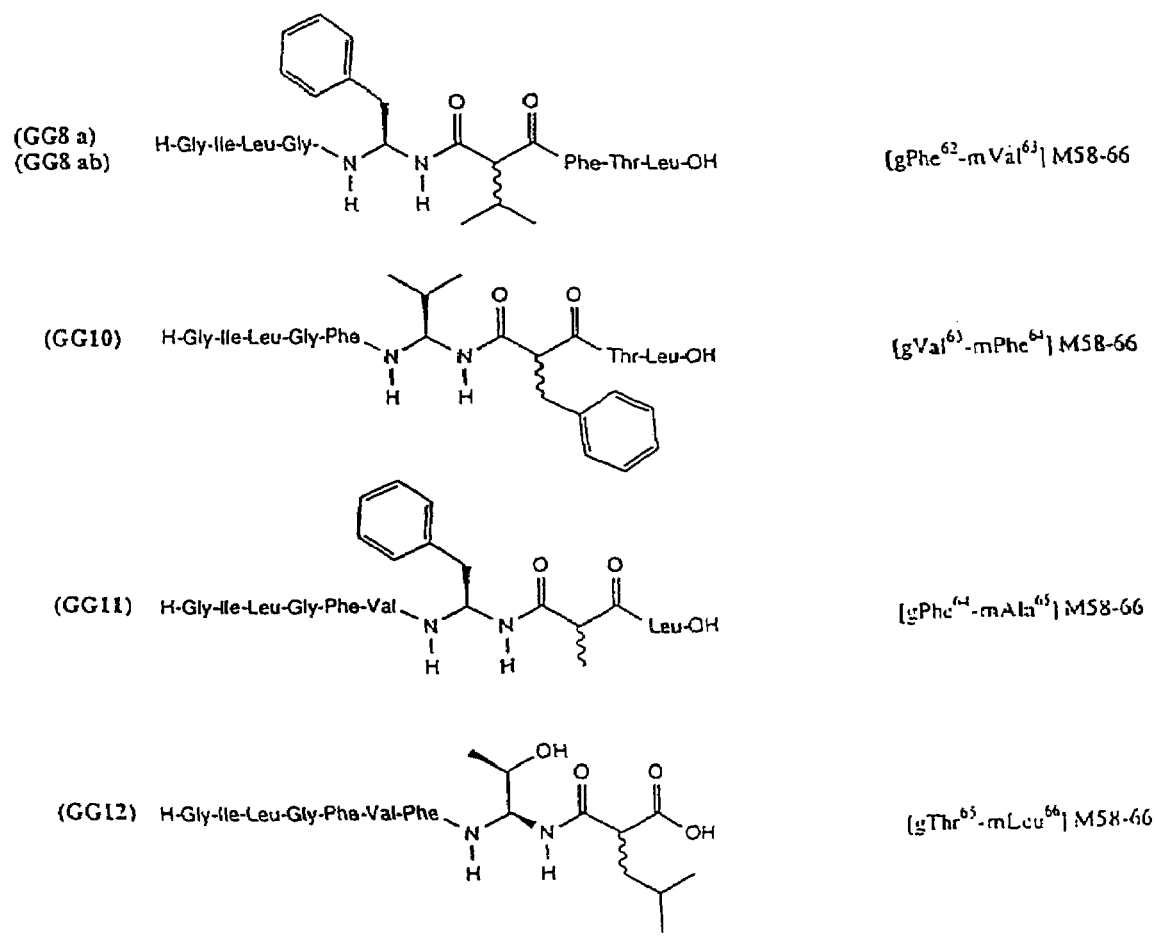
Figure 10 suite

SEQUENCE LISTING

```
<160> NUMBER OF SEQ ID NOS: 20

<210> SEQ ID NO 1
<211> LENGTH: 19
<212> TYPE: PRT
<213> ORGANISM: protein VP1 of aphthous fever virus

<400> SEQUENCE: 1

Cys Gly Ser Gly Val Arg Gly Asp Ser Gly Ser Ala Leu Arg Val Ala
 1               5                  10                  15

Arg Gln Leu

<210> SEQ ID NO 2
<211> LENGTH: 19
<212> TYPE: PRT
<213> ORGANISM: FMDV

<400> SEQUENCE: 2

Cys Gly Ser Gly Val Arg Gly Asp Phe Gly Ser Ala Pro Arg Val Ala
 1               5                  10                  15

Arg Gln Leu

<210> SEQ ID NO 3
<211> LENGTH: 9
<212> TYPE: PRT
<213> ORGANISM: influenza virus

<400> SEQUENCE: 3

Gly Ile Leu Gly Phe Val Phe Thr Leu
 1               5

<210> SEQ ID NO 4
<211> LENGTH: 15
<212> TYPE: PRT
<213> ORGANISM: tetanus toxin

<400> SEQUENCE: 4

Gln Tyr Ile Lys Ala Asn Ser Lys Phe Ile Gly Ile Thr Glu Leu
 1               5                  10                  15

<210> SEQ ID NO 5
<211> LENGTH: 9
<212> TYPE: PRT
<213> ORGANISM: human

<400> SEQUENCE: 5

Cys Gly Gly Ile Arg Gly Glu Arg Ala
 1               5

<210> SEQ ID NO 6
<211> LENGTH: 9
<212> TYPE: PRT
<213> ORGANISM: influenza virus

<400> SEQUENCE: 6

Gly Ile Leu Gly Phe Val Phe Thr Leu
```

<210> SEQ ID NO 7
<211> LENGTH: 20
<212> TYPE: PRT
<213> ORGANISM: FMDV

<400> SEQUENCE: 7

Cys Gly Ser Gly Val Arg Gly Asp Phe Gly Ser Leu Ala Pro Arg Val
1               5                   10                  15
Ala Arg Gln Leu
            20

<210> SEQ ID NO 8
<211> LENGTH: 20
<212> TYPE: PRT
<213> ORGANISM: FMDV

<400> SEQUENCE: 8

Cys Gly Ser Gly Val Arg Gly Asp Phe Gly Ser Leu Ala Leu Arg Val
1               5                   10                  15
Ala Arg Gln Leu
            20

<210> SEQ ID NO 9
<211> LENGTH: 20
<212> TYPE: PRT
<213> ORGANISM: FMDV

<400> SEQUENCE: 9

Cys Gly Ser Gly Val Arg Gly Asp Ser Gly Ser Leu Ala Leu Arg Val
1               5                   10                  15
Ala Arg Gln Leu
            20

<210> SEQ ID NO 10
<211> LENGTH: 15
<212> TYPE: PRT
<213> ORGANISM: human
<220> FEATURE:
<221> NAME/KEY: SITE
<222> LOCATION: (5)
<223> OTHER INFORMATION: Xaa is Nle

<400> SEQUENCE: 10

Gly Leu Lys Lys Xaa Leu Arg Thr Cys Ala Val His Ile Thr Leu
1               5                   10                  15

<210> SEQ ID NO 11
<211> LENGTH: 21
<212> TYPE: PRT
<213> ORGANISM: human

<400> SEQUENCE: 11

Val Cys Glu Lys Leu Cys Asn Glu Lys Leu Leu Lys Lys Ala Arg Ile
1               5                   10                  15
His Pro Phe His Ile
            20

<210> SEQ ID NO 12
<211> LENGTH: 18
<212> TYPE: PRT
<213> ORGANISM: human

-continued

```
<400> SEQUENCE: 12

Ser Ala Pro Ala Thr Gly Gly Val Lys Lys Pro His Arg Tyr Arg Pro
1               5                   10                  15

Gly Thr

<210> SEQ ID NO 13
<211> LENGTH: 13
<212> TYPE: PRT
<213> ORGANISM: influenza virus

<400> SEQUENCE: 13

Ser Lys Arg Gly Pro Gly Ser Asp Phe Asp Gly Gly Cys
1               5                   10

<210> SEQ ID NO 14
<211> LENGTH: 18
<212> TYPE: PRT
<213> ORGANISM: influenza virus

<400> SEQUENCE: 14

Cys Lys Ala Phe Ser Asn Ser Tyr Pro Tyr Asp Val Pro Asp Tyr Ala
1               5                   10                  15

Ser Leu

<210> SEQ ID NO 15
<211> LENGTH: 15
<212> TYPE: PRT
<213> ORGANISM: Schistosoma mansoni

<400> SEQUENCE: 15

Cys Gly Phe Thr Thr Asn Glu Glu Arg Tyr Asn Val Phe Ala Glu
1               5                   10                  15

<210> SEQ ID NO 16
<211> LENGTH: 9
<212> TYPE: PRT
<213> ORGANISM: measles virus

<400> SEQUENCE: 16

Asn Phe Leu Arg Glu Lys Lys Gln Cys
1               5

<210> SEQ ID NO 17
<211> LENGTH: 13
<212> TYPE: PRT
<213> ORGANISM: HIV

<400> SEQUENCE: 17

Ile Trp Gly Cys Ser Gly Lys Leu Ile Cys Thr Thr Ala
1               5                   10

<210> SEQ ID NO 18
<211> LENGTH: 6
<212> TYPE: PRT
<213> ORGANISM: human histone protein H3

<400> SEQUENCE: 18

Ile Arg Gly Glu Arg Ala
1               5

<210> SEQ ID NO 19
<211> LENGTH: 9
<212> TYPE: PRT
```

-continued

```
<213> ORGANISM: influenza virus

<400> SEQUENCE: 19

Gly Leu Leu Gly Phe Val Phe Thr Leu
 1               5

<210> SEQ ID NO 20
<211> LENGTH: 9
<212> TYPE: PRT
<213> ORGANISM: influenza virus

<400> SEQUENCE: 20

Gly Ile Leu Gly Phe Val Phe Ala Leu
 1               5
```

RETRO PEPTIDES, ANTIBODIES THERETO AND THEIR USES FOR VACCINATION AND IN VITRO DIAGNOSIS

The present application is a continuation-in-part of U.S. application No. 08/716,249, now U.S. Pat. No. 6,455,244 filed Sep. 13, 1996, which is a 371 of PCT/FR95/00292, filed Mar. 13, 1995, which claims priority to FR 94 02950, filed Mar. 13, 1994, the entire content to each of which is hereby incporporated by reference.

The present invention relates to retro peptides, as well as antibodies thereto, and to their uses, chiefly in the field of preparation of pharmaceutical compositions, in particular vaccines, and for in vitro diagnosis of various pathologies.

The development of neuropeptides, peptide hormones and antibiotics based on peptides or of synthetic vaccines based on peptides faces great problems due to the high sensitivity of peptides to proteolysis, which limits, inter alia, oral and parenteral administration.

For several years, attention has been paid to the synthesis of peptide analogues in order to investigate peptides which mimic natural peptides or proteins and have an increased activity and longer biological half-life compared to the latter. For example, peptide analogues have been obtained by replacing the L amino acids of the natural peptide by the corresponding D amino acids, or by non-natural residues (for example sarcosine and β-alanine), or also by modification of peptide bonds of the natural peptide (Chorev, M. & Goodman, M. (1993), Acc. Chem. Res. 26, 266–273; Marraud et al., (1993), Biopolymers, 33, 1135–1148).

These modifications give pseudopeptides or peptides which mimic the natural peptides or proteins (also called peptidomimetics) and have a metabolic stability which is greater than that of the latter, since the majority of natural proteases cannot cleave the D amino acids and non-peptide bonds.

The major problem encountered with such pseudopeptides is that of preserving their biological activity with respect to that of the natural peptide, or of the natural protein which they are supposed to mimic.

The D form of the protease HIV-1 has recently been synthesized (De L. Milton et al., (1992), Science, 256, 1445–1448). As was to be expected, the enantiomeric protein showed a reciprocal chiral specificity such that the enzyme was incapable of cleaving the normal L substrate, but hydrolysed its D enantiomer.

In contrast, Wen and Laursen (Wen, D. & Laursen, R. A., (1993), FEBS Lett., 317, 31–34) have shown that both the D and the L form of an α-helicoidal anti-icing polypeptide bond equally well to the same substrate of achiral ice, while Wade et al. (Wade et al., (1990), Proc. Natl. Acad. Sci., USA, 87, 4761–4765) found that the L and D enantiomers of several antibiotics which form channels were all as active as one another.

The modified peptides could be used as potential synthetic vaccines if they could induce the formation of antibodies which recognize the non-modified antigenic structures of the corresponding pathogen and neutralize its infectious character.

However, in comparison with the considerable work carried out to date in the field of production of antibodies to natural proteins or to synthetic peptides derived from the latter, and the study of cross-reactions between such antibodies and these natural proteins or peptides, little is known of the immune response to peptide analogues, in particular to the D peptides and the peptides containing modified bonds.

Several authors have asserted that pseudopeptides probably have very little or no immunogenicity, since they could not be transformed and presented to molecules of major histocompatibility complex (MHC) in order to be recognized by auxiliary T cells or by cytotoxic T lymphocytes. Consequently, Dintzis et al. Proteins: Structure, Function and Genetics (1993) 16, 306–308, have recently reported that the L enantiomer of rubrexodin induces a strong immune response by producing immunoglobulins of the G isotype (IgG), while the corresponding protein made up of amino acids all with the D configuration does not induce an immune response.

DESCRIPTION OF THE INVENTION

The object of the present invention is to provide pharmaceutical compositions, and more particularly vaccines, comprising peptide analogues which have a half-life which is clearly superior to that of natural proteins or that of synthetic peptides which are or are not derived from these natural proteins (these natural proteins, or peptides which are or are not derived from the latter, also being referred to in the following by the expression "parent proteins or peptides"), of which they are the analogues, while having a comparable, or even higher, biological, and more particularly immunological, activity to that of the abovementioned parent proteins or peptides.

The object of the present invention is also to provide methods for in vitro diagnosis of diseases associated with the presence in the organism of an individual of endogenous or exogenous proteins, these methods being carried out with the aid of peptide analogues as defined above and having the advantage of being more efficient than the current methods of diagnosis carried out with the aid of the parent peptides or proteins. The object of the present invention is thus, in particular, to provide new kits for implementing such methods of diagnosis.

The present invention chiefly relates to the use of compounds of the peptide type (also called peptide analogues, or pseudopeptides, or peptidomimetics), in which at least one of the —CO—NH— bonds, and advantageously all the —CO—NH— bonds, of the peptide chain of the corresponding parent peptide (containing no —NH—CO— bond in its peptide chain) is (are) replaced by (a) —NH—CO— bond(s), the chirality of each aminoacyl residue, whether involved or not in one or more of the abovementioned —NH—CO— bonds, being either maintained or reversed with respect to the corresponding aminoacyl residues which make up the said parent peptide, these compounds of the peptide type also being called immunoretroids, or antibodies to the said immunoretroids (anti-immunoretroid antibodies), the said immunoretroids being capable of forming a complex with the said anti-immunoretroid antibodies as well as with antibodies to the parent peptides or proteins (called anti-parent antibodies), and/or to the enantiomers of these parent peptides or proteins, for the preparation:

of a medicament intended for prevention or treatment of diseases associated with the presence in the organism of an individual of an exogenous or endogenous protein capable of being recognized by the abovementioned anti-immunoretroid or anti-parent antibodies, or of a medicament intended for prevention or treatment of diseases involving molecules of major histocompatibility complex and/or T cell receptors, of a medicament intended for prevention or treatment of diseases associated with the presence in the organism of an individual of an antibody to an endogenous or exogenous protein capable of being recognized by a said immunoretroid, or for implementation of a method of in vitro diagnosis of the abovementioned diseases.

As has already been seen above, the abovementioned term "parent peptide" is to be understood as meaning a peptide which exists as such in the natural state, in particular in a microorganism or in a higher organism (in particular in the human organism), or any peptide of immunological interest obtained by peptide synthesis, or a peptide derived from a protein such as exists in the natural state in the abovementioned organisms, in particular by fragmentation of the said protein (in particular with the aid of suitable proteases, followed by purification of the peptide in question), or by peptide synthesis (by the methods conventionally used in this field)

or a peptide derived from a protein such as exists in the natural state but of which the immunological activity has been modified, maintained or optimized by replacing certain amino acids of the natural sequence, for example following screening of a library of analogous peptides obtained by peptide synthesis.

It goes without saying that the —CO—NH— and —NH—CO— bonds should be considered in the above and the following, in the direction of the parent peptide chain from the amino-terminal (N-terminal) end towards the carboxy-terminal (C-terminal) end.

The immunoretroids used in the invention can be linear or cyclic or branched.

The immunoretroids used in the context of the present invention are compounds made up of a peptide chain in which at least one of the residues, this residue being, as appropriate, of opposite chirality to that of the aminoacyl radical corresponding to it in the peptide chain of the parent peptide, is bonded to at least one of its neighbouring residues by an —NH—CO— bond, the said peptide chain containing, as appropriate, one or more aminoacyls of opposite chirality to that of the aminoacyl residue corresponding to it in the peptide chain of the parent peptide, it being possible for the amino- and carboxy-terminal ends, independently of one another, to be either identical to the N- and C-terminal ends of the corresponding parent peptide or different from these latter ends.

A residue is understood as meaning a group of the formula —X—CH(R)—Y—, in which X and Y are identical to or different from one another and are chosen from —NH— or —CO—. Hence either an aminoacyl residue or an aminoacyl derivative in which the terminal ends are not those of an aminoacyl residue are thus called residues.

By way of illustration, the immunoretroids used in the context of the present invention are those derived from parent peptides which correspond to the following formula (I):

X-AA1-(AA2 - - - AAn-1)$_i$-AAn-Y  (I)

in which:

AA1 represents an aminoacyl residue, which may be deaminated and in which the amine function in the α-position, if this exists, can be protected by a grouping X, X representing P—, R— or RCO—, i=0 or 1, n represents 2 if i=0, and n represents an integer from 3 to 1,000, and preferably from 5 to 100, if i=1, it being understood that if n=3, the corresponding immunoretroid corresponds to the formula AA1-AA2-AA3, AAn represents an aminoacyl residue which may be decarboxylated and in which the acid function in the α-position, if this exists, is optionally protected by a grouping Y, Y being of the ester —OR or amide —NH$_2$ or —NRR' type, it being possible for the groupings R and R' to represent hydrogen atoms, alkyl radicals having 1 to 25 carbon atoms, radicals containing an allyl group and having 3 to 25 carbon atoms or radicals containing an aryl group and having 6 to 25 carbon atoms, and in particular —CH$_3$ (methyl), —CH$_2$CH$_3$ (ethyl), —CH(CH$_3$)$_2$ (isopropyl), —C(CH$_3$)$_3$ (tert-butyl), -Φ (phenyl), —CH$_2$Φ (benzyl), —CH$_2$—CH$_2$Φ (2-phenyl-ethyl), —CH$_2$CHCH$_2$ (allyl), methyl-fluorenyl, —CH$_2$CONH$_2$ (glycolamide), or —CH$_2$CONΦ$_2$ (benzhydrylglycolamide), this list not being limiting, the grouping P being of the urethane type (Boc (tert-butyloxycarbonyl), Fmoc (fluorenylmethyloxycarbonyl), Z (benzyloxycarbonyl), CH$_2$CHCH$_2$OCO— (allyloxycarbonyl) or other), and in these parent peptides of the formula (I), at least one of the bonds between two aminoacyl residues of the formula I being an —NH—CO— bond, and, as appropriate, at least one of the aminoacyl residues AA1 to AAn being of opposite chirality to that of the corresponding aminoacyl residue in the parent peptide.

In the peptides used in the context of the present invention, the —NH—CO—bonds which replace the —CO—NH— bonds of the corresponding parent peptide can be in any position in the peptide, and can replace either a —CO—NH— corresponding to a cleavage site for proteases or a —CO—NH— which does not correspond to such a site.

The —NH—CO— bonds which replace the —CO—NH— bonds are advantageously those which interact with the peptide receptor (antibody, MHC, T receptor).

According to an advantageous embodiment of the invention, the immunoretroids preferably correspond to the following formula (II):

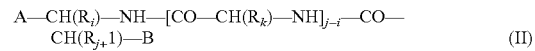

wherein n, which is the number of aminoacyl residues in formula I, is a whole number from 3–1,000, and R$_i$, R$_k$, and R$_{j+1}$ are side chains of the aminoacyl residues, i, j and k are whole numbers wherein 1≦i≦j<n, and if i=j, k=0; and if i<j, i+1≦k≦j;

such that, where i=1 and j+1=n, A is Q and B is M;

where i=1 and j+1≠n, A is Q and B is L;

where i≠1 and j+1=n, A is T and B is M; and where i≠1 and j+1≠n, A is T and B is L;

Q being selected from the group consisting of H—, H$_2$N—, P—HN—, RR'N—, H$_2$NCO—, RR'NCO—, RCO—;

M being selected from the group consisting of H—, —COOH, —COOR, —CONH$_2$, —CONRR' and —NHCOR;

L being —CO—NH—CH(R$_{j+}$2)—CO— ... —NH—CH (R$_n$)—CO—Y wherein Y is selected from the group consisting of —OH, —OR, —NH$_2$, and —NRR'; and T being X—HN—CH(R$_1$)—CO— ... —NH—CH(R$_{i-1}$)CO—NH— wherein X is selected from the group consisting of H—, P—, R— and RCO—;

wherein it being possible for the groupings R and R' to represent hydrogen atoms, alkyl radicals having 1 to 25 carbon atoms, radicals containing an allyl group and having 3 to 25 carbon atoms or radicals containing an aryl group and having 6 to 25 carbon atoms, and in particular —CH$_3$ (methyl), —CH$_2$CH$_3$ (ethyl), —CH(CH$_3$)$_2$ (isopropyl), —C(CH$_3$)$_3$ (tert-butyl), -Φ (phenyl), —CH$_2$Φ (benzyl), —CH$_2$—CH$_2$Φ (2-phenyl-ethyl), —CH$_2$CHCH$_2$ (allyl), methyl-fluorenyl, —CH$_2$CONH$_2$ (glycolamide) or —CH$_2$CONΦ$_2$ (benzhydrylglycolamide), this list not being limiting, the grouping P being a protecting group which may be of the urethane type (Boc (tert-butyloxycarbonyl), Fmoc (fluorenylmethyloxycarbonyl), Z (benzyloxycarbonyl), CH$_2$CHCH$_2$OCO— (allyloxycarbonyl) or other), the chirality of reach residue, whether involved or not in one or more —NH—CO— bonds, being either maintained or reversed with respect to the corresponding aminoacyl residues which make up the parent peptide.

It will be appreciated that:

If i=1 and j+1=n, all the bonds are —NH—CO— bonds.

If i=1 and j+1≠n, the —NH—CO— bonds are on the N-terminal side.

If i≠1 and j+1=n, the —NH—CO— bonds are on the C-terminal side.

If i≠1 and j+1≠n, the —NH—CO— bonds are on neither the N-terminal side nor the C-terminal side.

The number of —NH—CO— bonds is equal to j−i+1.

The number of —NH—CO— bonds is advantageously at least equal to 2.

The invention more particularly relates to the abovementioned use of retro-inverso peptides as immunoretroids.

Retro-inverso peptides are to be understood as meaning any peptide and peptide analogue corresponding to the definition given above for immunoretroids used in the context of the present invention, the said peptide being more particularly made up of a peptide chain in which at least one of the residues on the one hand is bonded to at least one neighbouring residue by an —NH—CO— bond and on the other hand, if the residue is an aminoacyl residue, is of opposite chirality to that of the same aminoacyl residue in the peptide chain of the parent peptide.

The retro-inverso peptides used in the context of the present invention are more particularly those as defined above, and correspond to the abovementioned formula (II), in which at least one of the residues is bonded to at least one of its neighbouring residues by an —NH—CO— bond, and if the residue is an aminoacyl residue, is of opposite chirality to that of the corresponding aminoacyl residue in the parent peptide.

These abovementioned retro-inverso peptides are:

partly retro-inverso peptides, that is to say:

a) either partly retro-totally inverso peptides, that is to say in which only one or more of, but not all, the bonds between the residues is (are) (an) —NH—CO— bond(s), and in which all the aminoacyl residues bonded to at least one neighbouring residue by an —NH—CO— bond is (are) of opposite chirality to that of the corresponding aminoacyl residue in the parent peptide, b) or partly retro-partly inverso peptides, that is to say in which only one or more of, but not all, the bonds between the residues is (are) (an) —NH-CO— bond(s), and in which at least one of, but not all, the aminoacyl residues bonded to at least one neighbouring residue by an —NH—CO— bond is (are) of opposite chirality to that of the corresponding aminoacyl residue in the parent peptide, these two types of partly retro-inverso peptides being represented by the formula (II), and more particularly is described by the cases of FIGS. 2, 3 and 4 which relate to them, or totally retro-partly inverso peptides, that is to say in which all the bonds between the residues are —NH—CO— bonds, and in which at least one of, but not all, the aminoacyl residues bonded to at least one neighbouring residue by an —NH—CO— bond is (are) of opposite chirality to that of the corresponding aminoacyl residue in the parent peptide, or totally retro-inverso peptides, that is to say in which all the bonds between the residues are —NH—CO— bonds, and in which all the aminoacyl residues of the peptide chain of these retro-inverso peptides are of opposite chirality to that of their corresponding aminoacyl residues in the parent peptide.

These last two types of retro-inverso peptides are represented by the formula (II), and are more particularly described by the case of FIG. 1 which relates to them.

The retro-inverso peptides used in the context of the present invention are advantageously totally retro-inverso.

Another advantageous class of retro-inverso peptides used in the context of the invention has at least two consecutive "retro-inverso" bonds.

The invention more particularly relates to the abovementioned use of retro peptides as immunoretroids.

Retro peptide is to be understood as meaning any peptide corresponding to the definition given above for immunoretroids used in the context of the present invention, the said peptide being more particularly made up of a peptide chain in which at least one of the residues is bonded to at least one neighbouring residue by an —NH—CO— bond, the chirality of all the aminoacyl residues involved in at least one —NH—CO— bond being maintained with respect to the corresponding residue of the peptide chain of the parent peptide.

The retro peptides used in the context of the present invention are more particularly those such as are defined above and correspond to the abovementioned formula (II), in which at least one of the residues is bonded to at least one neighbouring residue by an —NH—CO— bond.

The abovementioned retro peptides are:

either partly retro peptides, represented by the formula (II), and more particularly described by the cases of FIGS. 2, 3 and 4 which relate to them, that is to say in which only one or more of, but not all, the bonds between the aminoacyl residues is (are) (an) —NH—CO— bond(s), or totally retro peptides, represented by the formula (II), and more particularly described by the case of FIG. 1 which relates to them, that is to say in which all the bonds between the aminoacyl residues are —NH—CO— bonds.

The totally retro peptides used in the context of the present invention are advantageously totally retro.

Another suitable class of retro peptides used in the invention have two consecutive "retro" bonds.

The diseases which can be diagnosed or treated with the aid of pharmaceutical compositions based on immunoretroids in the context of the present invention are chiefly diseases of a viral or bacterial origin, or are autoimmune diseases, or also neurodegenerative diseases.

Among the diseases of viral origin which can be diagnosed or treated in the context of the present invention there may be mentioned:

AIDS caused by the human immunodeficiency virus HIV1 and HIV2, paraplegia associated with HTVL-1, or adult T cell leukaemia caused by the human T cell leukaemia virus (HTLV virus), infections caused by the respiratory syncytial virus, infections caused by the Coxsackie virus, for example acute lymphocytic meningitis, infections caused by the Epstein-Barr virus, for example infectious mononucleosis, infections caused by the cytomegalovirus, for example cytomegalic inclusion disease, herpes caused by the human herpes virus, herpes caused by the herpes simplex 6 virus, infections caused by the human Parvovirus B19, for example infectious gastroenteritis, hepatitis B caused by the hepatitis B virus, hepatitis C, caused by the hepatitis C virus, influenza caused by the influenza virus, rubeola caused by the rubeola virus, infections caused by the Dengue virus, for example arboviroses, colds, rhinitis or coryza caused by rhinoviruses and aphthous fever caused by the aphthous fever virus.

Among the main autoimmune diseases which can be treated in the context of the present invention there may be mentioned those summarized in Table A which follows.

TABLE A

Main autoimmune diseases (from the top down, autoimmune diseases specific to organs to autoimmune diseases non-specific to organs).

| Diseases | Autoantigen targets |
|---|---|
| Hashimoto's thyroiditis | Thyroglobulin, microsomes |
| Basedow's disease | TSH receptor |
| Addison's disease | Suprarenal cortex |
| Hypophysial insufficiency | Hypophysis |
| Biermer's gastritis | Parietal cell of the stomach |
| | Intrinsic factor |
| Certain sterilities | Spermatozoa, ovaries |
| Type I juvenile diabetes | Islets of Langerhans, insulin |
| Goodpasture's syndrome | Glomerular basement membrane |
| Myasthenia | Striated muscle, acetylcholine receptor |
| Acute articular rheumatism | Myocardium (*streptococci*) |
| Pemphigus | Epidermal intercellular bridges |
| Bullous pemphigoid | Cutaneous basement membrane |
| Dermatitis herpetiformis | Gliadin, reticulin |
| Vitiligo | Melanocytes |
| Alopecia | Hair follicles |
| Psoriasis | |
| Sympathetic ophthalmia | Uvea |

TABLE A-continued

Main autoimmune diseases (from the top down, autoimmune diseases specific to organs to autoimmune diseases non-specific to organs).

| Diseases | Autoantigen targets |
|---|---|
| Uveitis | Anterior chamber of the eye |
| Guillain-Baré syndrome | |
| Plaque sclerosis | Myelin |
| Haemolytic anaemia | Red blood corpuscles |
| Idiopathic thrombopenic purpura | Platelets |
| Idiopathic leukopenia | Granulocytes |
| Primary biliary cirrhosis | Mitochondria |
| Active chronic hepatitis | Smooth muscle, nuclei |
| Haemorrhagic rectocolitis | |
| Crohn's ileitis | Colon (*E. coli*) |
| Gougerot-Sjögren syndrome | Nuclei: SS-A, SS-B |
| Rheumatoid polyarthritis | IgG, nuclei |
| Dermatopolymyositis | Nuclei: Jo1, muscles |
| Scleroderma | Nuclei: Scl-70 |
| Mixed connectivitis | Nuclei: RNP |
| Discoid lupus erythematosus | Nuclei: |
| Disseminated lupus erythematosus | Nuclei: DNA, antigen Sm |
| | Coagulation factors |
| | Cardiolipin, etc. |

The invention also relates to antibodies to the immunoretroids according to the invention, also called anti-immunoretroid antibodies.

The anti-immunoretroid antibodies according to the invention are polyclonal or monoclonal antibodies.

The abovementioned polyclonal antibodies are obtained by immunization of an animal with at least one immunoretroid according to the invention, followed by recovery of the required antibodies in a purified form by taking serum from the said animal and separating the said antibodies from others contained in the serum, in particular by affinity chromatography over a column on which is fixed an antigen recognized specifically by the antibodies, in particular an immunoretroid according to the invention.

The monoclonal antibodies according to the invention can be obtained by the hybridoma technique, the general principle of which is described below.

An animal, generally a mouse (or cells in culture in the context of in vitro immunizations) is first immunized with an immunoretroid according to the invention, the B lymphocytes of which then being capable of producing antibodies to the immunoretroid and/or to this protein and/or to the parent peptide. These lymphocytes which produce antibodies are then fused with "immortal" myelomatous cells (murine cells in the example) to give rise to hybridomas. From the heterogeneous mixture of cells thus obtained, cells capable of producing a particular antibody and of multiplying indefinitely are then selected. Each hybridoma is multiplied in the form of a clone, each leading to the production of a monoclonal antibody of which the recognition properties with respect to the immunoretroid of the invention can be tested, for example, by ELISA, by immunotransfer in one or two dimensions, under immunofluorescence or with the aid of a biocaptor. The monoclonal antibodies selected in this way are then purified, in particular by the technique of affinity chromatography described above.

The antibodies according to the invention are more particularly characterized in that they are capable of forming a complex with the immunoretroids, and/or with the parent peptides or proteins corresponding to the latter.

In this respect, the invention more particularly relates to the antibodies as defined above, which are characterized in that they recognize the retro-inverso peptides and/or the corresponding parent peptides or proteins, in particular the parent peptides or proteins of the L configuration.

The invention also more particularly relates to antibodies as defined above, which are characterized in that they recognize the retro peptides, and/or the enantiomers of the corresponding parent peptides or proteins, in particular the enantiomers of the parent peptides or proteins of the L-configuration.

The antibodies according to the invention are more particularly also characterized in that they are protective antibodies, that is to say antibodies which, if they are administered into the organism of an individual carrying a pathogenic endogenous or exogenous protein or if their formation is induced by administration into the organism of the individual of an immunoretroid according to the invention which can be recognized by such antibodies, are capable of bonding to the said endogenous or exogenous protein under conditions such that the pathogenic character associated with this protein is thus neutralized.

The anti-immunoretroid antibodies of the invention recognize the parent peptide or the parent protein with an affinity which is at least equal to that shown by the anti-parent peptide or anti-parent protein antibodies with respect to the parent peptide or the parent protein.

The anti-parent peptide or anti-parent protein antibodies recognize the immunoretroids used in the context of the invention with an affinity which is at least equal to that shown by these same said antibodies with respect to the parent peptides or parent proteins corresponding to these said immunoretroids.

The affinity referred to above can be measured by the equilibrium affinity constant Ka of complexes involving one of the said antibodies with one of the said antigens.

The invention also relates to anti-idiotypes which are capable of forming a complex with the antibodies according to the invention, these anti-idiotypes being obtained by immunization of an animal with the said antibodies as defined above according to the invention.

The invention also more particularly relates to antigen-antibody complexes formed between the immunoretroids according to the invention, or their parent peptide or parent protein, and the antibodies as defined above.

In this respect, the invention more particularly relates to the following complexes:

| parent peptide | antibody to a retro-inverso peptide corresponding to the parent peptide |
| --- | --- |
| parent protein | antibody to a retro-inverso peptide corresponding to a sequence of the parent peptide derived from the parent protein |
| parent protein | antibody to a retro peptide corresponding to a sequence of the parent peptide derived from the parent protein |
| parent peptide | antibody to a retro peptide corresponding to the enantiomer of the parent peptide |
| retro-inverso peptide corresponding to a parent peptide | antibody to the parent peptide |
| retro-inverso peptide corresponding to a sequence of the parent peptide derived from the parent protein | antibody to the parent protein |
| retro-inverso peptide corresponding to a parent peptide | antibody to a retro-inverso peptide corresponding to the parent peptide |
| retro-inverso peptide corresponding to a parent peptide | antibody to a retro peptide corresponding to the enantiomer of the parent peptide |
| enantiomer of a parent peptide | antibody to a retro peptide corresponding to the enantiomer of the parent peptide |
| enantiomer of a parent peptide | antibody to a retro-inverso peptide corresponding to the parent peptide |
| retro peptide corresponding to a sequence of the parent peptide derived from the parent protein | antibody to the parent protein |
| retro peptide corresponding to the enantiomer of a parent peptide | antibody to the enantiomer of the parent peptide |
| retro peptide corresponding to the enantiomer of a parent peptide | antibody to a retro-inverso peptide corresponding to the parent peptide |
| retro peptide corresponding to the enantiomer of a parent peptide | antibody to a retro peptide corresponding to the enantiomer of the parent peptide |

Particularly preferred antigen-antibody complexes in the context of the invention are the following:

| parent protein | antibody to a retro-inverso peptide corresponding to a parent peptide derived from the parent protein |
| --- | --- |
| parent peptide | antibody to a retro-inverso peptide corresponding to the parent peptide |
| retro-inverso peptide corresponding to a parent peptide | antibody to the parent peptide or the parent protein |
| retro-inverso peptide corresponding to a parent peptide | antibody to a retro-inverso peptide corresponding to the parent peptide |

Parent peptide derived from the parent protein means a sequence of the parent protein.

It should be noted that all the complexes defined above are such that they have a stability which is at least equal to that of these complexes in which, if an immunoretroid occurs, it is replaced by a parent peptide or a parent protein, and if an anti-immunoretroid antibody occurs, it is replaced by an anti-parent peptide or anti-parent protein antibody.

In particular, the parent peptide/parent protein-anti-immunoretroid antibody complexes are at least as stable as the complexes of parent peptide/parent protein-antibody to the parent peptide or protein corresponding to these said immunoretroids.

It should also be noted that the complexes of immunoretroid-antibody to the parent peptide or the parent protein are at least as stable as the corresponding complexes in which the immunoretroid peptides are replaced by the parent peptide or the parent protein.

The invention advantageously relates to antigen-antibody complexes in which the antigen is an immunoretroid and/or the antibody is an antibody to an immunoretroid and which have an affinity constant greater than the affinity constant shown by the parent antigen (that is to say parent peptide or parent protein)-antibody complexes with respect to the parent antigens (that is to say antibodies to the parent peptide or the parent protein).

According to an advantageous embodiment, the invention relates to the antigen-antibody complexes in which the antigen is an immunoretroid (for example a retro-inverso) and the antibody is an antibody to the parent peptide or the parent protein (corresponding to the said retro-inverso) and which have an affinity constant greater than the affinity constant shown by the antigen-antibody complex in which the antigen is the parent peptide or the parent protein and the antibody is an antibody to the parent peptide or the parent protein.

In order to define the concepts, the order of magnitude according to which "the affinity constant is greater" may vary from about 5 to about 1,000, in particular from about 7 to about 1,000, advantageously from about 10 to 1,000, and in particular from about 10 to about 100.

In one embodiment, the present invention provides a system which includes a compound of the following formula (II):

$$A\text{—}CH(R_i)\text{—}NH\text{—}[CO\text{—}CH(R_k)\text{—}NH]_{j-i}\text{—}CO\text{—}CH(R_j+1)\text{—}B \quad (II)$$

wherein
  n, which is the number of aminoacyl residues in formula I, is a whole number from 3–1,000, and $R_i$, $R_k$, and $R_{j+1}$ are side chains of the aminoacyl residues,
  i, j and k are whole numbers
wherein
  $1 \leq i \leq j < n$, and
  if i=j, k=0; and
  if i<j, $i+1 \leq k \leq j$;
  such that,
  where i=1 and j+1=n, A is Q and B is M;
  where i=1 and j+1≠n, A is Q and B is L;
  where i≠1 and j+1=n, A is T and B is M; and
  where i≠1 and j+1≠n, A is T and B is L;
  Q being selected from H—, $H_2N$—, P—HN—, RR'N—, $H_2NCO$—, RR'NCO—, and RCO—;
  M being selected from H—, —COOH, —COOR, —$CONH_2$, —CONRR' and —NHCOR;
  L being —CO—NH—CH($R_{j+2}$)—CO— ... —NH—CH ($R_n$)—CO—Y wherein Y is selected from —OH, —OR, —$NH_2$, and —NRR'; and
  T being X—HN—CH($R_1$)—CO— ... —NH—CH($R_i\_1$) CO—NH— wherein X is selected from H—, P—, R— and RCO—;
wherein
  R and R' are independently selected hydrogen, $C_{1-25}$ alkyl, $C_{3-25}$ allyl, $C_{6-25}$ aryl, benzyl, 2-phenyl-ethyl, methylfluorenyl, glycolamide and benzhydrylglycolamide; and
  P is a protecting group;
  wherein the compound is an immunoretroid form of an immunologically active peptide which binds to an antibody or an antibody fragment directed against said immunologically active peptide with at least equal affinity as said immunologically active peptide;
  and the system further contains at least one reagent, or components necessary to form said reagent, for forming an immune complex between the compound and the antibody or antibody fragment; and, the system optionally further contains a solid support for immobilizing said immune complex, and, optionally also contains at least one reagent for detecting the immune complex.

In one embodiment, the present invention provides a system for detecting a peptide such that the system contains an antibody or antibody fragment specific for the peptide wherein said antibody or antibody fragment was produced by an immunological reaction with an immunoretroid form of the peptide wherein the peptide is selected from the the following:
  C-terminal epitope of protein histone H3,
  FP peptide from serotype A12 of foot-and-mouth disease virus,
  FL peptide from serotype A12 of foot-and-mouth disease virus,
  SL peptide from serotype A12 of foot-and-mouth disease virus;
  internal domain 277–291 of 52 kD SSA/Ro protein,
  internal domain 304–324 of 60 kD SSA/Ro protein,
  internal domain 28–45 of histone H3,
  site A of haemagglutinin of influenza virus,
  peptide C18L of peptide HA91–108 of haemagglutinin of influenza virus,
  peptide 9B1 of *Schistosoma mansoni*,
  a mimotope of measles virus,
  a cyclic peptide of human immunodeficiency virus glycoprotein 41,
  a cytotoxic T-cell epitope of influenza virus matrix comprising epitope 56–68,
  an auxiliary T epitope of tetanus toxin,
  a poliovirus VP1 peptide, and
  a peptide containing the third constant region of a mouse heavy chain
  IgG2a allopeptide $\gamma 2a^b$;
  the immunoretroid form being a retro-inverso or a retro- form of the peptide;
  and the system optionally further contains at least one reagent, or components necessary to form a reagent, for forming an immune complex between the antibody or antibody fragment and the peptide; and
  the system may further optionally contain a solid support for immobilizing the complex, and, the system may further optionally contain, at least one reagent for detecting the immune complex.

The invention also relates to the complexes between an immunoretroid as defined above and a molecule of major histocompatibility complex (also called MHC-immunoretroid complex).

In fact, the immune response involves recognition of an endogenous or exogenous antigen by specialized cells. To be recognized, the antigen should initially be presented in an adequate manner by antigen-presenting cells (APC). Whereas B lymphocytes recognize epitopes carried by intact non-modified antigens, presentation of the antigen to T lymphocytes is more complex insofar as the antigen is first internalized by the presenting cell, proteolysed, and then possibly reexpressed on its surface in the form of peptide fragments in combination with the proteins of major histocompatibility complex (MHC). The T lymphocyte, which does not recognize the native antigen, recognizes a peptide fragment combined with an MHC molecule.

These MHC molecules belong to two classes: I and II.

The molecules of class I are transmembrane glycoproteins made up of a heavy polymorphic α-chain combined non-covalently with a with a non-glycosylated light β2m chain. Their crystallographic structure has been resolved (Bjorkman et al. (1987), Nature, 329: 506–512), and shows the presence of a furrow which forms the presentation site of the peptide, the base of which is made up of eight β-sheets and the sides of which are made up of two α-helices. These molecules are presented on the surface of virtually all cells.

The molecules of class II are also membrane glycoproteins made up of two polymorphic α- and β-chains bonded non-covalently to form, as the recently elucidated crystallographic structure shows (Brown et al. (1993), Nature, 364: 33–39), a β-pleated platform supporting two α-helices. The furrow formed is the presentation site of the peptide. These molecules are expressed only on the surface of certain cells, including macrophages and B cells.

Cytotoxic T lymphocytes (cells which have CD8 markers) recognize proteolytic fragments of viral proteins associated with MHC molecules of class I and cause lysis of cells presenting the antigen.

Auxiliary T lymphocytes (cells which carry CD4 markers) recognize exogenous protein fragments captured by endocytosis and present in combination with the MHC molecules of class II, and induce cellular stimulation of the immune response.

The invention also relates to the complexes between an immunoretroid according to the invention and a T cell receptor.

The invention also relates to the complexes between a molecule of major histocompatibility complex, an immunoretroid as defined above, and a T cell receptor (also called MHC-immunoretroid-T receptor complex).

The invention also relates to the use of the immunoretroids as defined above for implementation of methods for in vitro diagnosis of diseases, such as those mentioned above, associated with the presence in the organism of an individual of one or more exogenous or endogenous protein(s) capable on the one hand of being involved directly or indirectly in the process of the appearance and/or development of these diseases, and on the other hand of being recognized by the anti-immunoretroid antibodies according to the invention, or by the immunoretroids according to the invention, for example in the case of detection of antibodies in the patient.

In this respect, the invention more particularly relates to any method for in vitro diagnosis as defined above and comprising:

bringing a biological sample originating from a patient who may carry antibodies to the said endogenous or exogenous proteins into contact with an immunoretroid according to the invention under conditions which allow reaction between the antibodies to the said proteins, which antibodies may be present in the biological sample, and the said immunoretroid;

in vitro detection of the antigen-antibody complex as defined above according to the invention, which may be formed in the preceding stage, or in vitro detection of the antibody in the patient by a competition test using an anti-immunoretroid antibody.

The immunoretroid used in the abovementioned method for in vitro diagnosis is advantageously a retro-inverso peptide corresponding to all or part of the said endogenous or exogenous proteins, or corresponding to a peptide which is capable of being recognized by antibodies which themselves recognize the exogenous or endogenous proteins.

According to another preferred embodiment of the abovementioned method for in vitro diagnosis, the immunoretroid used is a retro peptide corresponding to all or part of the said endogenous or exogenous proteins, or corresponding to a peptide which is capable of being recognized by antibodies which themselves recognize the exogenous or endogenous proteins.

The invention also relates to any method for in vitro diagnosis as defined above and comprising:

bringing a biological sample originating from an individual who may be a carrier of the said endogenous or exogenous proteins into contact with at least one of the antibodies, as defined above, to an immunoretroid according to the invention under conditions which allow reaction between the said proteins which may be present in the biological sample and the said antibodies to the said immunoretroid;

in vitro detection of the antigen-antibody complex as defined above which may be formed in the preceding stage, or detection of circulating antigens in competition tests using one of the said immunoretroids.

The antibodies to the immunoretroid which are used in the abovementioned method for in vitro diagnosis are advantageously those antibodies, described above according to the invention, to a retro-inverso peptide corresponding to all or part of the said endogenous or exogenous proteins.

According to another preferred embodiment of the abovementioned method for in vitro diagnosis, the antibodies to the immunoretroid are those antibodies, as defined above according to the invention, to a retro peptide corresponding to all or part of the said endogenous or exogenous proteins.

The abovementioned methods for diagnosis of the invention are advantageously carried out in the following manner:

incubation of the biological sample which may contain the antigens (exogenous or endogenous protein or peptide), or antibodies to these antigens, these antigens or antibodies being associated with a disease or a family of specific diseases, in particular with the diseases described above, with, respectively, anti-immunoretroid antibodies according to the invention which are capable of recognizing the said antigens, or immunoretroids according to the invention which are capable of being recognized by the said antibodies to these antigens, the said antigens or antibodies to the latter being fixed on a solid support, in particular inside the wells of microtitration plates of the type usually used for implementation of detection or assay techniques commonly known by the name ELISA (enzyme-linked immunosorbent assay), rinsing of the solid support, incubation of the elements remaining fixed on the solid support after the preceding rinsing stage:

either with a medium comprising antibodies, in particular anti-immunoretroid antibodies according to the invention, which are marked (in particular in a radioactive, enzymatic or fluorescent manner) or are capable of being recognized in their turn by a marked reagent, the said marked antibodies being capable of recognizing the antigens present in the biological sample which remain bonded, after the preceding rinsing stage, to the anti-immunoretroid antibodies according to the invention initially fixed on the solid support, or with a medium comprising antigens, in particular immunoretroids according to the invention, which are marked (in particular in a radioactive, enzymatic or fluorescent manner) or capable of being recognized in their turn by a marked reagent, the said marked antigens being capable of recognizing the antibodies present in the biological sample which remain bonded, after the preceding rinsing stage, to the immunoretroids according to the invention initially fixed to the solid support, rinsing of the solid support, detection of the marked antigens or antibodies remaining bonded, respectively, to the antibodies or antigens of the biological sample during the preceding incubation stage.

The methods for in vitro diagnosis of the invention are advantageously carried out with the aid of totally retro-inverso peptides or totally retro peptides, or also antibodies to these totally retro-inverso or totally retro peptides.

In one embodiment, the present invention provides an immunological method of detecting lupus in an individual suspected of having lupus wherein the method entails contacting an immunoretroid form of a C-terminal hexapeptide of histone H3 with a biological sample from the individual under conditions where an immune complex containing the immunoretroid form and an antibody specific to the C-terminal hexapeptide of histone H3 in the sample will form, if present; and detecting the complex, wherein the complex, when present, is indicative of said individual having lupus.

In another embodiment, the present invention provides an immunological method of detecting one of disseminated lupus erythematosus and Sjögren's syndrome in an individual suspecting of having one of disseminated lupus erythematosus and Sjögren's syndrome, wherein the method entails contacting an immunoretroid form of at least one of internal domain 304–324 of 60 kD SSA/Ro protein and internal domain 277–291 of 52 kD SSA/Ro protein, with a biological sample from the individual under conditions where an immune complex containing the immunoretroid form and an antibody specific to the protein will form, if present; and detecting the complex, wherein the complex, when present, is indicative of said individual having one of disseminated lupus erythematosus and Sjörgen's syndrome.

The invention also relates to the requisites or kits, or a system, for implementation of the methods for in vitro diagnosis as described above, comprising:

an immunoretroid according to the invention chosen from a retro-inverso peptide and/or a retro peptide corresponding to all or part of the said endogenous or exogenous proteins, or corresponding to a peptide which is capable of being recognized by antibodies which themselves recognize the exogenous or endogenous proteins, or anti-immunoretroid antibodies, according to the invention, to this retro-inverso peptide and/or this retro peptide;

reagents for rendering a medium capable of the formation of an immunological reaction;

reagents which allow detection of the antigen-antibody complex, belonging to the list of compounds defined above, which has been produced as a result of the immunological reaction, the said reagents optionally comprising a marker or being capable of being recognized in their turn by a marked reagent, more particularly in the case where the abovementioned immunoretroid or anti-immunoretroid antibodies are not marked.

In one embodiment, the present invention provides an immunological method of detecting an antibody or antibody fragment which binds to an immunologically active peptide wherein the method includes contacting a sample suspecting of containing the antibody or antibody fragment with an immunoretroid form of the immunologically active peptide under conditions where an immune complex between the immunoretroid form and the antibody or antibody fragment will form, if the antibody or antibody fragment is present; and detecting the complex;
the immunoretroid form comprising a compound of the following formula (II):

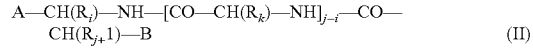

$$A-CH(R_i)-NH-[CO-CH(R_k)-NH]_{j-i}-CO-CH(R_{j+1})-B \quad (II)$$

wherein n, which is the number of aminoacyl residues in formula I, is a whole number from 3–1,000, and $R_i$, $R_k$, and $R_{j+1}$ are side chains of the aminoacyl residues, i, j and k are whole numbers wherein $1 \leq i \leq j < n$, and if i=j, k=0; and if i<j, $i+1 \leq k \leq j$;

such that, where i=1 and j+1=n, A is Q and B is M;

where i=1 and j+1≠n, A is Q and B is L;

where i≠1 and j+1=n, A is T and B is M; and where i≠1 and j+1≠n, A is T and B is L;

Q being selected from the group consisting of H—, $H_2N$—, P—HN—, RR'N—, $H_2NCO$—, RR'NCO—, RCO—;

M being selected from the group consisting of H—, —COOH, —COOR, —CONH$_2$, —CONRR' and —NHCOR;

L being —CO—NH—CH($R_{j+1}$2)—CO— . . . —NH—CH ($R_n$)—CO—Y wherein Y is selected from the group consisting of —OH, —OR, —NH$_2$, and —NRR'; and T being X—HN—CH($R_1$)—CO— . . . —NH—CH($R_{i-1}$) CO—NH— wherein X is selected from the group consisting of H—, P—, R— and RCO—;

wherein

R and R' are independently selected from the group consisting of hydrogen, $C_{1-25}$ alkyl, $C_{3-25}$ allyl, $C_{6-25}$ aryl, benzyl, 2-phenyl-ethyl, methyl-fluorenyl, glycolamide and benzhydrylglycolamide; and P is a protecting group;

said compound being an immunoretroid form of an immunologically active peptide which binds to an antibody or an antibody fragment directed against said immunologically active peptide with at least equal affinity as said immunologically active peptide.

The invention also relates to the use of at least one immunoretroid as defined above for the preparation of a medicament intended for prevention or treatment of diseases associated with the presence in the organism of an individual of one or more exogenous or endogenous protein(s) which may be directly or indirectly involved in the process of the appearance and/or development of these diseases.

The abovementioned diseases which are capable of being treated in the context of the present invention are chiefly either diseases of viral, bacterial or parasitic origin, if they are associated with the presence of the microorganism itself, or of an exogenous protein or peptide originating from a viral, bacterial or parasitic particle, or autoimmune diseases, if they are associated with the presence of endogenous proteins or peptides which disturb normal physiological functioning of an organism where the latter play an antibody role directly or induce the formation of antibodies which recognize and alter particular sites of the organism (for example by forming depots of antibody-antigen complexes, causing inflammatory states etc.).

The abovementioned pathologies can also be neurodegenerative diseases if they are associated with the presence in the organism of exogenous proteins which have the effect of causing neurological lesions.

The present invention provides a method of treating an autoimmune disease which includes administering an immunoretroid form of an immunologically active peptide, wherein the immunoretroid form includes a compound of the following formula (II):

$$A—CH(R_i)—NH—[CO—CH(R_k)—NH]_{j-i}—CO—CH(R_{j+}1)—B \quad (II)$$

wherein n, which is the number of aminoacyl residues in formula II, is a whole number from 3–1,000, and $R_i$, $R_k$, and $R_{j+}1$ are side chains of the aminoacyl residues, i, j and k are whole numbers wherein $1 \leq i \leq j < n$, and if i=j, k=0; and if i<j, $i+1 \leq k \leq j$;

such that, where i=1 and j+1=n, A is Q and B is M;

where i=1 and j+1≠n, A is Q and B is L;

where i≠1 and j+1=n, A is T and B is M; and where i≠1 and j+1≠n, A is T and B is L;

Q is selected from H—, H$_2$N—, P—HN—, RR'N—, H$_2$NCO—, RR'NCO—, and RCO—;

M is selected from H—, —COOH, —COOR, —CONH$_2$, —CONRR' and —NHCOR;

L is —CO—NH—CH(R$_{j+}$2)—CO— . . . —NH—CH(R$_n$)—CO—Y wherein Y is selected from —OH, —OR, —NH$_2$, and —NRR'; and T is X—HN—CH(R$_1$)—CO— . . . —NH—CH(R$_{i-}$1)CO—NH— wherein X is selected from H—, P—, R— and RCO—;

wherein

R and R' are independently selected from hydrogen, $C_{1-25}$ alkyl, $C_{3-25}$ allyl, $C_{6-25}$ aryl, benzyl, 2-phenyl-ethyl, methyl-fluorenyl, glycolamide and benzhydrylglycolamide; and P is a protecting group;

wherein the compound is an immunoretroid form of an immunologically active peptide which binds to an antibody or an antibody fragment directed against the immunologically active peptide with at least equal affinity as the immunologically active peptide.

In one further embodiment, the immunologically active peptide of the method of treating an autoimmune disease according to the present invention is an autoreactive T cell antagonist peptide selected from a poliovirus VP1 peptide and a peptide containing the third constant region of a mouse heavy chain IgG2a allopeptide γ2a$^b$.

The immunoretroids used for the preparation of pharmaceutical compositions or vaccines above and below are advantageously totally retro-inverso peptides or totally retro peptides.

The invention more particularly relates to the use of at least one immunoretroid as defined above for the preparation of a vaccine in the context of prevention of diseases associated with the presence in the organism of an individual of one or more exogenous or endogenous protein(s) capable of being recognized by antibodies to the immunoretroids or to the anti-idiotypes according to the invention.

The invention also relates to the pharmaceutical compositions, in particular vaccines, comprising at least one anti-idiotype as defined above, in combination with a physiologically acceptable vehicle. The vaccine of the present invention may optionally contain adjuvant. Moreover, the peptide of the present invention may be bound to a liposome, as described herein and as known in the art, such as when provided in the form of a vaccine.

The present invention further provides a vaccine containing an immunoretroid form of an immunologically active peptide, the immunoretroid being a derivative of the immunologically active peptide which binds to an antibody or an antibody fragment to the immunologically active peptide with at least an equal affinity as the immunologically active peptide; wherein the immunoretroid form is a retro-inverso peptide or a retro-peptide of a peptide, wherein the immunoretroid form of the immunologically active peptide has the following formula II:

$$A—CH(R_i)—NH—[CO—CH(R_k)—NH]_{j-i}—CO—CH(R_{j+}1)—B \quad (II)$$

wherein n, which is the number of aminoacyl residues in formula I, is a whole number from 3–1,000, and $R_i$, $R_k$, and $R_{j+}1$ are side chains of the aminoacyl residues, i, j and k are whole numbers wherein $1 \leq i \leq j < n$, and if i=j, k=0; and if i<j, $i+1 \leq k \leq j$;

such that, where i=1 and j+1=n, A is Q and B is M;

where i=1 and j+1≠n, A is Q and B is L;

where i≠1 and j+1=n, A is T and B is M; and where i≠1 and j+1≠n, A is T and B is L;

Q is selected from H—, H$_2$N—, P—HN—, RR'N—, H$_2$NCO—, RR'NCO—, and RCO—;

M is selected from H—, —COOH, —COOR, —CONH$_2$, —CONRR' and —NHCOR;

L is —CO—NH—CH(R$_{j+}$2)—CO— . . . —NH—CH(R$_n$)—CO—Y wherein Y is selected from —OH, —OR, —NH$_2$, and —NRR'; and T is X—HN—CH(R$_1$)—CO— . . . —NH—CH(R$_{i-}$1)CO—NH— wherein X is selected from H—, P—, R— and RCO—;

wherein

R and R' are independently selected from hydrogen, $C_{1-25}$ alkyl, $C_{3-25}$ allyl, $C_{6-25}$ aryl, benzyl, 2-phenyl-ethyl, methyl-fluorenyl, glycolamide and benzhydrylglycolamide; and P is a protecting group; and the vaccine further contains a physiologically acceptable vehicle.

In a further embodiment, the vaccine according to the present invention includes at least one peptide selected from the following:

a FP peptide from serotype A12 of foot-and-mouth disease virus, a FL peptide from serotype A12 of foot-and-mouth disease virus, a SL peptide from serotype A12 of foot-and-mouth disease virus, site A of haemagglutinin of influenza virus.

The anti-idiotypes used in the abovementioned pharmaceutical compositions are advantageously obtained with the aid of totally retro-inverso or totally retro peptides.

The present invention particularly provides a vaccine containing an immunoretroid form of an immunologically active peptide, wherein the immunoretroid is a derivative of the immunologically active peptide which binds to an antibody or an antibody fragment to the immunologically active peptide with at least an equal affinity as the immunologically active peptide; wherein the immunoretroid form is a retro-inverso peptide or a retro-peptide of an immunologically active peptide selected from at least any one of the following a FP peptide from serotype A12 of foot-and-mouth disease virus, a FL peptide from serotype A12 of foot-and-mouth disease virus, a SL peptide from serotype A12 of foot-and-mouth disease virus, a site A of haemagglutinin of influenza virus, a peptide C18L of peptide HA91–108 of haemagglutinin of influenza virus, a peptide 9B1 of *Schistosoma mansoni*, a mimotope of measles virus, a cyclic peptide of human immunodeficiency virus glycoprotein 41, a cytotoxic T-cell epitope of influenza virus matrix comprising epitope 56–68, an auxiliary T epitope of tetanus toxin, a poliovirus VP1 peptide, and a physiologically acceptable vehicle.

The invention also relates to any pharmaceutical composition comprising at least one immunoretroid as defined above or at least one abovementioned anti-idiotype combined with a molecule, which may or may not be a protein carrier and can induce in vivo the production of antibodies which neutralize the said exogenous or endogenous proteins responsible for the disease, or induce in vivo a cytotoxic cell immune response as described above.

By way of illustration in the field of diagnosis, the invention more particularly relates to immunoretroids given below:

1) Retro-Inverso Peptide of a Peptide Called "C18L" and Deriving from the Peptide HA91–108 of the Haemagglutinin of the Influenza Virus (Strain A/Texas/1/77) (the said Peptide being Called "C18L" Because it Comprises 18 Residues, the First Residue being Cysteine, and the Last Residue being Leucine).

Sequences of the parent L-peptide (C18L) and of the double blocked L-peptide (called *C18L*) are shown below:

parent L-peptide C18L (SEQ ID NO:14):
H-Cys-Lys-Ala-Phe-Ser-Asn-Ser-Tyr-Pro-Tyr-Asp-Val-Pro-Asp-Tyr-Ala-Ser-Leu-OH, double blocked L-peptide *C18L*:
CH$_3$CO-Cys-Lys-Ala-Phe-Ser-Asn-Ser-Tyr-Pro-Tyr-Asp-Val-Pro-Asp-Tyr-Ala-Ser-Leu-NH$_2$, "double blocked" means that the L-peptide is blocked at its two ends: the NH$_2$— and COOH-termini of the parent peptide were acetylated and carboxamidated respectively.

Sequence of the double blocked retro-inverso peptide:
CH$_3$CO-(D)Leu-(D) Ser-(D)Ala-(D)Tyr-(D)Asp-(D)Pro-(D)Val-(D)Asp-(D)Tyr-(D)Pro-(D)Tyr-(D)Ser-(D)Asn-(D)Ser-(D)Phe-(D)Ala-(D)Lys-(D)Cys-NH$_2$ In the same way, "double blocked" means that the retro-inverso peptide is blocked at its two ends: the NH$_2$— and COOH-termini of the retro-inverso peptide were acetylated and carboxamidated respectively.

Sequence of the retro-inverso peptide:
HO-(D)Leu-(D)Ser-(D)Ala-(D)Tyr-(D)Asp-(D)Pro-(D)Val-(D)Asp-(D)Tyr-(D)Pro-(D)Tyr-(D)Ser-(D)Asn-(D)Ser-(D)Phe-(D)Ala-(D)Lys-(D)Cys-H 2) RETRO-INVERSO Peptide of the Peptide 9B1 of *Schistosoma mansoni*.

Sequences of the parent L-peptide (9B1) and of the double blocked L-peptide (*9B1*) are shown below:

parent L-peptide 9B1 (SEQ ID NO:15):
H-Cys-Gly-Phe-Thr-Thr-Asn-Glu-Glu-Arg-Tyr-Asn-Val-Phe-Ala-Glu-OH double blocked L-peptide *9B1*:
CH$_3$CO-Cys-Gly-Phe-Thr-Thr-Asn-Glu-Glu-Arg-Tyr-Asn-Val-Phe-Ala-Glu-NH$_2$ Sequence of the double blocked retro-inverso peptide:
CH$_3$CO-(D)Glu-(D)Ala-(D)Phe-(D)Val-(D)Asn-(D)Tyr-(D)Arg-(D)Glu-(D)Glu-(D)Asn-(D)Thr-(D)Thr-(D)Phe-(D)Gly-(D)Cys-NH$_2$ Sequence of the retro-inverso peptide:
HO-(D)Glu-(D)Ala-(D)Phe-(D)Val-(D)Asn-(D)Tyr-(D)Arg-(D)Glu-(D)Glu-(D)Asn-(D)Thr-(D)Thr-(D)Phe-(D)Gly-(D)Cys-H 3) RETRO-INVERSO PEPTIDE of a Mimotope of Measles Virus (MV) Contained in the Measles Virus Fusion Protein (MVF).

Sequences of the parent L-peptide and of the double blocked L-peptide are shown below:

parent L-peptide of a mimotope of measles virus (SEQ ID NO:16):
H-Asn-Phe-Leu-Arg-Glu-Lys-Lys-Gln-Cys-OH double blocked L-peptide:
CH$_3$CO-Asn-Phe-Leu-Arg-Glu-Lys-Lys-Gln-Cys-NH$_2$ Sequence of the double blocked retro-inverso peptide:
CH$_3$CO-(D)Cys-(D)Gln-(D)Lys-(D)Lys-(D)Glu-(D)Arg-(D)Leu-(D)Phe-(D)Asn-NH$_2$ Sequence of the retro-inverso peptide
HO-(D)Cys-(D)Gln-(D)Lys-(D)Lys-(D)Glu-(D)Arg-(D)Leu-(D)Phe-(D)Asn-H 4) Retro-Inverso Peptide of a Cyclic Peptide of the Human Immunodeficiency Virus (HIV) Glycoprotein 41 (gp41) (Called "HIV gp41").

Sequences of the parent L-peptide and of the double blocked L-peptide are shown below:

HIV gp41parent L-peptide (SEQ ID NO:17):

H-Ile-TrP-Gly-Cys-Ser-Gly-Lys-Leu-Ile-Cys-Thr-Thr-Ala-OH
    |_____| corresponding to the residues 600–612 of the HIV gp41 peptide, double blocked HIV gp41 L-peptide:

CH$_3$CO-Ile-TrP-Gly-Cys-Ser-Gly-Lys-Leu-Ile-Cys-Thr-Thr-Ala-NH$_2$
        |_____|

Sequence of the double blocked retro-inverso HIV gp41 peptide:

CH₃CO-(D)Ala-(D)Thr-(D)Thr

-(D)Cys-(D)Ile-(D)Leu-(D)Lys-(D)Gly-(D)Ser-(D)Cys-(D)Gly-(D)Trp

-(D)Ile-NH₂

Sequence of the retro-inverso HIV gp41 peptide:

HO-(D)Ala-(D)Thr-(D)Thr

-(D)Cys-(D)Ile-(D)Leu-(D)Lys-(D)Gly-(D)Ser-(D)Cys-(D)Gly-(D)Trp

-(D)Ile-H

By way of illustration, in the field of vaccination the invention more particularly relates to the two totally retro-partly inverso peptides of the following formula:

HO-m(R,S)Leu-DGln-DArg-DAla-DVal-DArg-DX1-
DAla-DLeu-DSer-Gly-DX2-DAsp-Gly-DArg-
DVal-Gly-DSer-Gly-[Cys-NH₂]

X1=Ser or Phe
X2=Leu or Pro corresponding to the peptides [SL] and [FP] derived from the major antigenic determinant situated on protein VP1 of the aphthous fever virus, and corresponding to the following formulae:

[SL] [H-Cys]-Gly-Ser-Gly-Val-Arg-Gly-Asp-Ser-
Gly-Ser-Ala-Leu-Arg-Val-Ala-Arg-Gln-Leu-OH
(SEQ ID NO:1)

[FP] [H-Cys]-Gly-Ser-Gly-Val-Arg-Gly-Asp-Phe-
Gly-Ser-Ala-Pro-Arg-Val-Ala-Arg-Gln-Leu-OH
(SEQ ID NO:7)

The invention also more particularly relates to the totally retro-partly inverso cyclic peptide of the following formula

[CH₃-CO-Cys-Gly-Gly]-DX-DPhe-DAsp-DSer-Gly-
DPro-Gly-DArg-DLys-Ser

X=D-α, β-diaminopropionic acid, corresponding to residues 139–147 of site A of the haemagglutinin of the influenza virus (influenza strain X31), and corresponding to the following formula:

Ser-Lys-Arg-Gly-Pro-Gly-Ser-Asp-Phe-Asp-Gly-Gly-
Cys-NH₂ (SEQ ID NO:13)

The invention also relates to any pharmaceutical composition comprising the anti-immunoretroid antibodies according to the invention, optionally in combination with a physiologically acceptable vehicle.

This last category of pharmaceutical composition is more particularly intended for treatment of diseases associated with the presence in the organism of an individual of exogenous or endogenous proteins capable of being recognized by the anti-immunoretroid antibodies according to the invention, these latter acting as protective antibodies which neutralize the said exogenous or endogenous proteins.

The invention also relates to pharmaceutical compositions comprising, as the active substance, an antibody to a D peptide corresponding to a parent L peptide.

In one embodiment, the present invention provides an antibody or antibody fragment which binds with at least equal affinity to a peptide and an immunoretroid form of said peptide, said peptide being selected from the following.
C-terminal epitope of protein histone H3,
FP peptide from serotype A12 of foot-and-mouth disease virus,
FL peptide from serotype A12 of foot-and-mouth disease virus,
SL peptide from serotype A12 of foot-and-mouth disease virus;
internal domain 277–291 of 52 kD SSA/Ro protein,
internal domain 304–324 of 60 kD SSA/Ro protein,
internal domain 28–45 of histone H3,
site A of haemagglutinin of influenza virus,
peptide C18L of peptide HA91–108 of haemagglutinin of influenza virus,
peptide 9B1 of *Schistosoma mansoni*,
a mimotope of measles virus,
a cyclic peptide of human immunodeficiency virus glycoprotein 41,
a cytotoxic T-cell epitope of influenza virus matrix comprising epitope 56–68,
an auxiliary T epitope of tetanus toxin,
a poliovirus VP1 peptide, and
a peptide containing the third constant region of a mouse heavy chain IgG2a allopeptide γ2a[b].

The invention also relates to the use of antibody to a D peptide corresponding to a parent L peptide for the preparation of an immunogenic medicament, in particular for the preparation of a vaccine.

The invention also relates to the immunoretroids as defined above, which correspond to cytotoxic or auxiliary T epitopes, or also to peptides recognized by MHC molecules of type I or II which can be used either in the preparation of synthetic vaccines or in the prevention or treatment of autoimmune diseases.

As regards their use as vaccines, the invention more particularly relates to the partly retro-inverso immunoretroids of a cytotoxic T epitope (minimum epitope 56–68: M56–68) of the matrix of the influenza virus and an auxiliary T epitope (parent sequence 830–844: TT830–844) of the tetanus toxin, the sequences of which are shown below:

1/Sequence of M56–68:
H-Gly-Ile-Leu-Gly-Phe-Val-Phe-Thr-Leu-OH (SEQ ID NO:3)

Sequence of the retro analogue:
HO-m(R,S)Leu(D)-Thr(D)Phe-(D)Val-(D)Phe-(D)Phe-Gly-(D)Leu-gLle-Gly-H 2/Sequence of TT830–844 (SEQ ID NO:4):
H-Gln-Tyr-Ile-Lys-Ala-Asn-Ser-Lys-Phe-Ile-Gly-Ile-Thr-Glu-Leu-OH Sequence of the retro analogue
HO-m(R,S)Leu-(D)Thr-Gly-(D)Ile-(D)Phe(D)Lys-(D)Ser-(D)Asn-(D)Ala-(D)Lys-(D)Ile-gTyr-Gln-H The retro-inverso analogue of M56–68 interacts with MHC I molecules and is presented to cytotoxic T lymphocytes in order to induce a cytotoxic response. The retro-inverso analogue of TT830–844 interacts with the MHC II molecules and is presented to auxiliary T lymphocytes in order to stimulate proliferation of T cells.

As regards the use of immunoretroids in the context of the preparation of medicaments intended for treatment of autoimmune diseases, it is appropriate to note that the pathogenesis of many autoimmune diseases involves presentation of autoantigens (bonded to MHC molecules) to the receptor of autoreactive T cells (TCR), which have in one way or another escaped from the tolerance process of the being. Furthermore, the development of new strategies to modulate the response of autoreactive T cells could lead to therapeutic approaches which can be used for treatment of certain autoimmune diseases.

Certain autoimmune diseases are associated with specific MHC I or II alleles. The use of blocking peptides which are capable of interaction with a given MHC molecule (for example an MHC molecule of class II associated with a particular autoimmune disease) but which cannot activate the pathogenic T cell response is thus attractive. However, the rapid degradation of the peptides studied in biological media renders their use difficult. In this case, the immunoretroids would be very advantageous because of their stability.

The phenomenon of TCR antagonism by peptide analogues to T epitopes has recently been demonstrated and the use of specific TCR antagonists has been described (De Magistris, M. T., Alexander, J., Coggeshall, M., Altmon, A., Gaeta F. C. A., Grey, H. M. and Sette, A. (1992), Cell 68: 625). These peptides are capable of inhibiting the proliferation of T cells induced by an antigen. Such antagonist peptides are obtained by substitution of one amino acid among the residues of the antigen peptide in contact with the T cell, or by incorporation of residues in contact with the TCR into a sequence of poly-alanines. The present invention relates precisely to the use of immunoretroids corresponding to antagonist peptides of TCR to obtain medicaments intended for treatment of autoimmune diseases such as those described above.

By way of illustration in the field of autoimmune diseases (immunomodulation) two specific retro-inverso immunoretroids (the sequences of which are shown below) have been analyzed for their antigenic and in vivo immunogenic properties in the major histocompatibility complex (MHC) II and T-helper cell response context.

These two specific immunoretroids are those corresponding to the following T helper epitope:
   the parent L-peptide 103–115 of poliovirus VP1 which is involved in the production of antibodies that neutralize the infectivity of the virus, the parent L-peptide 435–446 from the third constant region of mouse heavy chain IgG2a allopeptide $\gamma 2a^b$ which mimics a corneal antigen implicated in autoimmune keratitis.

Amino acid sequences of double blocked L-peptide 103–115 of poliovirus type 1 VP1, and of its retro-inverso analogue are respectively:

Sequence 103–115 of poliovirus type 1 VP1:

double blocked L-peptide:

$CH_3$CO-Lys-Leu-Phe-AI a-Val-Trp-Lys-Ile-Thr-Tyr-Lys-Asp-Thr-$NH_2$ double blocked RI-peptide:

$CH_3$CO-(D)Thr-(D)Asp-(D)Lys-(D)Tyr-(D)Thr-(D)Ile-(D)Lys-(D)Trp-(D)Val-(D)Ala-(D)Phe-(D)Leu-(D)Lys-$NH_2$

Amino acid sequences of double blocked L-peptide 435–446 of the $\gamma 2a^b$ allotype and of its retro-inverso analogue are respectively:

Sequence 435–446(C) of the $\gamma 2a^b$ allotype$^b$:

double blocked L-peptide:

$CH_3$CO-Tyr-Phe-Met-Tyr-Ser-Lys-Leu-Arg-Val-Gln-Lys-Ser-Cys-$NH_2$ double blocked RI-peptide:

$CH_3$CO-(D)Cys-(D)Ser-(D)Lys-(D)Gln-(D)Val-(D)Arg-(D)Leu-(D)Lys-(D)Ser-(D)Tyr-(D)Met-(D)Phe-(D)Tyr-$NH_2$

The immunoretroids can be prepared as indicated below:

By way of illustration, general methods for the synthesis of totally or partly retro-inverso or retro peptides, with or without modification of the N- and C-terminal ends with respect to the ends of the parent peptides, are indicated below.

The process for the synthesis of peptides in which all the —CO—NH— bonds are replaced by —NH—CO— bonds, in comparison with the parent peptides, without modification of the ends is carried out by connecting between them the various aminoacyl residues which make up the parent peptide in the reverse direction to that indicated for the parent peptide. Thus, if the parent peptide is represented by a sequence of the type H-AA1-AA2- . . . -AAn-1AAn-OH, the corresponding retro analogue synthesized according to the conventional techniques of peptide synthesis in the liquid or solid phase will have the following formula:

H-AAn-AAn-1 . . . -AA2-AA1-OH

By way of illustration, the method for synthesis in the liquid phase comprises successive condensation, two by two, of the aminoacyls in the required order or condensation of the aminoacyls and fragments which have been formed beforehand and already comprise several aminoacyls in the appropriate order, or several fragments previously prepared in this way, it being understood that it will be necessary to protect all the reactive functions carried by these aminoacyls or fragments beforehand, with the exception of the amine functions of the one and carboxyl functions of the other, or vice versa, which should usually involved in the formation of peptide bonds, in particular after activation of the carboxyl function, in accordance with the methods well-known in the synthesis of peptides.

For example, it would be possible to use protective groups of the urethane type (Boc, Fmoc, benzyloxycarbonyl or allyloxycarbonyl) to protect the N-terminal ends of the amino acids and groupings of the ester type (methyl, ethyl, benzyl, tert-butyl, allyl or benzhydrylglycolamide) to protect the C-terminal ends of the amino acids.

Such a synthesis can be carried out by first condensing the aminoacyl residue AA1, the COOH function of which is protected, with the aminoacyl residue AA2, the $NH_2$ function of which is protected. The amine function of the AA2 residue in the AA2-AA1 fragment thus obtained is then deprotected, for subsequent condensation of the said fragment with the aminoacyl residue AA3, the amine function of which is protected. The preceding stages are repeated for as many times as there are aminoacyl residues to be introduced into the chain of the retro analogues to be synthesized.

According to another preferred technique of the invention, that described by R. M. Merrifield in the article entitled "Solid phase peptide synthesis" (J. Am. Chem. Soc. (1963), 85, 2149–2154) is used.

To prepare a peptide chain by the Merrifield process, a highly porous polymeric resin on which the first C-terminal amino acid (in this case AA1-OH) of the chain is fixed is used. This amino acid is fixed on the resin by the intermediary of its carboxyl group, and its amine function is protected, for example by the t-butyloxycarbonyl group.

When the first C-terminal amino acid is fixed on the resin in this way, the protective group of the amine function is removed by washing the resin with an acid.

The amino acids which will make up the peptide chain are thus fixed, one after the other, onto the amino group, deprotected beforehand, of the portion of the peptide chain already formed, which is attached to the resin.

When all the desired peptide chain has been formed, the protective groups of the various amino acids which make up the peptide chain are removed and the peptide is detached from the resin, for example with the aid of hydrofluoric acid.

The preparation of cyclic retro peptides is advantageously carried out in accordance with the method of A. Kates et al., Tetrahedron Lett., 34, 4709, (1993).

If all the starting aminoacyl residues AA1 to AAn used for synthesis of the retro analogues have the same chirality as these same aminoacyl residues which make up the parent peptide, the retro analogue obtained will be a totally retro peptide.

Conversely, if all of these residues AA1 to AAn are of opposite chirality to that of these same residues in the parent peptide, the retro analogue obtained will then be a retro-inverso peptide.

If one or more of, but not all, these residues are of opposite chirality to that of these same residues in the parent peptide, the retro analogue obtained will then be a totally retro-partly inverso peptide.

The preparation of partly retro peptides or partly retro-inverso peptides and also of totally retro or retro-inverso peptides with modification of the ends is advantageously carried out with the aid of the conventional technique using gem-diaminoalkyl residues and substituted C-2 derivatives of malonic acid, described in particular in the article by Pallai and Goodman (Pallai, P. V., and Goodman, M., (1982), J. Chem. Soc. Chem. Commun., 280–281), and in the chapter by Cope et al. ((1957), Org. React., 9, 107) respectively.

In this last reference, the preparation of substituted C-2 derivatives of malonic acid is carried out by alkylation of a diester of malonic acid.

The substituted C-2 monoester of malonic acid can also be obtained by alcoholysis of derivatives of Meldrum acid (Junek et al., (1976), Synthesis, 333–334; Chorev et al., (1983); J. Med. Chem. 26, 129–135), these derivatives themselves being obtained by reductive alkylation of Meldrum acid in accordance with the method described by Hrubowchak, D. M., and Smith, F. X. (1983), Tetrahedron Lett., (24), 4951–4954).

As regards the synthesis of gem-diaminoalkyl derivatives described by Pallai and Goodman, the optically pure mono-N-acylated gem-diaminoalkyl residues are obtained from N-protected amide peptides or from carboxamide aminoacyl derivatives via a Hoffman rearrangement using a moderately oxidizing reagent: iodobenzene bis(trifluoroacetate), called IBTFA or TIB. Furthermore, this method can be used in the solid phase in accordance with the technique described by Pessi et al. (1983), J. Chem. Commun., 195–197.

By way of illustration, the preparation of a retro peptide of the formula:

. . . —NH—CH(R1)—CO—NH—CH(R2)—CO—
        NH—CH(R3)—NH—CO—CH(R4)—CO—
        NH—CH(R5)—CO—NH—CH(R6)—CO— . . .

can be carried out by condensation of the amino acid derivative P—HN—CH(R2)—COOH, P representing a protective grouping of the urethane type, with the carboxamide derivative H$_2$N—CH(R3)—CO—NH$_2$, followed by treatment of the amide dipeptide obtained with IBTFA, which leads to a mono-N-acylated gem-diaminoalkyl residue of the formula P—HN—CH(R2)—CO—NH—CH(R3)—NH$_2$, and then condensation of this derivative with a C2-substituted monoester of malonic acid of the formula HOOC—CH(R4)—COOR, —R representing a protective grouping such as —CH$_3$, —CH$_2$CH$_3$, —C(CH$_3$)$_3$ or benzyl, which leads to a fragment of the formula:

P—HN—CH(R2)—CO—NH—CH(R3)—NH—CO—
    CH(R4)—COOR, followed by selective deprotection of the R grouping, and condensation of the fragment of which the C-terminal acid function is deprotected in this way with a fragment of the formula H$_2$N—CH(R5)—CO—NH—CH(R6)—CO . . . , obtained by condensation of an amino acid derivative P'—NH—CH(R5)—COOH, P' representing a protection of the urethane type, and a fragment of the formula H$_2$N—CH(R6)—CO . . . , the C-terminal end of which is protected, and selective deprotection of P', which leads to a fragment of the formula:

P—HN—CH(R2)—CO—NH—CH(R3)—NH—CO—
    CH(R4)—CO—NH—CH(R5)—CO—NH—CH(R6)—
    CO— . . . , followed by selective deprotection of the protective group P, and condensation of the fragment of which the N-terminal amine function is deprotected in this way with a fragment or a derivative of an amino acid of the formula . . . —NH—CH(R$_1$)—COOH, the N-terminal end of which is protected, which leads to the desired derivative of the formula:

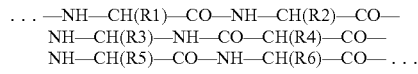

containing a gem-diaminoalkyl residue carrying R3 and a derivative of malonic acid carrying R4.

If the production of several successive —NH—CO— bonds within the same partly retro peptide or retro-inverso peptide is desired, it is sufficient to incorporate one or more aminoacyl residue(s) of identical or opposite chirality to this (these) aminoacyl residue(s) in the parent peptide, between a gem-diaminoalkyl residue and a derivative of malonic acid as described above, by the conventional techniques in peptide synthesis.

By way of example, the fragment of the formula:

P—HN—CH(R2)—CO—NH—CH(R3)—NH$_2$, preparation of which by treatment of the amide dipeptide with IBTFA has been described above, can be condensed with an aminoacyl derivative of the formula P'—HN—CH(R4)—COOH, which leads to the preparation of a fragment of the formula P—HN—CH(R2)—CO—NH—CH(R3)—NH—CO—CH(R4)—NH—P', which, after selective deprotection of the P' grouping, can be condensed with a C2-substituted monoester of malonic acid of the formula HOOC—CH(R5)—COOR, —R representing a protective grouping such as —CH$_3$, —CH$_2$CH$_3$, —C(CH$_3$)$_3$, —CH$_2$—CH=CH$_2$ or benzyl, which leads to the fragment of the formula

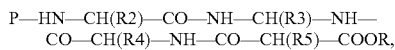

which, after selective deprotection of the R grouping and condensation of the fragment, of which the C-terminal acid function is deprotected in this way, with a fragment of the formula H$_2$N—CH(R6)—CO— . . . , leads to the fragment of the formula: P—HN—CH(R2)—CO—NH—CH(R3)—NH—CO—CH(R4)—NH—CO—CH(R5)—CO—NH—CH(R6)—CO— . . . , which, after selective deprotection of the group P, can be condensed with the fragment ... —NH—CH(R1)—COOH, the N-terminal end of which is protected, which leads to the derivative of the formula ... —NH—CH(R1)—CO—HN—CH(R2)—CO—NH—CH(R3)—NH—CO—CH(R4)—NH—CO—CH(R5)—CO—NH—CH(R6)—CO— ...

As above, the preparations of partly retro or retro-inverso peptides by the method described above is determined by the choice of the chirality of the aminoacyl residues which will be capable of being bonded to at least one of their neighbours by a bond of the —NH—CO— type in the analogue obtained.

The invention also relates to the processes for the preparation of totally retro, totally retro-inverso or totally retro-partly inverso immunoretroids as described above, the N- and C-terminal ends of which are modified to mimic further the ends of the parent peptide.

In fact, as we have seen in the preceding synthesis examples starting from the parent peptide represented by the formula:

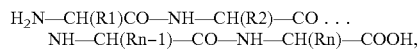
NH—CH(Rn-1)—CO—NH—CH(Rn)—COOH, the retro peptide obtained after reversal of all the —CO—NH— bonds is represented by the formula:

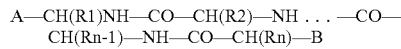
CH(Rn-1)—NH—CO—CH(Rn)—B in which A and B represent, respectively, HOOC— and —NH$_2$, or any other group initially situated in the N- or C-terminal position of the parent peptide if the analogue is constructed without modification of its ends.

However, it is possible to modify the N- and C-terminal groups of the retro analogue to mimic the N- and C-terminal ends of the parent peptide.

In particular, it is possible to obtain retro analogues of the formula indicated above, in which A represents H—, H$_2$N—, P—HN—, RR'N—, H$_2$NCO—, RR'NCO— or RCO— and B represents —H, —COOH, —COOR, —CONH$_2$, —CONRR' or —NHCOR, R, R' and P being defined as indicated with regard to the formula (II) above.

By way of illustration, the preparation of retro analogues for which A represents H$_2$N— and B represents —COOH can be carried out by incorporating a gem-diaminoalkyl derivative (H$_2$N—CH(R1)—NH—) to mimic the N-terminal end of the parent peptide and by incorporating a C2-substituted derivative of malonic acid (—CO—CH(Rn)—COOH) to mimic the C-terminal end of the parent peptide, by the methods indicated above.

The preparation of retro analogues in which A represents H$_2$NCO— and B represents —NHCOR, R corresponding to the definition given above, can be carried out by amidation of the COOH of the N-protected amino acid HOOC—CH(R1)—NH—P and by acylation of the N-terminal end; (by way of example, an acetylation is carried out with acetic anhydride in the presence of DIEA [DIEA=diisopropylethylamine], which gives for B: —NHCOCH$_3$).

By combining the various techniques described above for introduction of groups A and B, it is possible to obtain all possible combinations of the groups A and B at the ends of the analogues of the invention.

In this respect, particularly preferred retro analogues in the context of the invention are those for which A represents H$_2$NCO— and B represents —COOH, obtained by introducing a carboxamide termination into the C-terminal of the retro analogue, and by introducing a C-2-substituted derivative of malonic acid at the N-terminal end of the retro analogue, by the techniques described above.

It is appropriate to state that the malonic acid derivatives are incorporated in the racemic form (written -m(R,S)AAi-), and if a chiral centre is to be maintained at the level of this malonate in the peptide, it is necessary to purify the mixture of the two diastereoisomers thus obtained at the end of the synthesis, in particular by liquid phase chromatography.

The invention will be illustrated further with the aid of the examples which follow for the preparation of immunoretroids as described above, and also with the aid of the demonstration of their antigenic and immunogenic properties.

LEGENDS TO THE FIGURES

FIG. 1: This relates to the diagrammatic representation of the natural peptide L-IRGERA (SEQ ID NO:18) and of peptide analogues.

FIG. 2: This relates to the ELISA test of the immune response to the four peptide analogues injected as peptides coupled to SUV in BALB/c mice. The antisera are diluted 1:500 and tested with homologous peptides (A and B) or with H3 (parent protein) (C, D). The anti-murine IgG conjugate (H+L) revealing murine antibodies of isotypes IgG1, IgG2a and IgG2b (blank symbols) and the anti-murine IgG3 conjugate (solid symbols) are both diluted 1:5,000. The results represent the mean values of the absorbance obtained in each group of two mice immunized with the peptide L-IRGERA (SEQ ID NO:18) (Δ, ▲), the retro-inverso peptide (○,●), the D peptide (□, ■) and the retro peptide (◇, ◆). The arrows indicate the immunization plan for the mice.

FIG. 3: This relates to the resistance to trypsin of the four peptide analogues. The trypsin is immobilized covalently on nylon spheres. The digestion mixture incubated for various times at 25° C. is first incubated with the antibody MAb 11×2 (4 µg/ml) and is then injected with the L peptide immobilized on the Biacore activated matrix of dextran. The results are expressed as a function of the percentage inhibition of the bonding of MAb 11×2 to the L peptide immobilized by competitor peptides subjected to trypsin. The bonding of MAb 11×2 to the L peptide in the absence of inhibitor peptide corresponds to 800 RU. In the presence of a non-digested peptide, the bonding of MAb 11×2 to the L peptide is 220 RU, 240 RU, 260 RU and 250 RU respectively for the L peptide, the retro-inverso peptide, the D peptide and the retro peptide.

FIG. 4: This relates to the synthesis of the retro-inverso analogue of the C-terminal epitope of the protein H3: IRGERA (SEQ ID NO:18).

Sequence of the parent peptide (SEQ ID NO:5):
[H Cys-Gly-Gly]-Ile-Arg-Gly-Glu-Arg-Ala-OH
Sequence of the retro analogue:
HO-m(R,S)Ala-DArg-DGlu-Gly-DArg-DIle-[Gly-Gly-Cys-NH$_2$]
In this figure:
a=MBHA resin; b=BOP, HOBT, DIEA/DMF; c=TFA; d=HF
Abbreviations: MBHA=4-methylbenzhydrylamine, HOBT=hydroxybenzotriazole, TFA=trifluoroacetic acid, HF=hydrofluoric acid, BOP=benzotriazolyl-oxy-tris(dimethylamino)phosphonium hexafluophosphate, DMF=dimethylformamide, DIEA=diisopropylethylamine.

FIG. 5: This relates to the synthesis, in solution, of a retro-inverso analogue of the T epitope (56–68) of the matrix of influenza.

Sequence of the parent peptide (SEQ ID NO:3):

H--Ile-Leu-Gly-Phe-Val-Phe-Thr-Leu-OH

Sequence of the retro-inverso analogue:

HO-m(R,S)Leu-(D)Thr-(D)Phe-(D)Val-(D)Phe-Gly-(D)Leu-gIle-Gly-H

In this figure, a=BOP, HOBT, DIEA/DMF, b=IBTFA, CH3CN/H2 O (1:1), c=TFA, d=NaOH (1N)/MeOH, g=gem-diaminoalkyl FIG. 6: ELISA reactivity of serum samples originating from patients suffering from DLE and SS with the parent peptide and the analogue RIb 277–291 of Ro52. The sera of the patients are diluted to 1:1,000. Only the antibody activity of the sub-class IgG is measured. The median values of the optical density are indicated. The broken line represents the upper limit of the normal population corresponding to the mean value of the optical density of 20 normal human sera+2 SD (standard deviation) (0.30 OD units).

FIG. 7: ELISA reactivity of two sera of patients suffering from DLE (A, B) with the parent peptide L 277–291 of Ro52 (•—•) and the two diastereoisomers RIa (□—□) and RIb (○—○). The sera of the patients are diluted to 1:1,000 and allowed to react at various concentrations of peptide.

FIG. 8: Schematic structure of the L peptide 304–324 of Ro60. ELISA reaction of the sera of 20 patients suffering from DLE and SS with analogues of the peptide 304–324 of Ro60. The sera of the patients are diluted to 1:1,000. Only the IgG activity is measured. The median values of the optical density are indicated. The broken lines represent the upper limit of the normal population corresponding to the mean value of the optical density of 20 normal human sera+2 SD (standard deviation) (0.30 OD units).

FIG. 9: Immuno-enzymatic test on the membrane ("dot immunoassay") of the L peptide 304–324 of Ro60 and peptide analogues incubated with $^\gamma$Zn. A control peptide which does not contain the bonding domain of zinc (peptide 56–77 of U1-RNP polypeptide A, Barakat et al., Clin. Exp. Immunol., 86: 71–78, 1991) is used as the control (band 1). Increasing amounts of 5 peptide analogues and of the control peptide are deposited on the nitrocellulose sheets (0.22 µm); the peptides are incubated with $^{65}$Zn as described previously (Mazen, A., Menissier-de Murcia, J., Molinete, M., Simonin, F., Gradwohl, G., Poirier, G., and de Murcia, G. (1989), Poly(ADP-ribose)polymerase: a novel finger protein. Nucl. Acids. Res., 17: 4689–4698; Muller, S., Briand, J. P., Barakat, S., Lagueux, J., Poirier, G. G., De Murcia, G., and Isenberg, D. D. (1994) Autoantibodies reacting with poly (ADP-ribose) and with a zinc-finger functional domain of poly(ADP-ribose) polymerase involved in the recognition of damaged DNA. Clin. Immunol. Immunopathol., 73: 187–196). The nitrocellulose sheets are autoradiographed for 5 hours (A) and 14 hours (B) at −70°. Bands 2,2': L peptide: bands 3,3': RI peptide; bands 4,4': D-allo-Ile RI peptide; band 5: blocked L peptide; bands 6, 6': blocked RI peptide. The results originate from two independent experiments (A and B).

Figure 12:
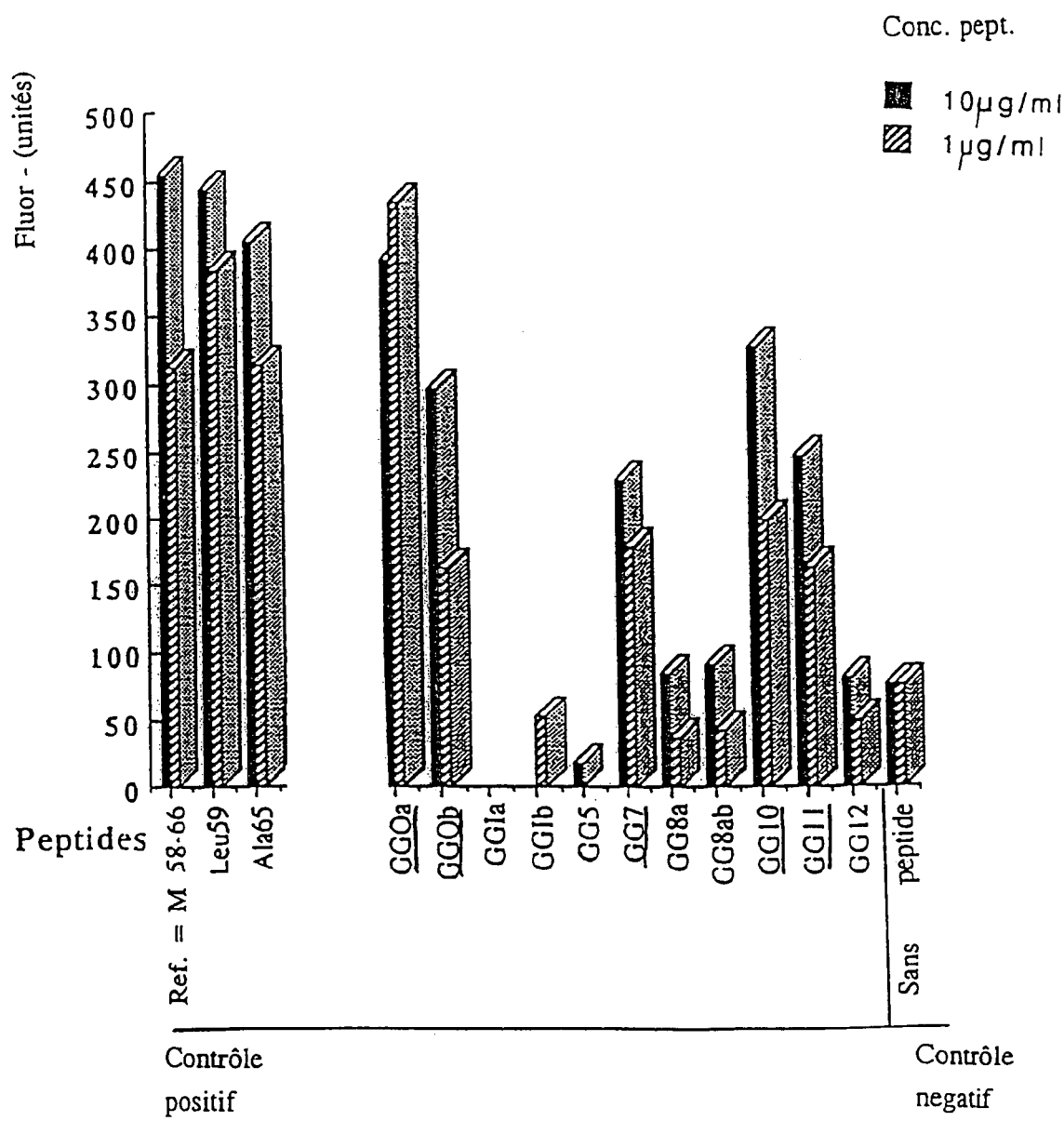

FIG. 12 summarizes the results of fixing to the molecule HLA-A2. The peptides are along the abscissa and the fluorescence units along the ordinates. The solid bars correspond to peptide concentrations of 10 µg/ml and the hatched bars correspond to peptide concentrations of 1 µg/ml.

Figure 13:
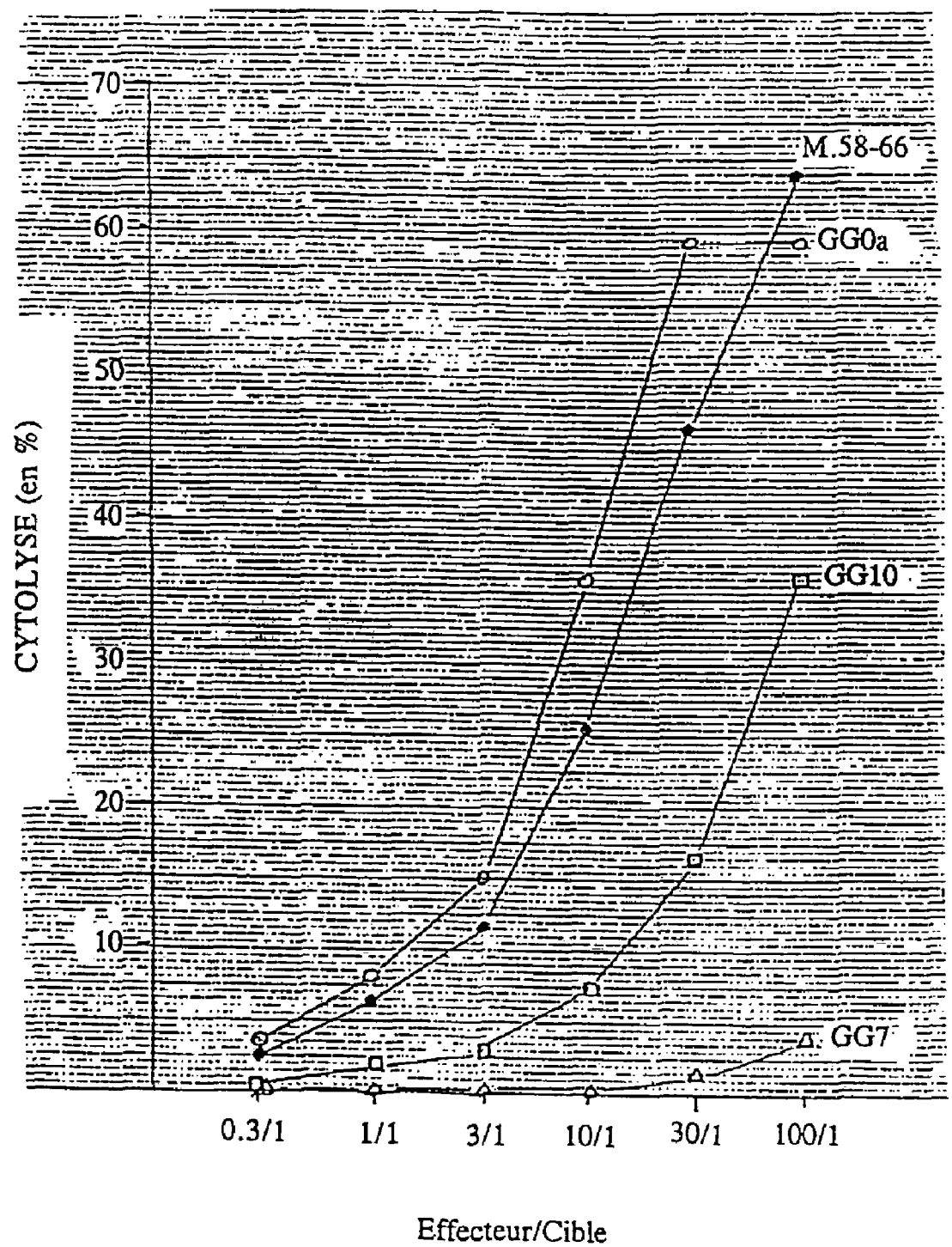

FIG. 13 corresponds to measurement of the cytolysis (expressed in %) (on the ordinates) as a function of the ratio of the number of effector/target cells (on the abscissa) in the context of the test described in Martinon et al., Eur. J. Immunol. 1990, 20, 2071–2176. The curve with triangles corresponds to peptide GG7, that with squares to peptide GG10, that with solid circles to peptide M58–66 and that with blank circles to peptide GG0a.

Figure 14:
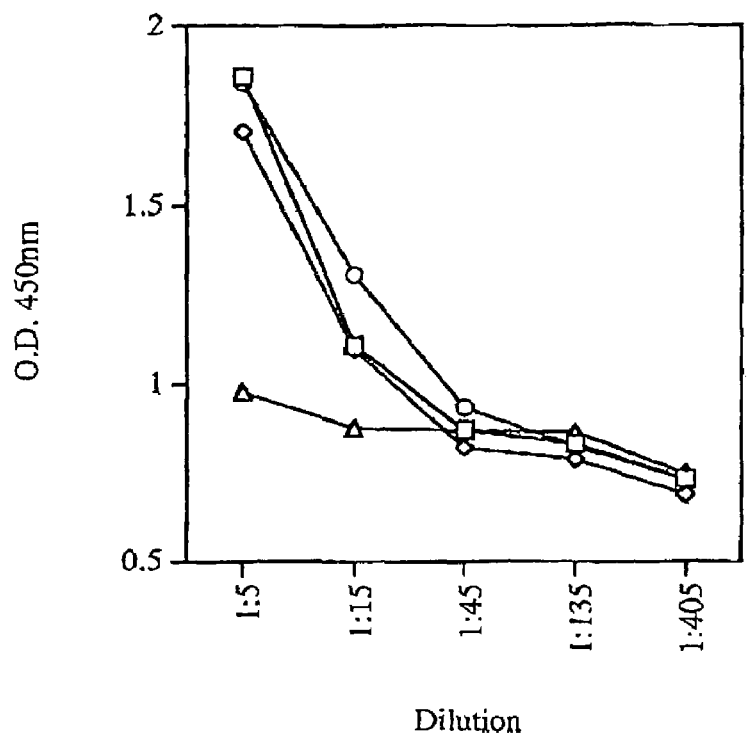

FIG. 14: ELISA reactivity of anti-virus serum raised in rabbit with the following peptides the parent L-peptide C18L (□), the double blocked L-peptide *C18L* (○), the double blocked retro-inverso peptide (◇).

NRS: normal rabbit serum (Δ)

The serum dilutions are indicated on abscissa axis. Y-axis represents the ELISA reactivity measured at the optical density of 450 nm.

Figure 15:
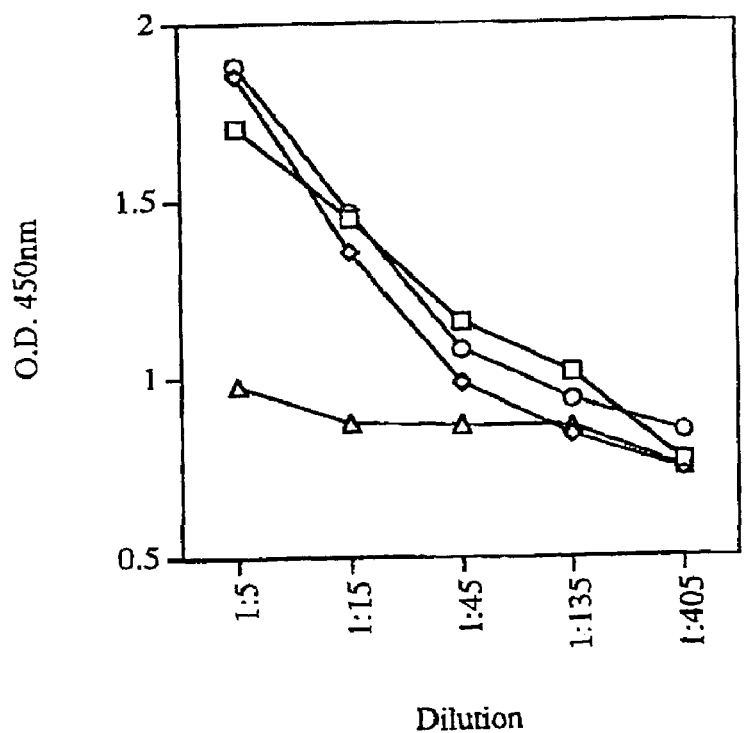

FIG. 15: ELISA reactivity of serum against the 91–108 sequence expressed at the surface of Salmonella flagellin with the following peptides:

the parent L-peptide C18L (□), the double blocked L-peptide *C18L* (○), the double blocked retro-inverso peptide (◇).

NRS: normal rabbit serum (Δ)

The serum dilutions are indicated on abscissa axis. Y-axis represents the ELISA reactivity measured at the optical density of 450 nm.

Figure 16:
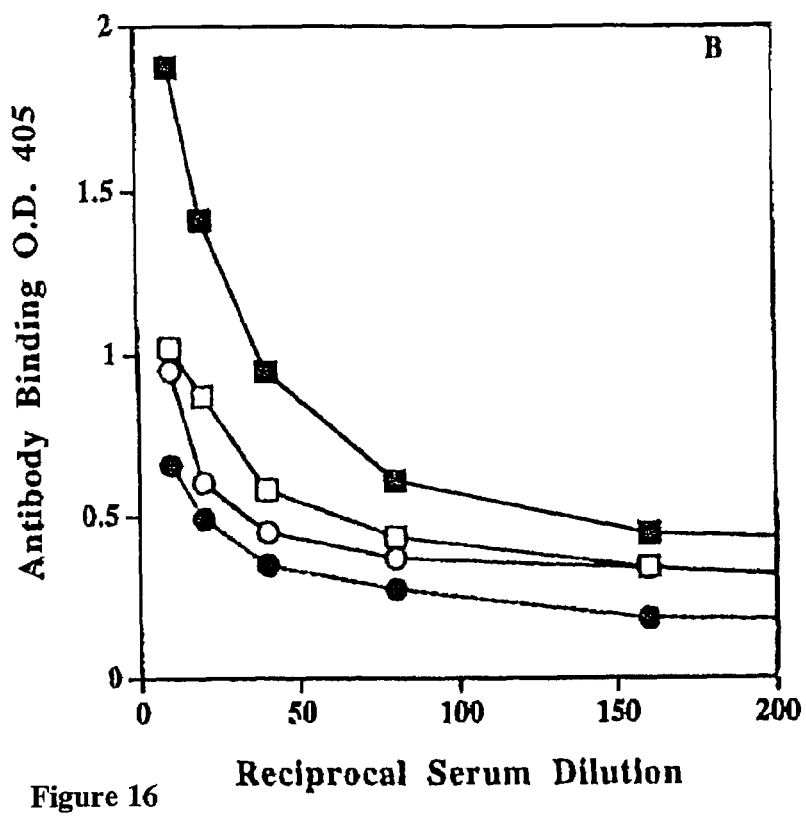

FIG. 16: ELISA reactivity of the following antibodies:

normal mouse serum (NMS) (•), infected mouse serum (○), anti L-peptide 9B1 mouse serum (□), anti double blocked L-peptide 9B1 serum (■), with the antigenic retro-inverso 9B1 peptide.

The reciprocal serum dilutions are indicated on abscissa axis. Y-axis represents the Antibody Binding measured at the optical density of 405 nm.

Figure 17:
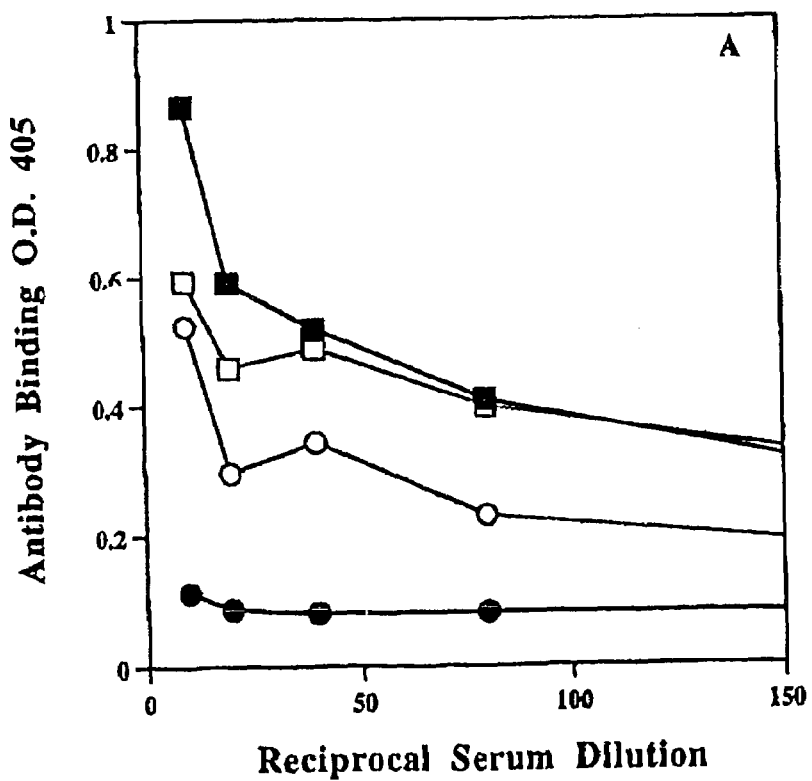

FIG. 17: ELISA reactivity of the following antibodies normal mouse serum (NMS) (•), infected mouse serum (○), anti L-peptide 9B1 mouse serum (□)

anti double blocked L-peptide 9B1 serum (■), with the antigenic double blocked 9B1 peptide.

The reciprocal serum dilutions are indicated on abscissa axis. Y-axis represents the Antibody Binding measured at the optical density of 405 nm.

Figure 18:
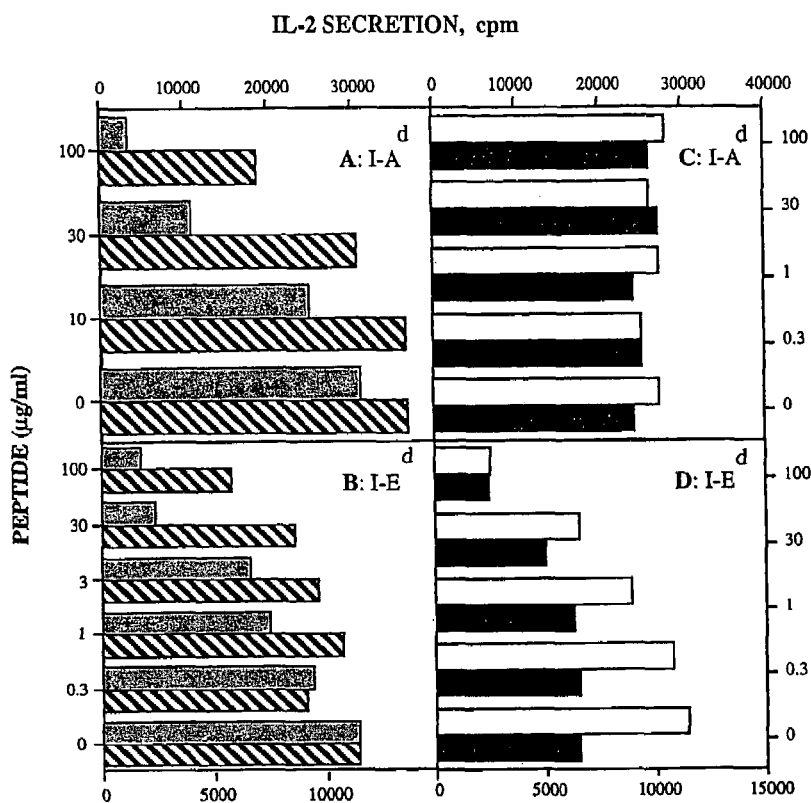

FIG. 18. Binding of peptide analogues to I-A$^d$ and I-E$^d$ class II molecules.

Mouse L fibroblasts transfected by either I-A$^d$ (FIGS. 18A and 18C) or I-E$^d$ (FIGS. 18B and 18D) were first incubated with various concentrations (0.3–100 µg/ml) of γ2a$^b$ (FIGS. 18A and 18B) and poliovirus (FIGS. 18C and 18D) peptides. After 15 to 30 min, peptide 12–26 of cI (1 µg/ml) and T-cell hybridomas which recognized this peptide in the I-A$^d$ (FIG. 18A, 18C) or I-E$^d$ (FIG. 18B, 18D) context were added to the cultures. After 24 h, the secretion of IL-2 was measured using CTL-L cells. Peptides tested for binding are the folowing: (shaded box), L-peptide 435–446 of γ2a$^b$; (hatched box), retro-inverso peptide 435–446 of γ2a$^b$;☐, L-peptide 103–115 of poliovirus VP1; ■, retro-inverso peptide 103–115 of poliovirus VP1.

Figure 19:
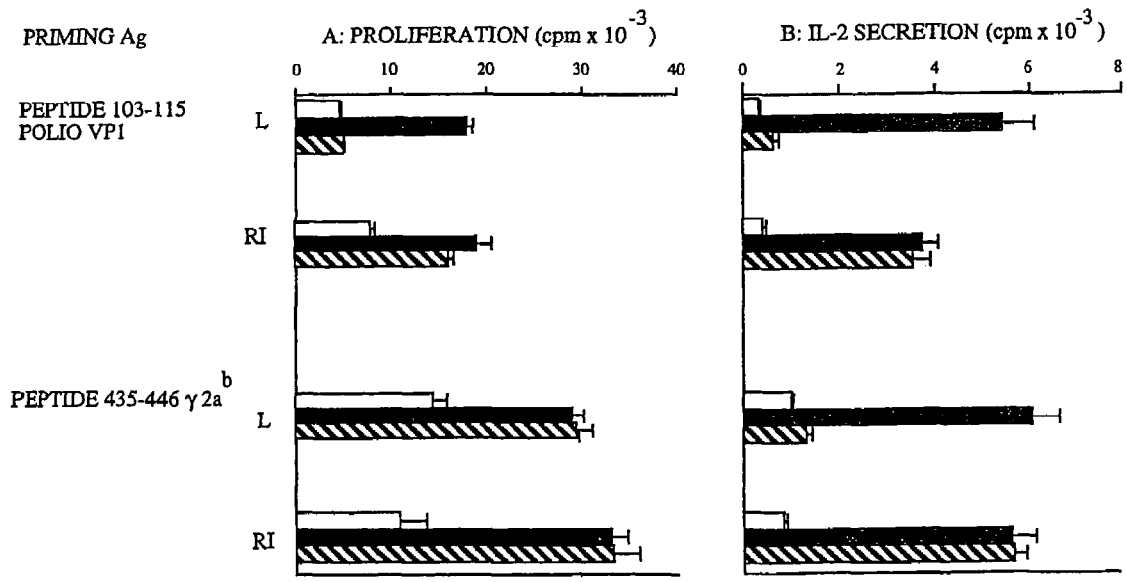

FIG. 19. Specificity of in vitro T-helper (Th) cell response of peptide-primed T lymphocytes from BALB/c immunized against peptides 103–115 of poliovirus type 1 VP1 and 435–446 of the γ2a$^b$ allotype, and retro-inverso analogues.

Two BALB/c mice were immunized per peptide and per experiment. The results shown correspond to one representative experiment of two to four performed. The proliferative response (FIG. 19A) and IL-2 secretion (FIG. 19B) of peptide-primed T-lymphocytes were measured in vitro in the absence of peptide (control; ☐) or in the presence of 100 μg/ml of L- (■) and retro-inverso (RI) (hatched box) peptides. The maximal response of T-cells from animals immunized with L- and retro-inverso (RI) peptides was measured by testing either the proliferation or the IL-2 secretion in the presence of antibodies to mouse CD3 and Con A (concanavalin) (not shown in the figure). The maximal IL-2 secretion was measured using CTL-L cells in the presence of Con A; the values were 10 990 counts per minute (cpm) and 5 570 cpm for T-cells primed in vivo with the L- and retro-inverso polio peptides respectively, and 21 565 cpm and 26 445 cpm for T-cells primed in vivo with the L- and retro-inverso γ2a$^b$ peptides, respectively.

Figure 20:
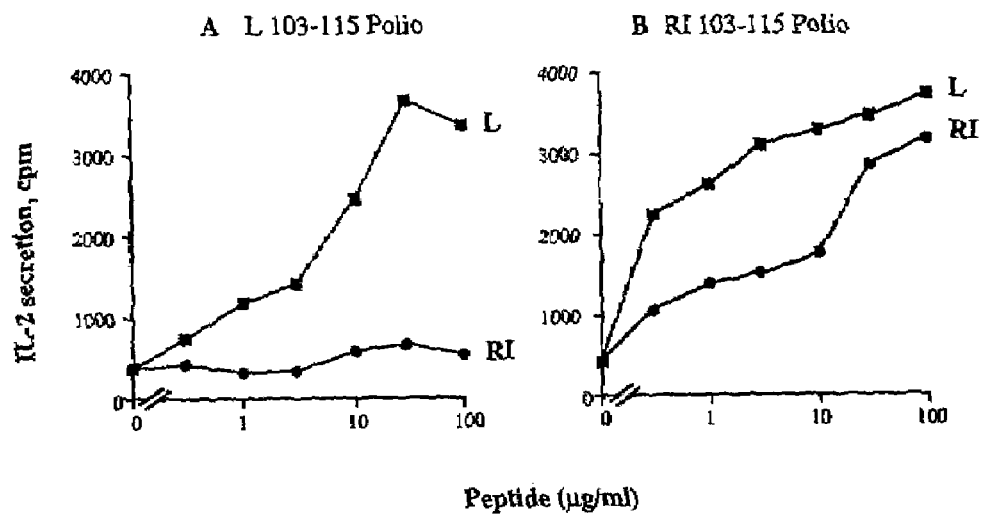

FIG. 20. T-cell proliferative responses of L- and retro-inverso poliovirus peptide-primed lymph node cells.

BALB/c mice were immunized with 100 μg of the parent (A) and retro-inverso (B) poliovirus peptides 103–115. Ten days later, lymph node cells were stimulated in vitro with various concentrations (0.03–100 μg/ml) of L- and retro-inverso peptides. Secretion of IL-2 was measured by adding 24 h-culture supernatants to IL-2 dependent CTL-L cells. After 24 h, the cultures were pulsed during 6 h with tritiated thymidine. The results are expressed in cpm corresponding to DNA-incorporated radioactivity. The maximum response in the presence of ConA corresponded to 15 000 cpm. Peptides used to stimulate lymph node cells in vitro were the L-peptide (■) and the retro-inverso analogue (•).

Figure 21:
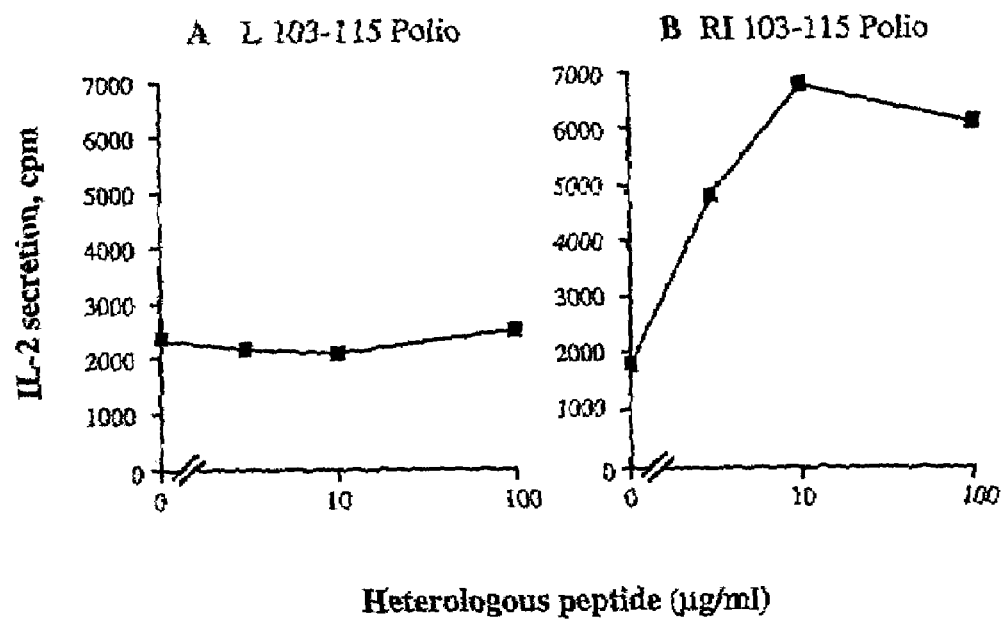

FIG. 21. Cross-recognition of polio peptides by TCR.

Lymph node cells used as APCs (antigen-presenting cell) from mice immunized against the parent peptide (A) or the retro-inverso analogue (B) were prepulsed with respective homologous peptides for 15 min (suboptimal conditions). After washing, they were incubated with various concentrations (0, 10, 30 and 100 μg/ml) of respective heterologous peptides for 15 min. After washing and addition of mitomycin C for 20 min, cells were incubated with respective lymph node cells (used as responder T-cells) for 24 h. IL-2 secretion was measured using CTL-L cells.

Figure 22:
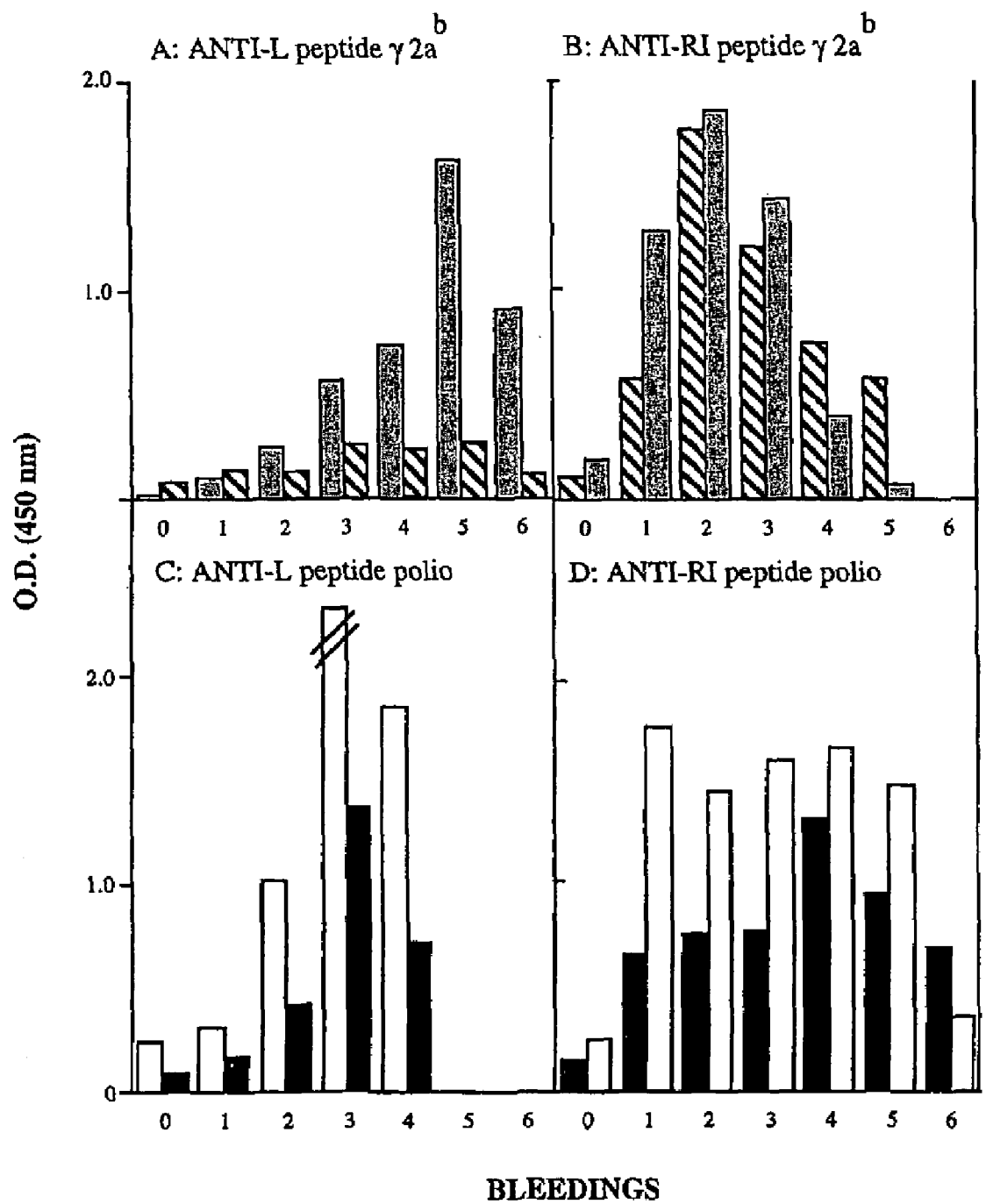

FIG. 22. Test, using ELISA, of the antibody response to the γ2a$^b$ and polio L- and retro-inverso peptides injected as carrier protein (ovalbumin (OVA) or methylated BSA)-associated peptide in BALB/c mice.

Mice received three injections on days 0, 15 and 30 and were bled on days 0 (prebleeding), 20 and 35 (bleedings 1 and 2), and then every two weeks until day 80 (bleedings 3–6). The results of one of two immunized mice are shown. Antisera were diluted 1/500 and allowed to react with homologous and heterologous peptides. Only IgG activity was measured. Peptides used as test antigen (Ag) in the ELISA were: (shaded box), L-peptide 435–446 of γ2a$^b$; (hatched box), retro-inverso peptide 435–446 of γ2a$^b$; ☐, L-peptide 103–115 of poliovirus VP1; ■, retro-inverso peptide 103–115 of poliovirus VP1. OD, optical density.

EXAMPLE 1

Materials and Methods

Histone H3 and Peptides

Histone H3 of the erythrocyte of the chicken is isolated and purified as described previously (Van der Westhuyzen, D. R., & Von Holt, C. (1971), FEBS Lett., 14, 333–337).

Three analogues of model peptides of the IRGERA (SEQ ID NO:18) sequence corresponding to COOH-terminal residues 130 to 135 of the histone H3 are prepared. The preparation and purification of the L- and D-IRGERA (SEQ ID NO:18) peptides have been described previously (Benkirane et al., (1993), J. Biol. Chem., 268, 26279–26285). The two new analogues, the retro-inverso peptides and the retro peptides, are synthesized in the same way as the L and D peptides by the solid phase method on a multi-channel peptide synthesizer (Neimark, J. & Briand, J. P., (1993), Peptide Res., 6, 219–228). The retro-inverso and retro isomers modified at the terminal ends are linked, using the protective group Boc, on a p-methylbenzhydrylamine resin (Applied Biosystem, Roissy, France). Linkage of the protected peptide chain is effected on a scale of 200 μmol using the in situ neutralization protocol described previously (Neimark, J. & Briand, J. P., (1993), Peptide Res., 6, 219–228). The monobenzyl ester of (R-S)-2-methylmalonic acid obtained by alcoholysis of 2,2,5-trimethyl-1,3-dioxane-4,6-dione (Chorev et al., (1983), J. Med. Chem., 26,129–135) is incorporated into the peptide chain in racemic form. Coupling is monitored by the ninhydrin test. After this last coupling, the peptide-resin is washed twice with ether and dried in vacuo in a desiccator. The peptides are cleaved from the resin by treatment with anhydrous HF comprising 10% (v/v) of anisole and 1% (v/v) of 1,2-ethanedithiol. After removal of the HF in vacuo, the peptides are extracted from the resin and lyophilized. The crude peptides are then purified over a C18 column using a medium pressure apparatus (Kronwald Separation Technology, Sinsheim, FRG), by elution with a linear gradient of from 5 to 50% (v/v) of acetonitrile in 0.06% aqueous trichloroacetic acid. The purity of each fraction is determined by analytical passes over a column of Novapak C18 of 5 μm (3.9×150 mm), using a linear gradient of from 7 to 32% (v/v) of acetonitrile in an aqueous 0.1 M triethylammonium phosphate buffer. The passes are effected with a Waters apparatus (Waters Corporation, Milford, Mass.). The fractions comprising the pure mixture of diastereoisomers are collected and lyophilized. The mass spectra are obtained on a VG ZAB-2SE double concentration analytical instrument and recorded on a VG 11–250 data system (VG Analytical, Manchester, UK) as described (briand et al., (1989), Peptide Res., 2, 381–388). The circular dichroism measurements are carried out as described in (Benkirane et al., (1993), J. Biol, Chem., 268, 26279–26285).

Peptide Support Conjugation

In order to place the peptides on a plate to carry out a direct solid phase ELISA test, the IRGERA (SEQ ID NO:18) analogues are first conjugated to BSA using N-succinimidyl-3-[2-pyridyl-dithio]-propionate (SPDP) as described previously (14). For immunization of mice, the peptides are coupled covalently to preformed small unilamellar liposomes (SUV) containing: 4-(p-maleimidophenyl)-butyrylphosphatidyl-ethanolamine (MBP-PE). Monophosphoryl-lipid A (MPLA) is incorporated into the SUV as an adjuvant (Benkirane et al., (1993), J. Biol. Chem., 268, 26279–26285; Friede et al., (1993), Molec. Immunol., 30, 539–547).

Antisera and Monoclonal Antibodies

The antisera are obtained by immunizing BALB/c mice with peptides combined with liposomes as described in (Benkirane et al., (1993), J. Biol. Chem., 268, 26279–26285). The mice are injected intraperitoneally with various preparations of SUV comprising 1 µmol of lipid, 2 µg of MPLA and 60 µg of peptide per injection per animal.

The mice receive three injections at intervals of 3 weeks, and blood is sampled 5 days after each injection and then regularly for the 6 months following the last injection. The control serum is taken from each of the mice before the first injection. For preparation of monoclonal antibodies (MAb), the BALB/c mice are injection 3 times at intervals of 3 weeks with L and D peptides (100 µg) bonded covalently to SUV containing MPLA. Repeat injections are given on days 105, 106, 107 and 108, that is to say −4, −3, −2 and −1 before fusion. The monoclonal antibodies of the L and D peptides are prepared by the standard fusion protocols. Muller, S., Isabey, A., Couppez, M., Plaué, S., Sommermeyer, G., and Van Regenmortel, M. H. V. (1987) Mol. Immunol. 24, 779–789. Detailed descriptions of the generation and characterization of monoclonal antibodies are also given (Muller et al., Molecular Immunology, Vol. 24, No. 7, pp. 779–789, 1987).

Summarizing, production of these three monoclonal antibodies was carried out in the following manner:
immunization of BALB/c mice: see above,
actual fusion:
  L peptide: $2 \times 10^7$ lymphocytes of the immunized mouse+$2 \times 10^7$ myelomatous cells [PAI, ref. in Muller et al., 1987]
  D peptide: $3.2 \times 10^7$ lymphocytes+$3.5 \times 10^7$ PAI 2 successive sub-clonings for the two fusions.

Summary of the fusion plan:

| Peptide | Number of clones in total (%) | Number of positive clones (%) | 1st sub-cloning | 2nd sub-cloning | Production in ascites |
|---|---|---|---|---|---|
| L(4) | 120/195 wells (62.5%) | 30/120 (25%) | 24 | 21 | 8 |
| D(11) | 155/192 wells (80.7%) | 30/155 (19.3%) | 16 | 14 | 7 |

6 clones were cultured on a large scale to obtain several tens of mg of Ab. 41.6 mg of Ab 11×2, 80 mg of Ab 11×7 and 62 mg of Ab 4×11 were thus produced and purified.

The reactivity of the three monclonal antibodies 4×11 (derived from a mouse immunized against the L peptide), 11×2 and 11×7 (derived from a mouse immunized against the D peptide) is described below.

In addition, two other monoclonal antibodies 4×8 and 4×10 (JBC, vol 270, No. 20, May 19,1995, pp. 11921–11926) were also obtained, and the affinity constant of these antibodies with respect to the L-IRGERA (SEQ ID NO:18) and retro-inverso IRGERA (SEQ ID NO:18) peptide was measured. The results are given below (Table 2).

ELISA

The ELISA procedure (direct bonding and competition test) is as described in Benkirane et al., (1993) J. Biol. Chem. 268, 26279–26285).

Kinetic Analysis of the Bonding of the Monoclonal Antibody

For the bonding experiments in real time, a BIAcore biosensor system (Pharmacia Biosensor, AB, Uppsala, Sweden) is used. The reagents, including CM5 reaction surfaces (dextran), P20 surfactant and the coupling kit comprising N-hydroxysuccinimide (NHS), N-ethyl-N'-(3-dimethylaminopropyl)-carbodiimide (EDC), 2-(2-pyridinyldithio) ethane-amine (PDEA) and ethanolamine HCl, are obtained from Pharmacia Biosensor AB. To immobilize the peptides on the reaction surface (dextran), the standard protocol described previously (Stocker, J. W. et al., (1982) Disclosure 217, 155–157, and Zeder-Lutz, G., et al., (1993) J. Mol. Recognit. 6, 71–79) is used, except that the dextran surface is first activated by the NHS-EDC mixture, and then modified by injecting the coupling agent PDEA-thiol (15 µl of 80 mM PDEA in 0.1 M borate buffer, pH 8.5) and allowing the reactive thiol group of the peptide analogues to couple with the activated matrix by a thio-disulphide exchange reaction. After the immobilization of the peptide, the reactive groups remaining on the reaction surface are deactivated by a flow of 50 mM cysteine in 1 M NaCl, 1 M, pH 4.3 for 4 min.

The three monoclonal antibodies 4×11, 11×2 and 11×7 are then interacted with the reaction surfaces on which the four different analogues of the peptide have been immobilized. Six to ten concentrations of each monoclonal antibody ranging from 50 to 800 nM in HBS pH 7.4 (10 mM HEPES, 150 mM NaCl, 3.4 mM EDTA, 0.05% of P20 surfactant) are used in each test. The antibody preparation is injected at a constant flow rate of 3 µl per min for 7 min at 25° C. and the plotting points for the calculation are then taken every 10 seconds for 5 min, starting 1.30 min after the end of the injection of the monoclonal antibody (Zeder et al., (1993), Molec. Recogn., 6, 71–79).

The competition tests are carried out as described previously (Zeder et al., (1993), Molec. Recogn., 6, 71–79). The monoclonal antibodies 4×11, 11×2 and 11×7 (200 nM) are incubated with the competition peptides, used in a molar excess of 1.75 to 800 with respect to the antibody.

The kinetic constants of the antibodies are measured as described (Zeder et al., (1993), Molec. Recogn., 6, 71–79). The theory of kinetic measurements using the Biosensor BIAcore system has been described previously (Zeder et al., (1993), Molec. Recogn., 6, 71–79; Altschuh et al. (1992), Biochemistry, 31, 6298–6304).

Resistance to Trypsin

The resistance of the four peptide analogues to trypsin is tested using the proteolytic enzyme immobilized covalently on nylon spheres of 3.2 mm diameter (Michalon et al., (1993), Eur. J. Biochem., 216, 387–394). The specific activity of the enzymatic spheres is equivalent to 18 mmol of p-toluenesulphonyl-L-arginine methyl ester hydrolysed per minute per nylon sphere. Digestion by the protein is initiated by immersing 15 enzymatic spheres in 1 ml of a 150 µg/ml solution of the peptide, kept at 25° C. while stirring constantly. The digestion is carried out in HBS pH 7.4 for 5 to 240 min. The reaction is stopped by removing the enzymatic spheres. Cleavage of the peptides is evaluated immunochemically. The digestion mixtures are first incubated at 25° C. with MAb 11×2 (200 nM) for 30 min, and are then exposed to the L peptide, immobilized on the activated reaction surface as described previously. In this test, if the peptide in solution is resistant to trypsin, it competes with the bonding of MAb 11×2 to the L peptide immobilized on the activated dextran surface as described above, and the signal, expressed in resonance units (RU), is weak. Conversely, if the peptide is degraded by trypsin, there is no competition and the signal is equivalent to the control without the competition peptide.

Results

Synthetic Peptides

Figure 1:
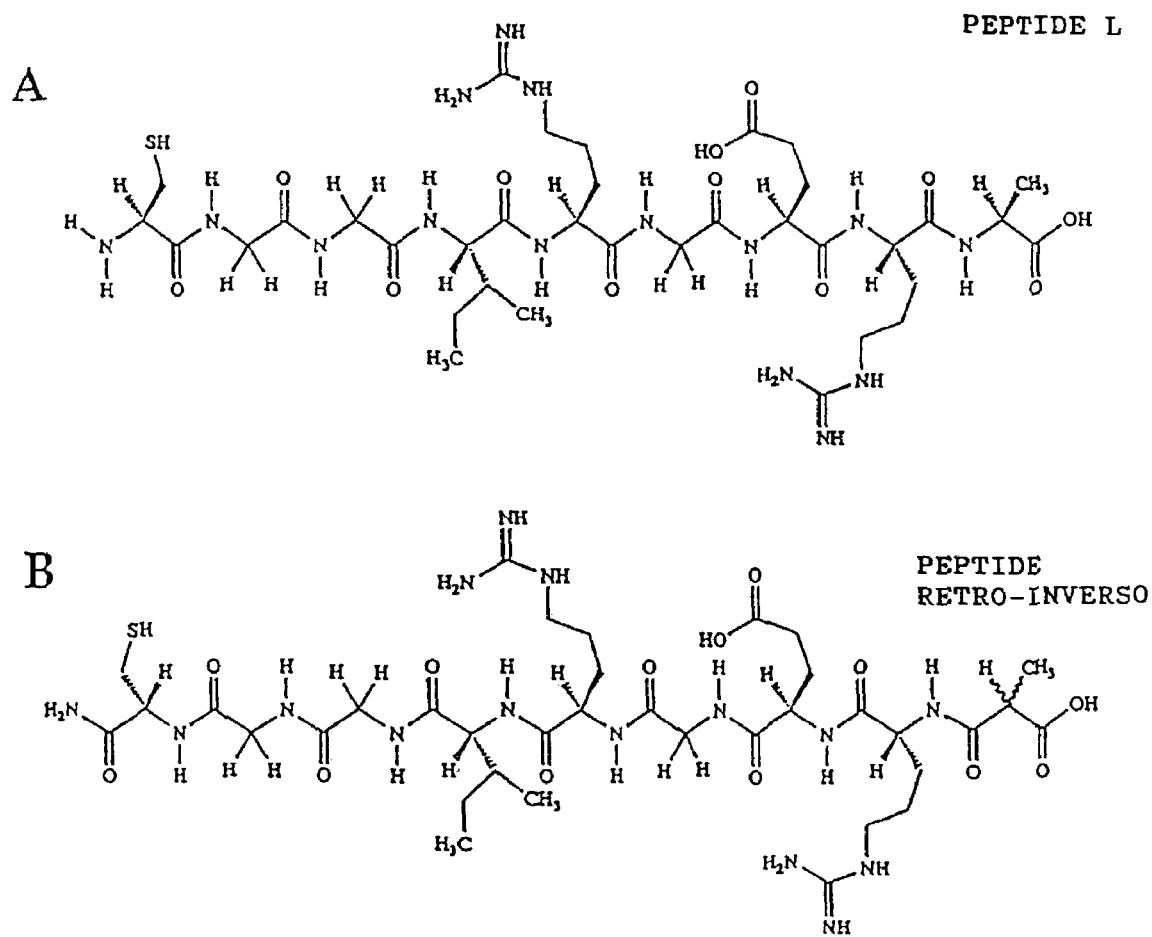

Four peptides are used in this study (FIG. 1). The parent peptide IRGERA (SEQ ID NO:18) corresponds to the COOH-terminal end of the histone H3 which has been studied previously (Friede et al., (1993) Molec. Immunol., 30, 539–547; Muller et al., (1982), EMBO J., 1, 421–425; Briand et al., (1992), J. Immunol. Meth., 156, 255–265). One cysteine and two additional glycine residues are added to the $NH_2$-terminal end to allow selective conjugation of the peptides to liposomes or to BSA and to increase the accessibility of peptides bonded to the support.

FIG. 1 shows the structure of the L peptide and the three structurally related analogues used in this study, that is to say the D enantiomer (Benkirane et al., (1993), J. Biol. Chem. 268, 26279–26285) and the retro-inverso and retro analogues modified at the ends. The retro analogue is obtained by replacing the normal residues of L amino acids by the corresponding D residues and reversing the direction of the peptide chain. This results in the topochemistry of the side chains being maintained, which means that the original spatial orientation of all the side chains is maintained (Goodman, M. and Chorev, M. (1979), Acc. Chem. Res., 12, 1–7). In the case of the retro analogue, the peptide chain is inverted but the chirality of the amino acids in the sequence is retained, which results in the chemistry of the side chains being non-complementary between this analogue and the parent peptide. This retro analogue is thus topochemically related to the D enantiomer. However, in such linear peptides, the two pairs of topochemically related peptides do not have the same groupings at the ends, and their charges are not complementary. To resolve this problem, a gem-diaminoalkyl residue may be introduced on the amino-terminal side and a 2-substituted malonic acid on the carboxy-terminal end (Goodmann, M. and Chorev, M. (1979), Acc. Chem. Res., 12, 1–7). However, monoacylated gem-diaminoalkyls are hydrolysed, and it must be expected from this that the half-life of peptides incorporating such residues will be 10 to 50 hours at 25° C. (Loudon et al. (1981), J. Am. Chem. Soc., 103, 4508–4515). Consequently, and because the $NH_2$-terminal cysteine is not part of the epitope, it was decided to use a carboxamide end. (R,S)-2-Methylmalonic acid is incorporated into the peptides in racemic form, thus generating a pair of diastereoisomers. The two diastereoisomers of the two retro and retro-inverso analogues are identified by HPLC analysis at 6.35 and 6.64 min for the retro-inverso and 6.50 and 6.78 min for the retro, but the separation is not sufficient to allow the diastereoisomers to be purified. The mixtures of the diastereoisomers are regarded, on the basis of the HPLC analysis, as being 87% pure for the retro-inverso and 86% for the retro, and the mass spectroscopy $(M+1)^+$ is 946.4.

The negative ellipticity found at 198 nm in the CD spectrum of the L peptide and of the retro peptides indicates a non-ordered form. As mentioned previously for the parent L peptide and its D enantiomer (Benkirane et al., (1993), J. Biol. Chem., 268, 26279–26285), the CD spectra of retro and retro-inverso analogues are mirror images.

Polyclonal Antibodies to the IRGERA (SEQ ID NO:18) Analogues

Figure 2:
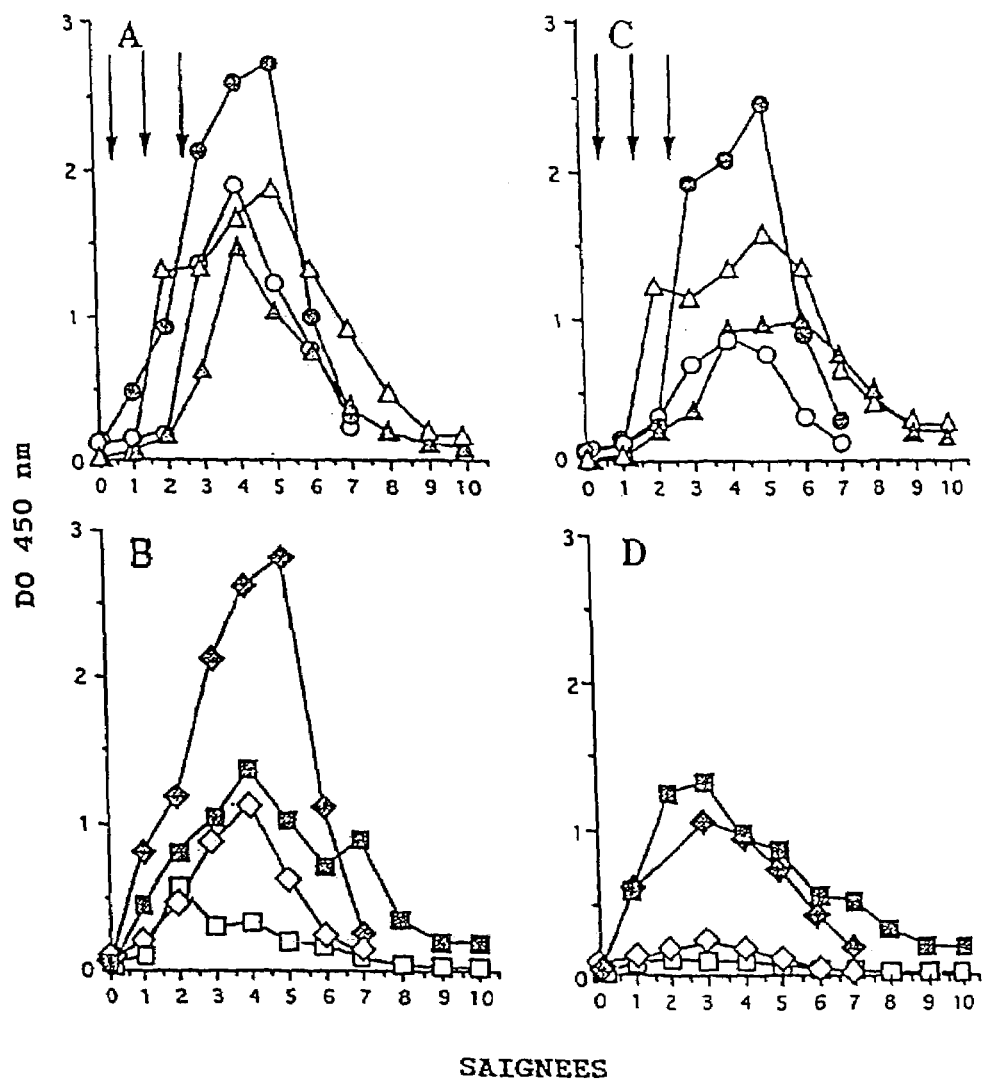

Groups of two BALB/c mice are injected with the four IRGERA (SEQ ID NO:18) analogues conjugated to liposomes. The reaction of the antibodies to the four peptides with the peptide analogues and with H3 is measured in a direct ELISA test. In this test, H3 and the four peptide analogues conjugated to BSA by means of SPDP are used to cover the plates. As shown on FIGS. 2A and 2B, a strong antibody response to the four peptides is obtained in the immunized mice. In the case of the L peptide, the antibodies belong to the IgG1, 2a and 2b subclasses. The IgG3 antibody response appears slightly later (blood sample 4) than the IgG1, 2a and 2b antibody response (blood sample 2). In the case of the retro-inverso, D and retro peptides, the IgG3 antibody response is predominant. The majority of the antibody subclasses give cross-reactions with the parent histone H3 (FIGS. 2C and 2D), with the exception of the IgG1, 2a and 2b antibody to the D peptide and the retro peptide (FIG. 2D), which show very little reaction with H3. It should be noted that although the IgG3 antibody response with respect to the retro-inverso peptide and the retro peptide is particularly strong, the duration of the antibody response is similar to that induced to the L and D peptides.

3) the retro-inverso IRGERA peptide mimics the natural L peptide well, but mimics neither the D peptide nor the retro peptide, while the retro peptide mimics the D peptide well, but mimics neither the L peptide nor the retro-inverso peptide.

The resulting antibodies of isotypes IgG1, 2a and 2b to the L peptide and the retro-inverso peptide recognize both the L peptide and the retro-inverso peptide, as well as the histone H3, but not the D peptide and the retro peptide. Conversely, the resulting antibodies of isotypes IgG1, 2a and 2b to the D peptide and the retro peptide recognize both the D peptide and the retro peptide, but neither the L peptide nor the retro-inverso peptide. The antibodies of isotype IgG3 induced to the four peptides undergo cross-reactions equally readily with the four peptide analogues and with H3. The immunoreactivity of conjugates of the peptide is confirmed in a bonding test in competition with the free peptides in solution (Table 1).

Generally, the results obtained with the two types of tests (conjugates of BSA-adsorbed peptides or free peptides) indicate that:

1) the antibodies of isotope IgG to the retro peptide and the retro-inverso peptide can easily be obtained;
2) regarding the immunoretroids and the D peptide, a strong IgG3 response is produced;
3) the retro-inverso IRGERA peptide mimics the natural L peptide well, but mimics neither the D peptide nor the retro peptide, while the retro peptide mimics the D peptide well, but mimics neither the L peptide nor the retro-inverso peptide.

Monoclonal Antibodies to the L- and D-IRGERA (SEQ ID NO:18) Analogues

Several fusion experiments were carried out with spleen cells of BALB/c mice immunized with the various IRGERA (SEQ ID NO:18) analogues described previously (9). From all the monoclonal antibodies obtained, three antibodies were chosen on the basis of their ELISA reactivity with the four peptide analogues. MAb 4×11 (IgG1) is generated by splenocytes of a mouse immunized with the L peptide; it reacts in ELISA with the L peptide and the retro-inverso peptide, but not with the D peptide and only weakly with the retro peptide. The monoclonal antibodies 11×2 and 11×7 (both IgG3) are generated by splenocytes of a mouse immunized with the D peptide; they react in ELISA with the four IRGERA analogues, as well as with the parent histone H3.

Bonding of these antibodies to the four peptide analogues is measured in a BIAcore using peptides bonded covalently to the dextran matrix via their free SH group. The kinetics constants and the affinity constants at equilibrium of the three monoclonal antibodies for the four peptide analogues are summarized in Table 2. The affinity constants at equilibrium (Ka) of MAbs 4×11, 11×2 and 11×7 with respect to homologous peptides are $3\times10^6$ M$^{-1}$, $1.3\times10^{10}$ M$^{-1}$ and $1.2\times10^7$ M$^{-1}$ respectively (Table 2). It should be noted that the two monoclonal antibodies 4×11 and 11×7 show a Ka value which is at least 50 times lower for the homologous peptides than for a heterologous peptide, that is to say the retro-inverso peptide in the case of monoclonal antibody 4×11 and the retro peptide in the case of monoclonal antibody 11×7 (Table 2). Monoclonal antibody 11×2 reacts with the four peptides. However, in comparison with the affinity of the antibody with respect to the homologous peptide, the Ka values are 30 times lower for the retro heterologous peptide and 103–104 times lower for the L peptide and the retro-inverso peptide (Table 2).

To confirm the difference in the immunoreactivity of the various peptide analogues, inhibition tests with the three monoclonal antibodies were carried out in the BIAcore system. The three monoclonal antibodies, preincubated with various concentrations of the four peptide analogues, were reacted with the homologous peptides immobilized on the SENSOR surface. As indicated in Table 3, bonding of monoclonal antibody 11×2 to the L and D peptides is inhibited by the four peptide analogues (50% inhibition of the bonding of the antibody observed with a 0.5 to 25 molar excess of the various peptides with respect to the antibodies). Bonding of monoclonal antibody 4×11 to the L peptide is inhibited only by the free L and retro-inverso peptides, while bonding of antibody 11×7 to the D peptide is inhibited only by the free D peptide and retro peptide. These results are thus in complete agreement with those obtained in the ELISA tests and the direct BIAcore test described above. At the quantitative level, however, if the reactivity of the antibodies with the four peptide analogues in ELISA and in the BIAcore system is compared, a low correlation is found in some cases (Table 4). For example, similar optical density (OD) values are obtained in ELISA if monoclonal antibody 11×2 is reacted with the L and D peptides, while the Ka values measured in the biosensor system show a difference of 4 logs.

Polyclonal Anti-Rabbit H3 Antibodies to the D, RI IRGERA (SEQ ID NO:18) Analogues and the Parent Peptide Table 5 shows that the anti-parent protein (histone H3) antibodies are capable of recognizing the parent IRGERA (SEQ ID NO:18) peptide and its analogue, the RI peptide, in ELISA in an identical manner. This result opens up all the possibilities for use of the immunoretroids in diagnosis in all cases where detection of antibodies to an exogenous protein (for example in virology or microbiology) or endogenous protein (for example autoimmunity or neurodegenerative diseases) is required.

It has been seen previously that anti-parent peptide monoclonal antibodies can recognize the RI peptide with an affinity which is much higher than that measured in the context of recognition of the parent peptide by the said monoclonal antibodies (see Table 2, monoclonal antibody MAb 4×11), which may enable the diagnosis test to be improved in certain cases, for example by using anti-RI antibodies, in particular monoclonal antibodies, to "prick" the protein sought in a biological mixture.

Resistance of the Peptide Analogues to Trypsin

Figure 3:
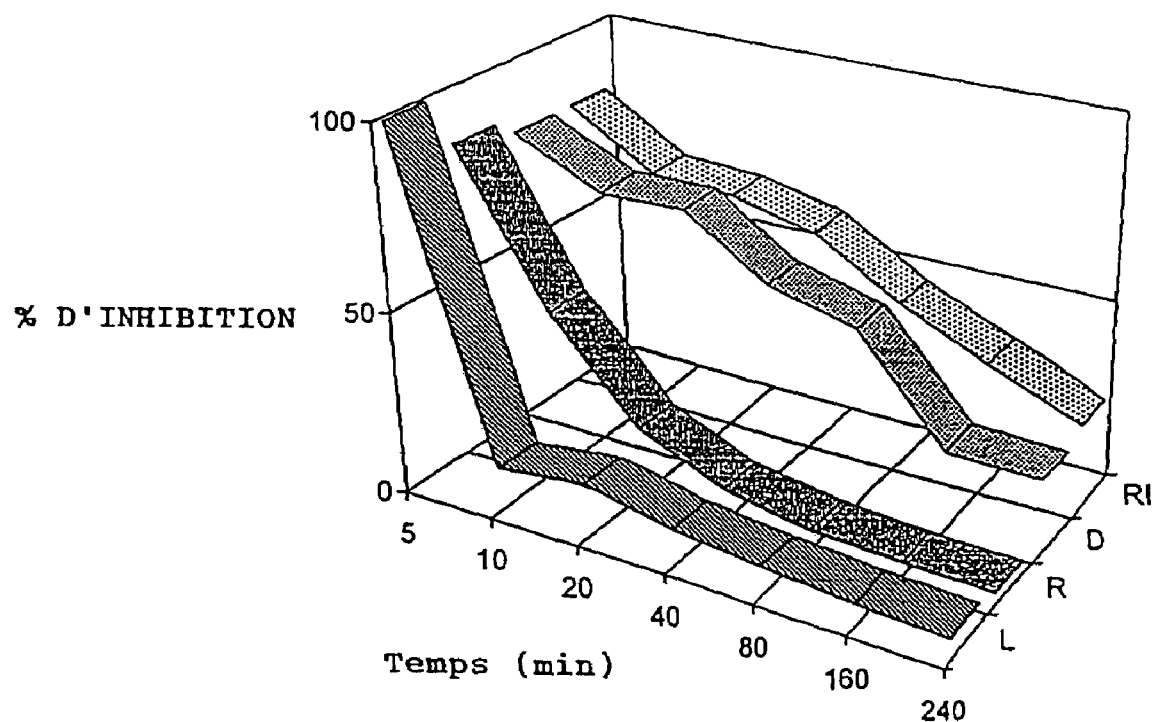
Figure 4:
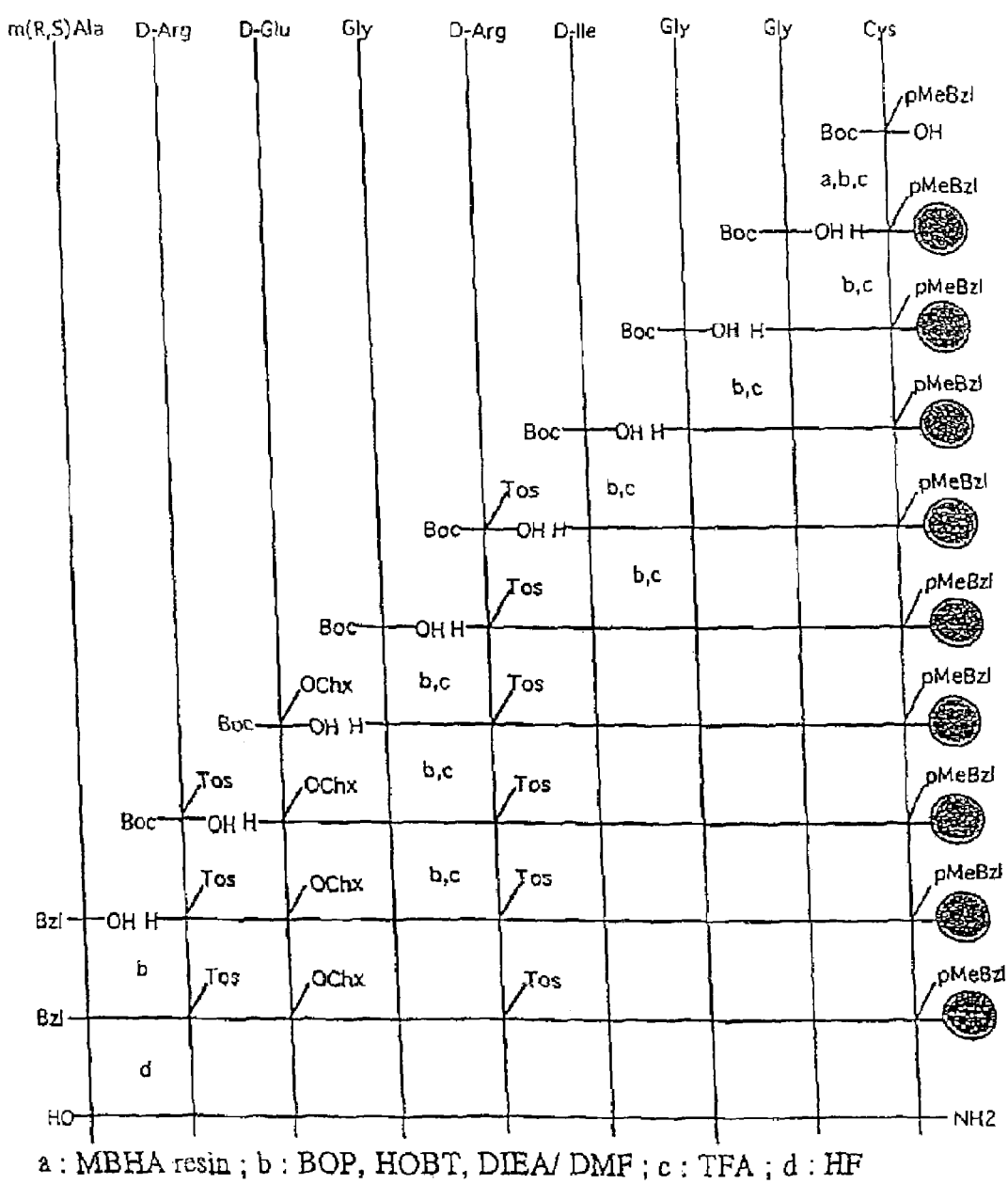
Figure 5:
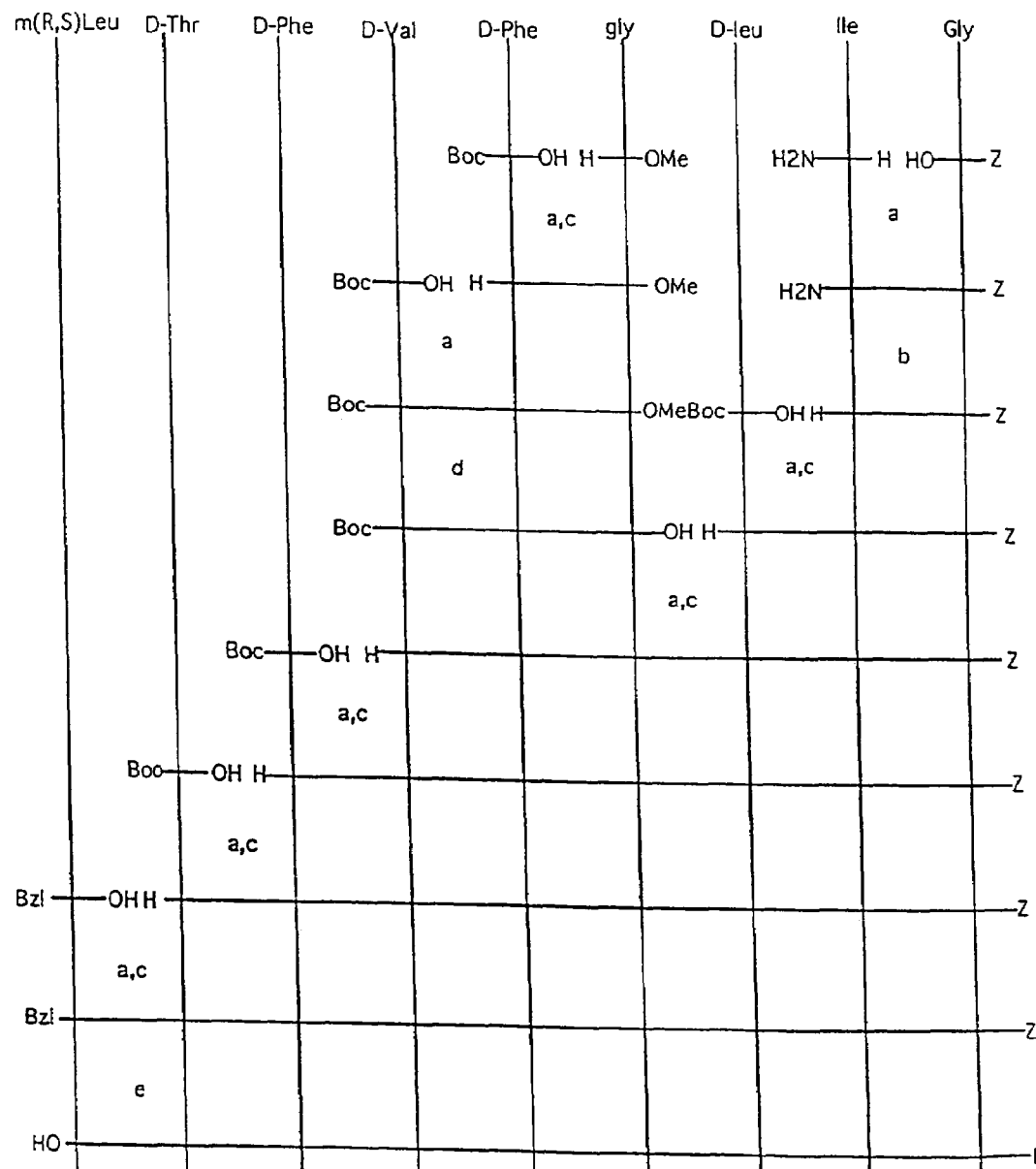

One of the potential advantages of the use of peptide analogues containing D amino acid residues or reversed peptide bonds rests in their higher resistance to protease, which could increase their immunogenicity in comparison with natural peptides. Using radioactive rubredoxin, Dintzis et al. (Dintzis et al., (1993), Proteins, 16, 306–308) showed, for example, that the D form of the protein was retained in the organism at least 4 times longer than the L form. Wade et al. (Wade et al., (1990), Proc. Natl. Acad. Sci., USA, 87, 4761–4765) showed that the D enantiomers of several peptide antibiotics are resistant to enzymatic degradation. The resistance of the peptide analogues to trypsin, the specificity of which is based on the positively charged side chains of arginine and lysine, was tested here. The enzyme immobilized covalently on nylon spheres was used, and the residual capacity of the proteolysed enzymes for competing with the L peptide for bonding to monoclonal antibody 11×2 was measured in the BIAcore. Monoclonal antibody 11×2 is used in this test because it recognizes the four analogues in solution (Table 3). The advantage of using the enzyme immobilized on nylon spheres rests in its higher stability, the absence of addition of an agent which blocks the action of the protease to terminate the reaction, and total experimental control of the experiment (Michalon et al., (1993), Eur. J. Biochem., 216, 387–394). As shown on FIG. 3, the L peptide is digested rapidly under these conditions. Half of its antigenic activity is lost after 7 min, and no activity remains after 10 min. The retro peptide is slightly less sensitive (half-life: 9 min, complete loss of immunological activity 40 min), while the D and retro-inverso peptides are much more resistant to trypsin (half-life: 73 and 67 min respectively, complete loss of activity still not found after 240 min).

TABLE I

Recognition in an ELISA competition test of the IRGERA (SEQ ID NO:18) peptide and IRGERA (SEQ ID NO:18) analogues by murine antibodies induced to the homologous peptides and peptide analogues

| Antigens used as inhibitors | Molar excess of inhibitor peptide required to inhibit 50% of the bonding between the anti-peptide antibodies and the homologous antigens | | | |
|---|---|---|---|---|
| | anti-L | anti-RI | anti-D | anti-R |
| | IgG1, 2a, 2b response | | | |
| L peptide | 10 | 80 | —* | — |
| RI peptide | 10 | 10 | — | — |
| D peptide | — | — | 10 | 20 |
| R peptide | — | — | 5 | 10 |
| H3 | 5 | 18 | — | — |
| | IgG3 response | | | |
| L peptide | 10 | 50 | 5 | 70 |
| RI peptide | 50 | 10 | 10 | 70 |
| D peptide | 10 | 70 | 5 | 30 |
| R peptide | 5 | 70 | 50 | 10 |
| H3 | 5 | 60 | 5 | 90 |

Microtitration plates are coated with 2 µM of peptide conjugated to BSA with the aid of SPDP (molar ratio of peptide to carrier 1:10), and are incubated with the antisera of mice to the homologous peptide (serum dilution 1:500) and preincubated with the various peptides and with H3 used as an inhibitor. A control peptide corresponding to the sequence 149–158 of the protein of the tobacco mosaic virus is used as an internal reference and has no effect on bonding with the antibodies.

The anti-murine IgG conjugates coupled to peroxidase are both diluted 1:5,000.

The molar excesses of the inhibitor peptide are expressed as a function of the peptide deposited in the wells of the microtitration plates and are calculated as described (Benkirane et al., (1993), J. Biol. Chem., 268, 26279–26285).

*-cross-reactivity not detectable (up to 125 µg/ml of competition peptide)

L=parent L peptide, RI=retro-inverso peptide, D=D peptide, R=retro peptide.

TABLE 2

Kinetic constants and affinity constants at equilibrium of MAb 4 × 11, 11 × 2 and 11 × 7 for the four IRGERA (SEQ ID NO:18) analogues, and 4 × 8 and 4 × 10 for L-IRGERA (SEQ ID NO:18) and RI-IRGERA (SEQ ID NO:18).

| MAbs | peptide used as the antigen | $ka(\times 10^3)$ $(M^{-1}s^{-1})$ | $kd(\times 10^{-5})$ $(s^{-1})$ | $Ka(\times 10^6)$ $(M^{-1})$ |
|---|---|---|---|---|
| 4 × 11 (IgG1) | L | 3 ± 0.2 | 100 ± 0.3 | 3 |
| anti-L peptide | RI | 18 ± 0.5 | 8 ± 0.2 | 225 |
|  | D | nb* | — | — |
|  | R | nb | — | — |
| 11 × 2 (IgG3) | L | 2 ± 0.3 | 100 ± 0.2 | 2 |
| (anti-D peptide) | RI | 13 ± 0.6 | 160 ± 0.3 | 8 |
|  | D | 130 ± 0.3 | 1 ± 0.4 | 13,000 |
|  | R | 5 ± 0.5 | 1 ± 0.3 | 500 |
| 11 × 7 (IgG3) | L | nb | — | — |
| (anti-D peptide) | RI | nb | — | — |
|  | D | 3 ± 0.4 | 25 ± 0.5 | 12 |
|  | R | 6 ± 0.6 | 1 ± 0.4 | 600 |
| 4 × 8 (IgG1) | L | 13 ± 0.2 | 15 ± 0.2 | 80 |
| (anti-L peptide) | RI | 419 ± 0.4 | 75 ± 0.5 | 558 |
| 4 × 10 (IgG1) | L | 987 ± 0.7 | 22 ± 0.2 | 4,486 |
| (anti-L peptide) | RI | 910 ± 0.5 | 25 ± 0.4 | 3,640 |

*nb, no bonding

The association constant (ka) and dissociation constant (kd) are the mean values obtained in two to four independent experiments.

L=parent L peptide; RI=retro-inverso peptide; D=D peptide; R=retro peptide.

TABLE 3

Recognition in a competition test in the BIAcore system of the IRGERA (SEQ ID NO:18) peptide and the IRGERA (SEQ ID NO:18) analogues by the antibodies MAb 4 × 11, 11 × 2 and 11 × 7

| | Molar excesses of inhibitor peptide required to inhibit 50% of the bonding between the MAb and | | | |
|---|---|---|---|---|
| Peptides used | L peptide | | D peptide | |
| as inhibitors | MAb 4 × 11 | MAb 11 × 2 | MAb 11 × 2 | MAb 11 × 7 |
| L | 1 | 1 | 10 | —* |
| RI | 1 | 3 | 15 | — |
| D | — | 1 | 10 | 10 |
| R | — | 0.5 | 25 | 10 |

L = parent L peptide, RI = retro-inverso peptide, D = D peptide, R = retro peptide. The molar excesses of the inhibitor are expressed with respect to the antibody (200 nM MAb).
*—, cross-reactivity not detectable (up to 250 μg/ml of competition peptide).

TABLE 4

ELISA reactivity of MAb 4 × 11, 11 × 2 and 11 × 7 with the four IRGERA (SEQ ID NO:18) analogues. Affinity constants at equilibrium of the three MAb for the four analogues.

| | | Reactivity with the peptides | | | |
|---|---|---|---|---|---|
| MAb | Tests | L | RI | D | R |
| 4 × 11 | ELISA (OD) | 1.29 | 1.12 | 0.19 | 0.40 |
|  | BIAcore (Ka M$^{-1}$) | 3 × 10$^6$ | 2 × 10$^8$ | nb* | nb |
| 11 × 2 | ELISA (OD) | 2.75 | 1.78 | 2.92 | 1.92 |
|  | BIAcore (Ka M$^{-1}$) | 2 × 10$^6$ | 8 × 10$^6$ | 1 × 10$^{10}$ | 5 × 10$^8$ |
| 11 × 7 | ELISA (OD) | 0.47 | 0.89 | 1.45 | 0.78 |
|  | BIAcore (Ka M$^{-1}$) | nb | nb | 1 × 10$^7$ | 6 × 10$^8$ |

*nb, no bonding.

For the ELISA, the microtitration plates are coated with 2 μM of peptide conjugated to BSA with the aid of SPDP and incubated with the MAb (4 μg/ml). The anti-murine IgG-peroxidase conjugates are diluted 1:5,000.

L=parent L peptide, RI=retro-inverso peptide, D=D peptide, R=retro peptide.

TABLE 5

Reactivity of the anti-histone H3 (parent protein) antibodies induced in the rabbit with the L, D and RI IRGERA (SEQ ID NO:18) peptides.

| Antigens (peptides tested) | Dilution of anti-H3 serum | Anti-H3 antisera | | | Normal rabbit serum |
|---|---|---|---|---|---|
| | | Rabbit 1 | Rabbit 2 | Rabbit 3 | |
| L PEPTIDE | 1:1,000 | 2.71$^{(1)}$ | 2.29 | 1.98 | 0.06 |
|  | 1:2,000 | 1.61 | 1.45 | 1.10 | 0.03 |
|  | 1:4,000 | 0.92 | 0.88 | 0.57 | 0.02 |
| RI PEPTIDE | 1:1,000 | 2.79 | 2.39 | 1.95 | 0.08 |
|  | 1:2,000 | — | 1.38 | 1.15 | 0.15 |
|  | 1:4,000 | 0.92 | 0.91 | 0.71 | 0.15 |
| D PEPTIDE | 1:1,000 | 0.04 | 0.02 | 0.02 | 0.03 |
|  | 1:2,000 | 0.03 | 0.02 | 0.01 | 0.05 |
|  | 1:4,000 | 0.18 | 0.01 | 0.01 | 0.04 |

$^{(1)}$Optical density values at 450 nm.

EXAMPLE 2

Retro-Inverso Peptides and Diagnosis

Throughout the last decade, solid phase immunoassays such as the ELISA test and radioimmunological tests in the solid phase have become more and more topical, and these tests are now widely used to determine the antigenic activity of synthetic peptides for both diagnostic and experimental purposes. In particular, a certain number of immunoassays based on the use of synthetic peptides have been developed for detection and quantification of autoantibodies present in the sera of patients suffering from autoimmune diseases (Elkon, K. B., (1992) Use of synthetic peptides for the detection and quantification of autoantibodies. Molec. Biol. Rep., 16: 207–212; Muller, S. (1994), Use of synthetic peptides for the analysis of B-cell epitopes in autoantigens. In: M. Zouali (Ed.) Autoimmunity: Experimental Aspects. Springer-Verlag, Berlin, Heidelberg, p. 76–90). It is important to emphasize that during the tests, the peptides used, whether free in solution or adsorbed directly on the microtitration plates, can be altered by the proteases which are present in the sera of patients. One of the characteristics of the acute inflammatory reaction is in fact the release of various proteolytic enzymes, leading to a lesion of tissues and subsequent release of other proteases (Kaplan, A. P. and Silverberg, M. (1988) Mediators of inflammation: an overview. Meth. Enzymol., 163: 3–23). With autoimmune diseases such as rheumatoid polyarthritis or disseminated lupus erythematosus (DLE), degradation of inflammatory tissue may also be caused by immune complexes in the circulation (Levinson, S. S. (1994), Humoral mechanisms in autoimmune disease. J. Clin. Immunoassay, 17: 72–84). Proteolytic degradation of peptides may be contorted by their conjugation to a carrier protein. However, this stage may be an unsuitable technique for certain laboratories where, depending on the sequence of the peptide in question, a coupling strategy may be difficult to adopt if residues which are not part of the epitope are not available. As an alternative, according to one of its aspects, the invention proposes conversion of antigenic peptides into peptide analogues which mimic the parent peptides ("peptidomimetics") and are resistant to proteolytic degradation while maintaining a high antigenic activity.

2. Materials and Methods.

2.1 Peptides.

All the peptide analogues are synthesized by the solid phase method on a peptide multisynthesizer (Neimark, J. and briand, J. P. (1993) Development of a fully automated multichannel peptide synthesizer with integrated TFA cleavable capability. Peptide Res. 6: 219–228), using a completely automatic mode for the L peptides and a semi-automatic mode for the retro-inverso peptides. The protected L and D amino acid derivatives originate from Neosystem (Strasbourg). A diagram of the peptide analogues used in this example is shown on Table 6.

2.1.1 Peptide 130–135 of Histone H3.

The synthesis of the L and retro-inverso peptides has been described previously (Guichard, G., Benkirane, N., Zeder-Lutz, G., Van Regenmortel, M. H. V., briand, J. P. and Muller, S. (1994) Antigenic mimicry of natural L-peptides with retro-inverso-peptidomimetics. Proc. Natl. Acad. Sci., USA, 91: 9765–9769).

2.1.2 Peptide 277–291 of 52 kD SSA/Ro (Ro52) Protein.

The L and retro-inverso peptides are linked by Boc chemistry on a Boc Leu Pam (phenylacetamidomethyl) resin and on a p-methylbenzhydrylamine resin respectively. Linkage of the protected peptide chain is effected on a scale of 100 µmol using the in situ neutralization described previously (Neimark, J. and briand, J. P. (1993) Development of a fully automated multichannel peptide synthesizer with integrated TFA cleavable capability. Peptide Res. 6: 219–228). For the retro-inverso peptides, the C-terminal end of the parent peptide is mimicked using a malonate derivative. The monobenzyl ester of (R,S)-2-isobutylmalonic acid obtained by alcoholysis of 2,2-dimethyl-5-isobutyl-1,3-dioxane-4,6-dione (Chorev, M., Rubini, E., Gilon, C., Wormser, U. and Selinger, Z. (1983) Synthesis of partially modified retro-inverso substance P analogues and their biological activity. J. Med. Chem., 26: 129–135) is incorporated into the peptide in the form of the racemate, thus generating a pair of diastereoisomers. The peptides are cleaved from the resin by treatment with anhydrous hydrofluoric acid (HF) comprising 10% (v/v) of anisole and 1% (v/v) of 1,2-ethanedithiol.

After removal of the HF in vacuo, the peptides are extracted from the resin and lyophilized. The crude peptides are then purified over a column of Aquapore C18 ODS (100×10 mm) using a preparative HPLC apparatus (Perkin Elmer, Saint-Quentin en Yvelines, France). As regards the retro-inverso analogue, it was possible to separate and purify the two diastereoisomers by HPLC. They are identified according to their retention time. The retro-inverso isomer, which is eluted faster, is called "RIa peptide" and the peptide eluted more slowly is called "RIb peptide" (Table 6). The level of isomerization of the separated diastereoisomers was monitored at 4° C. and at 37° C. Both isomerize if they are incubated for 12 hours at 37° C. (conditions usually used to sensitize ELISA plates), and the RIa and RIb components lead to an equilibrium mixture of the diastereoisomers of about 50:50 (RIa/RIb) and 70:30 (RIb/RIa) respectively. In contrast, the two isomers seem very stable at 4° C., given that no change in the respective HPLC profiles is observed. The plastic plates were thus coated with the peptide analogues Ro52 277–291 at 4° C. throughout this entire study.

2.1.3 Peptide 304–324 of 60 kD SSA/Ro Protein.

Two series of peptides were synthesized. In the first series, the N- and C-terminal ends of the parent peptide and the reversed ends of the retro-inverso peptide are not protected. They are linked by Fmoc chemistry on a p-alkoxybenzyl alcohol resin. In the retro-inverso D-allo-Ile analogue, D-allo-Ile is introduced instead of D-Ile. In the second series of analogues, the N- and C-terminal ends of the parent peptide and of the retro-inverso peptides are acetylated and amidated respectively. These blocked peptides are linked by Fmoc chemistry on an Fmoc-2,4-dimethoxy-4'-(carboxymethyloxy)-benzhydrylamine resin.

Linking of the protected peptide chains is carried out on a scale of 25 µmol according to a conventional Fmoc methodology. The peptides on the resin are cleaved with reagent K (King, D., Fields, C., and Fields, G. (1990) A cleavage method which minimizes side reactions following Fmoc solid-phase peptide synthesis. Int. J. Pept. Protein Res., 36: 255–266) for two hours and each peptide is collected in a tube filled with tert-butyl methyl ether at 4° C. After centrifugation, the cups are washed twice with cold ether. After the last centrifugation, each peptide is dissolved in an aqueous solution for lyophilization. The crude peptides are finally purified as described above.

2.1.4 Peptide 28–45 of Histone H3.

Four peptide analogues were synthesized, that is to say the parent L peptide, the L peptide in which the free terminal COOH group is replaced by a carboxamide group —CONH$_2$, and the L and retro-inverso peptide with the N- and C-terminal ends blocked (Table 6). The four peptides are prepared by Fmoc chemistry as described above.

All the peptides used in this study were monitored by HPLC and analysed by mass spectrometry (FAB) MS.

2.1.5 Peptide C18L of Haemagglutinin of the Influenza Virus.

The synthesis of the L-peptide C18L deriving from HA91–108 of haemagglutinin of the influenza virus, and the preparation of the Salmonella flagellin carrying C18L has been prepared as described previously (McEwen, J., Levi, R., Horwitz, R. J. and Arnon, R. Synthetic recombinant vaccine expressing influenza haemagglutinin epitope in Salmonella flagellin leads to partial protection in mice. Vaccine 1992, 10, 1040–1044).

The synthesis of the retro-inverso peptides has been achieved according to the methods described previously (Guichard, G., Benkirane, N., Zeder-Lutz, G., Van Regenmortel, M. H. V., Briand, J. P. and Muller, S. (1994) Antigenic mimicry of natural L-peptides with retro-inverso-peptidomimetics. Proc. Natl. Acad. Sci., USA, 91: 9765–9769; Briand, J. P., Guichard, G., Dumortier, H., Muller, S. (1995) Retro-Inverso Peptidomimetics as new Immunological Probes. *J. Biol. Chem.* 270, 20686–20691).

2.1.6 Peptide 9B1 of *Schistosoma mansoni.*

The synthesis of the L-peptide 9B1 has been described previously (Tarrab-Hazdai, R., Schechtman, D., Ruth, A. (1998) Synthesis and Characterization of a Protective Peptide-Based Vaccine against *Schistosoma mansoni*., Infection and Immunity, 66, 4526–4530).

The synthesis of the retro-inverso peptides has been achieved according to methods described previously (Guichard, G., Benkirane, N., Zeder-Lutz, G., Van Regenmortel, M. H. V., Briand, J. P. and Muller, S. (1994) Antigenic mimicry of natural L-peptides with retro-inverso-peptidomimetics. Proc. Natl. Acad. Sci., USA, 91: 9765–9769; Briand, J. P., Guichard, G., Dumortier, H., Muller, S. (1995) Retro-Inverso Peptidomimetics as new Immunological Probes. J. Biol. Chem., 270, 20686–20691).

2.1.7 Peptide Mimotope of Measles Virus.

The synthesis of the peptide mimotope has been described previously (Steward, M. W., Stanley, C. M., Obeid, O. E., (1995) A mimotope from a Solid-Phase Peptide Library Induces a Measles Virus-Neutralizing and Protective Antibody response. Journal of Virology, 69, 7668–7673).

The synthesis of the retro-inverso peptides has been achieved according to methods described previously (Guichard, G., Benkirane, N., Zeder-Lutz, G., Van Regenmortel, M. H. V., Briand, J. P. and Muller, S. (1994) Antigenic mimicry of natural L-peptides with retro-inverso-peptidomimetics. Proc. Natl. Acad. Sci., USA, 91: 9765–9769; Briand, J. P., Guichard, G., Dumortier, H., Muller, S. (1995) Retro-Inverso Peptidomimetics as new Immunological Probes. J. Biol. Chem. 270, 20686–20691).

2.1.8 Cyclic Peptide HIV gp41.

The synthesis of the cyclic peptide HIV gp41 has been described previously (Limal, D., Briand, J. P., Dalbon, P., Jolivet, M., (1998) J. Peptide Res. 52, 121–129).

The synthesis of the retro-inverso peptides has been achieved according to methods described previously (Guichard, G., Benkirane, N., Zeder-Lutz, G., Van Regenmortel, M. H. V., Briand, J. P. and Muller, S. (1994) Antigenic mimicry of natural L-peptides with retro-inverso-peptidomimetics. Proc. Natl. Acad. Sci., USA, 91: 9765–9769; Briand, J. P., Guichard, G., Dumortier, H., Muller, S. (1995) Retro-Inverso Peptidomimetics as new Immunological Probes. *J. Biol. Chem.* 270, 20686–20691).

2.2 Binding of Zinc to Peptide Analogues of Peptide 304–324 of Ro60.

The capacity for the parent peptide Ro60 304–324 and the retro-inverso analogues to bond to zinc ions was tested using $^{65}$Zn. The peptides were immobilized on nitrocellulose as described previously (Mazen, A., Menissier-de Murcia, J., Molinete, M., Simonin, F., Gradwohl, G., Poirier, G., and de Murcia, G. (1989), Poly(ADP-ribose)polymerase: a novel finger protein. Nucl. Acids. Res., 17: 4689–4698; Muller, S., briand, J. P., Barakat, S., Lagueux, J., Poirier, G., De Murcia, G., and Isenberg, D. A. (1994) Autoantibodies reacting with poly(ADP-ribose) and with a zinc-finger functional domain of poly(ADP-ribose) polymerase involved in the recognition of damaged DNA. Clin. Immunol. Immunopathol., 73: 187–196).

2.3 Coupling of the Peptide 130–135 of H3.

The peptide 130–135 of H3 and its retro-inverso analogue were conjugated to bovine serum albumin (BSA) by means of N-succinimidyl-3-[2-pyridyldithio]-propionate (SPDP). The coupling yield was measured by spectrophotometry by studying the salting out of 2-thiopyridone from BSA modified with SPDP during interaction with peptides containing a cysteine (Muller, S. (1988) Peptide-carrier conjugation. In: R. H. Burdon and P. H. van Kippenberg (Eds), Synthetic Polypeptides as Antigens. Elsevier, Amsterdam, p. 95–130).

2.4 Autoimmune Human and Murine Sera

Sera of female F1 lupous mice (NZB/W) were obtained from S. Batsford (Freibourg, Germany). The human sera originate from patients suffering from disseminated lupus erythematosus (DLE) and Sjögren's syndrome (SS). They were obtained from D. A. Isenberg (London), O. Meyer (Paris) and G. Fournié (Toulouse). The sera of healthy volunteers were obtained from J. L. Pasquali (Strasbourg). The majority of these sera were used in the previous studies (Ricchiuti, V., briand, J. P., Meyer, O., Isenberg, D. A., Pruijn, G. and Muller, S. (1994) Epitope mapping with synthetic peptides of 52 kD SSA/Ro protein reveals heterogeneous antibody profiles in human autoimmune sera. Clin. Exp. Immunol., 95: 397–407; Ricchiuti, V. and Muller, S. (1994) Use of peptides for the mapping of B-cell epitopes recognized by anti-Ro (SS-A) antibodies. In: D. A. Isenberg and A. C. Horsfall (Eds.), Autoimmune Diseases: focus on Sjögren's syndrome. Bios Scientific Publishers, Oxford, p. 101–106).

2.5 ELISA Test.

The sera of lupous mice were tested by ELISA as described previously (Benkirane, N., Friede, M., Guichard, G., briand, J. P., Van Regenmortel, M. H. V. and Muller, S. (1993) Antigenicity and immunogenicity of modified synthetic peptides containing D-amino acid residues. J. Biol. Chem., 268: 26279–26285). Only the antibodies of isotype IgG were tested. The test of antibodies of isotype IgG which react with the peptides of Ro52 and Ro60 was carried out as described by Barakat et al. (Barakat, S., Meyer, O., Torterotot, F., Youinou, P., briand, J. P., Kahn, M. F. and Muller, S. (1992) IgG antibodies from patients with primary Sjögren's syndrome and systemic lupus erythematosus recognize different epitopes in 60-kD SSA/Ro protein. Clin. Exp. Immunol., 89: 38–45) and Ricchiuti et al. (Ricchiuti, V., briand, J. P., Meyer, O., Isenberg, D. A., Pruijn, G. and Muller, S. (1994) Epitope mapping with synthetic peptides of 52 kD SSA/Ro protein reveals heterogeneous antibody profiles in human autoimmune sera. Clin. Exp. Immunol., 95: 397–407) except in the case of the peptide Ro52 277–291, where sensitization of the ELISA plates was carried out at 4° C. instead of 37° C. (see the reasons above). The threshold value for positivity of each test, including that of tests based on the use of retro-inverso peptide analogues, was determined using 20 sera of healthy individuals. The antigenic activity of the peptides is also measured by ELISA using a liquid phase inhibition test. The procedure is as described previously (Ricchiuti, V., briand, J. P., Meyer, O., Isenberg, D. A., Pruijn, G. and Muller, S. (1994) Epitope mapping with synthetic peptides of 52 kD SSA/Ro protein reveals heterogeneous antibody profiles in human autoimmune sera. Clin. Exp. Immunol., 95: 397–407).

The varied sera described in FIGS. 14 to 17 were tested by ELISA as described previously. The different peptides described in FIGS. 14 to 17 have been adsorbed on the plate.

3. Results.

3.1 Synthetic Peptides and Retro-Inverso Analogues.

As regards the native peptide sequence, the retro-inverso modification of linear polypeptides involves synthetic linking in an inverse order of the amino acids with the stereochemistry of the α-carbon opposite to that of the corresponding L amino acids. The result is that the positions of the amino and carboxyl groups in each of the peptide bonds are changed, while the topology of the side chains is similar or identical to that of the natural peptide. The inversion of the terminal groups creates a major problem in the complementarity of structure and charge. However, a whole range of approaches has been proposed to deal with this problem (Goodman, M. and Chorev, M. (1979) On the concept of linear modified retro-peptide structures. Acc. Chem. Res., 12: 1–7). For example, the retro-inverso analogues of peptide 130–135 of H3 and 277–291 of Ro52 are synthesized as retro-inverso isomers modified at their terminal ends. A C-2-substituted malonic acid residue was introduced to mimic closely the C-terminal carbon of the parent peptides and of the carboxamide group ($-NH_2-CO-$) instead of the free terminal amino group. It was possible to separate the two diastereoisomers of the retro-inverso peptide 277–291 of Ro52 (RIa and RIb analogues, Table 6) by HPLC.

An alternative to limit the problem of the terminal end comprises preparation of blocked peptides and of blocked retro-inverso analogues. This solution was adopted for the peptides 304–324 of Ro60 and 28–45 of H3. The use of this strategy obviously involves as a prerequisite that the peptides with their terminal ends blocked are also recognized by the antibodies.

Another problem in the approach of retro-inverso peptides is that the secondary asymmetric centres of the side chains of threonine and isoleucine must retain their correct chirality. This has been studied with the peptide 304–324 of Ro60, which was synthesized in its retro-inverso form both with D-Ile residues and with D-allo-Ile residues (Table 6.).

The purity of the 13 peptide analogues used in this study is greater than 80%, as shown by analytical HPLC. MS-(FAB) analysis gives the results expected for all the compounds.

3.2 Recognition of the Retro-Inverso Analogue of the C-terminal Hexapeptide of H3 by the Sera of Lupous Mice.

The C-terminal hexapeptide of histone H3 corresponds to a major epitope of the protein (Muller, S., Himmelspach, K. and Van Regenmortel, M. H. V. (1982) Immunochemical localization of the C-terminal hexapeptide of histone H3 at the surface of chromatin subunits. EMBO J., 1: 421–425). This segment was used as the model peptide in previous studies on modified peptides, in particular to show that the retro-inverso analogues may be much more resistant to proteolytic enzymes than the L peptides (Guichard, G., Benkirane, N., Zeder-Lutz, G., Van Regenmortel, M. H. V., briand, J. P. and Muller, S. (1994) Antigenic mimicry of natural L-peptides with retro-inverso-peptidomimetics. Proc. Natl. Acad. Sci., USA, 91: 9765–9769). A series of sera from female F1 mice (NZB/W) was first targeted with the parent peptide 130–135 of H3, and a certain number of positive sera were selected. These sera were then tested by ELISA for their capacity to react with the retro-inverso peptide 130–135. As shown on Table 7, the sera of lupous mice react just as well with the retro-inverso peptide 130–135 as with the parent peptide 130–135.

3.3. Recognition of the Retro-Inverso Analogue of Ro52 277–191 by the Sera of Autoimmune Patients.

Figure 6:
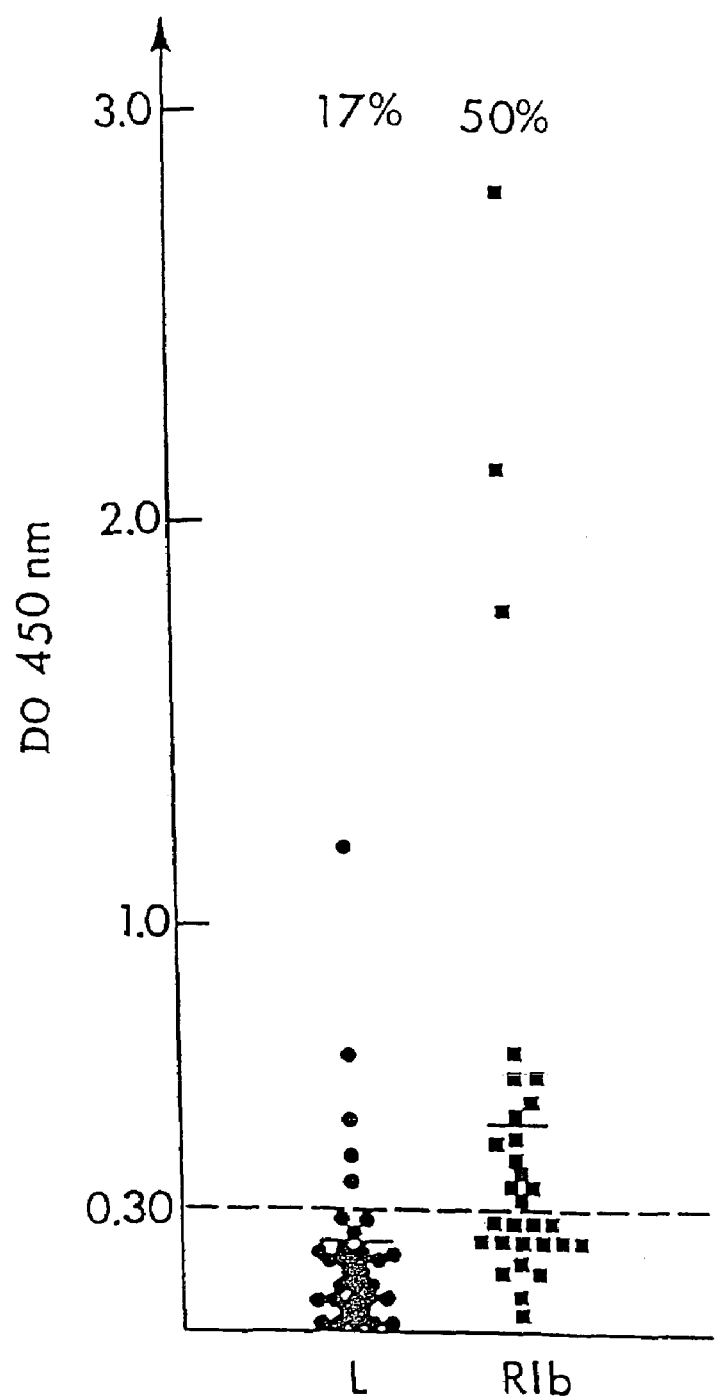
Figure 7:
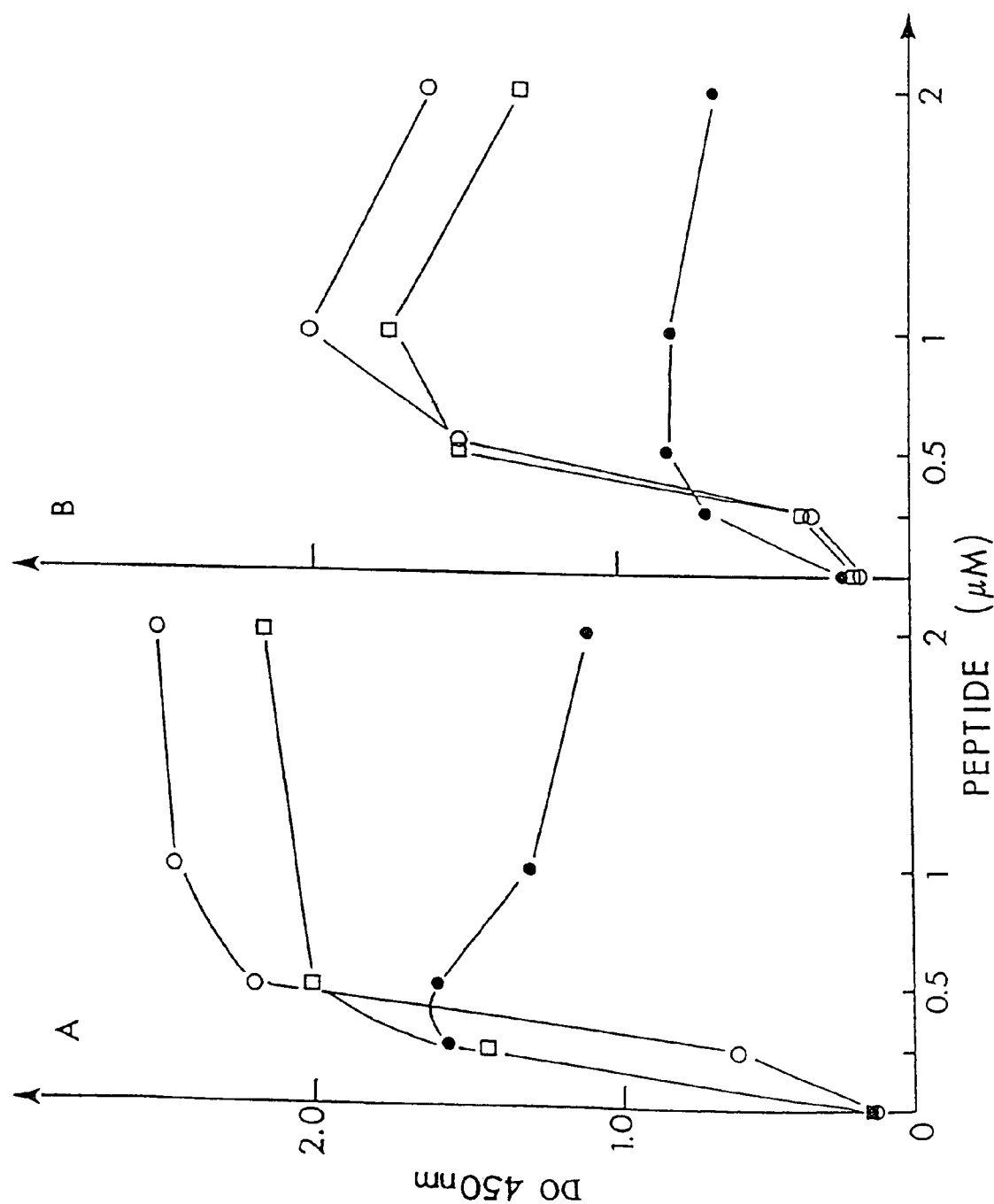

Thirty sera of patients suffering from DLE and SS were first tested for their capacity to react with the parent peptide 277–291 of Ro52, which was previously identified as containing an epitope recognized by antibodies of the subclass IgG of autoimmune patients (Ricchiuti, V., briand, J. P., Meyer, O., Isenberg, D. A., Pruijn, G. and Muller, S. (1994) Epitope mapping with synthetic peptides of 52 kD SSA/Ro protein reveals heterogeneous antibody profiles in human autoimmune sera. Clin. Exp. Immunol., 95: 397–407). Using a threshold value of positivity corresponding to 0.30 OD units (Ricchiuti, V., briand, J. P., Meyer, O., Isenberg, D. A., Pruijn, G. and Muller, S. (1994) Epitope mapping with synthetic peptides of 52 kD SSA/Ro protein reveals heterogeneous antibody profiles in human autoimmune sera. Clin. Exp. Immunol., 95: 397–407), it was found that among these 30 sera 5 contained antibodies of the subclass IgG which react with the L peptide (FIG. 6; microtitration plates sensitized with the peptides at 4° C. instead of 37° C.). The 30 sera (positive or negative with respect to the L peptide) were tested in parallel with the RIa and RIb analogues. It was shown that all the sera positive with the L peptide were also positive with the retro-inverso peptides. The optical density values were significantly higher with the RIb analogue (FIG. 7). Very interestingly, among the 25 sera negative with the L peptide, 10 sera reacted with the RIb peptide (FIG. 6). The mean optical density corresponding to the arithmetic mean of all the optical density values, including the values below the threshold line of positivity, is 0.21 (standard deviation 0.25) and 0.51 (standard deviation 0.62) with the L and RIb peptides respectively.

Competition tests were carried out with the sera of 11 patients showing optical density values greater than or equal to 0.40 with the RIb peptide 277–291 in the direct ELISA test. If the L peptide 277–291 is used as an inhibitor and the RIb peptide is used as the antigen for sensitization of the microtitration plates, it was found that the L peptide had an inhibitory activity in all cases. Depending on the sera tested, up to 75.8% inhibition was found. The homologous peptide tested in parallel under the same conditions inhibited bonding of the antibodies to the RIb peptide to the extent of up to 79.2%.

It was thus demonstrated not only that the RIb peptide 277–291 mimicked the L peptide, but also that it was generally recognized better than the parent peptide by the antibodies of patients. This allowed detection of the presence of anti-peptide 277–291 antibodies in 50% of the sera of patients tested, while only 17% of the sera reacted with the L peptide (FIG. 6).

3.4 Recognition of the Retro-Inverso Peptide Analogue of the Peptide Ro60 304–324 by the Sera of Autoimmune Patients.

The 304–324 region of Ro60 was identified previously as containing a major epitope of the protein (Ricchiuti, V. and Muller, S. (1994) Use of peptides for the mapping of B-cell epitopes recognized by anti-Ro (SS-A) antibodies. In: D. A. Isenberg and A. C. Horsfall (Eds.), Autoimmune Diseases: focus on Sjögren's syndrome. Bios Scientific Publishers, Oxford, p. 101–106). Twenty sera of patients suffering from DLE and SS were first tested with the L and retro-inverso analogues. Six sera (30%) reacted with the L peptide (mean optical density 0.21 standard deviation 0.26), while 15 sera (75%) react with the retro-inverso peptide (mean optical density 0.81, standard deviation 0.54). The sera of the patients reacted slightly better with the retro-inverso D-allo-Ile analogue, as shown on FIG. 8: 16 sera (80%) reacted with the latter analogue (mean optical density 0.81, standard deviation 0.50).

Figure 8:
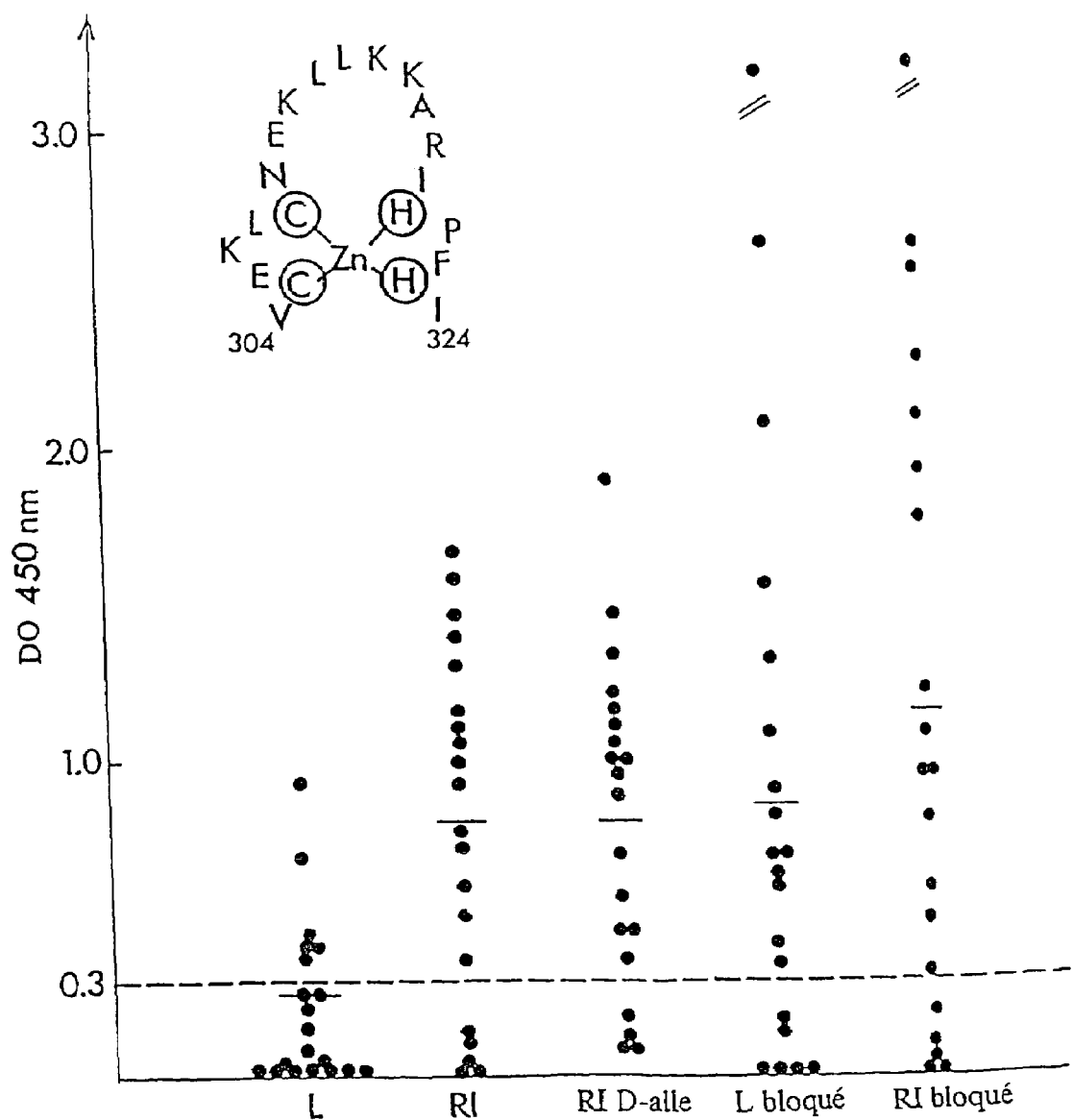

It was then tested whether the Ro60 304–324 peptide analogues with the N-terminal end acetylated and the C-terminal end carboxamidated were recognized by the autoantibodies. When compared with the reactivity obtained with the natural L peptide, it is found that the blocked L peptide is recognized much better by the antibodies of autoimmune patients (FIG. 8). Fourteen sera (70%) reacted with the blocked L peptide (mean optical density 0.86, standard deviation 0.87). The mean optical density and the number of positive sera are also increased by using the retro-inverso analogue with blocked terminal ends ($^{15}/_{20}$ sera positive, i.e. 75%; mean optical density 1.15, standard deviation 0.97). Depending on the sera, the positive reaction with the blocked retro-inverso analogue is still detectable at the serum dilution of 1:4,000. Bonding of the antibodies to the blocked retro-inverso analogue can be inhibited both by the blocked homologous retro-inverso analogue and by the blocked heterologous L peptide.

Figure 9:
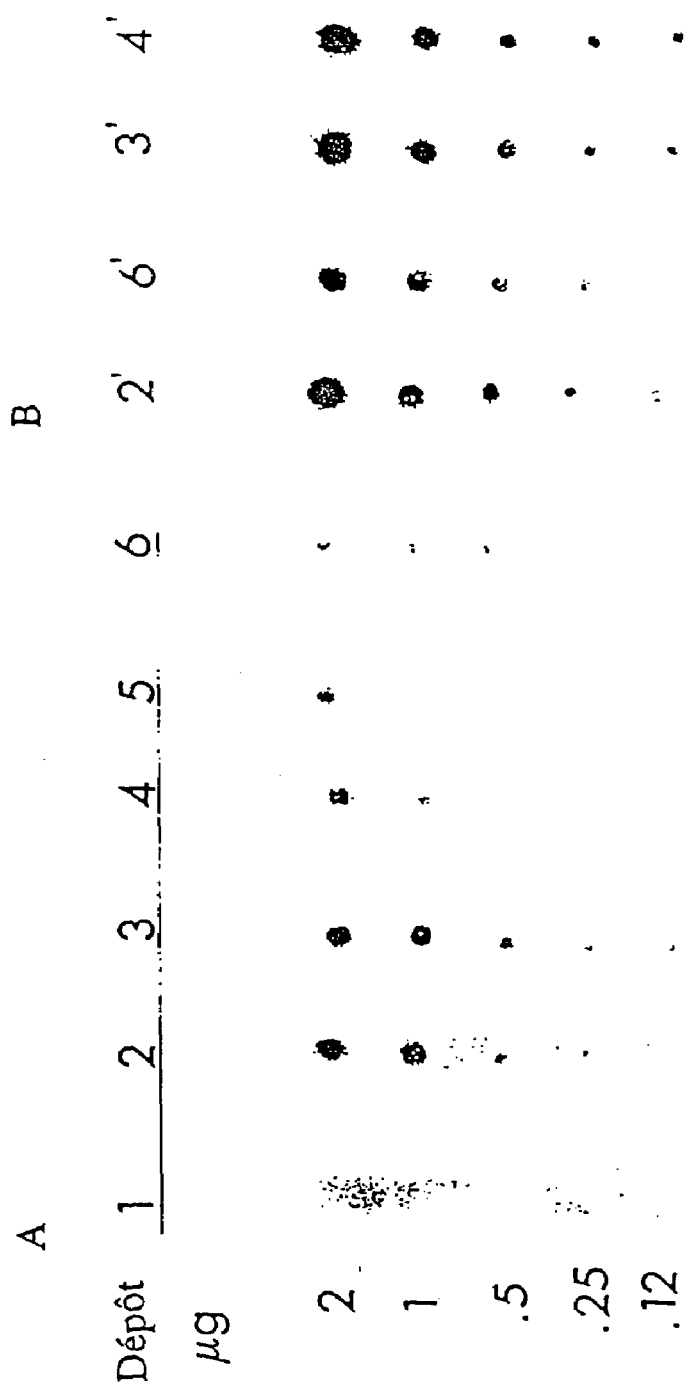

It has been shown very recently that the peptide 304–324 of Ro60 protein, which contains a zinc-finger domain, efficiently bonds radioactive zinc (Muller, S., briand, J. P., Barakat, S., Lagueux, J., Poirier, G., De Murcia, G., and Isenberg, D. A. (1994) Autoantibodies reacting with poly (ADP-ribose) and with a zinc-finger functional domain of poly(ADP-ribose) polymerase involved in the recognition of damaged DNA. Clin. Immunol. Immunopathol., 73: 187–196). It has thus been verified that the peptide analogues, and more particularly the retro-inverso peptides, were capable of bonding $^{65}Zn$. As shown on FIG. 9, the blocked L peptide and also the three retro-inverso analogues bond $^{65}$Zn effectively. This result implies that the retro-inverso analogues, like the natural L peptide, can easily form a finger structure stabilized by a central zinc atom coordinated in a tetrahedral manner using the two cysteine residues and the two histidine residues of the sequence as ligands (residues 305, 309, 320 and 323; FIG. 8).

3.5 Recognition of the Retro-Inverso Analogue of Peptide 28–45 of H3.

The peptide 28–45 of H3 and its retro-inverso analogue were tested with autoimmune sera. In previous studies, peptide 30–45 of H3 was not found to have a significant antigenic activity (Muller, S., and Van Regenmortel, M. H. V. (1993), Histones. In: M. H. V. Van Regenmortel (Ed.), Structure of Antigens, CRC Press, Boca Raton, p. 149–178). 69 sera of patients suffering from various systemic rheumatic diseases, including 22 sera of lupous patients, were tested by ELISA. Among the 69 sera, 12 sera (17.4%) are positive with the natural L peptide 28–45 (8 out of 22 sera DLE), 20 sera (29%) are positive with the blocked L peptide 28–45 (12 out of 22 sera DLE) and 21 sera (30.4%) react with the blocked retro-inverso analogue (12 sera out of 22 sera DLE).

3.6 Recognition of the Retro-Inverso Analogue of Peptide C18L of the Haemagglutinin of the Influenza Virus.

The 3 peptides (parent L-peptide C18L, double blocked L-peptide *C18L* and double blocked retro-inverso peptide) are substantially recognized in the same way by the tested antibodies (FIGS. 14 and 15).

3.7 Recognition of the Retro-Inverso Analogue of Peptide 9B1 of *Schistosoma mansoni*.

The double blocked retro-inverso peptide is better recognized than the double blocked L-peptide by the antibodies (FIGS. 16 and 17).

4. Discussion.

In the context of this invention, the possibility of using retro-inverso peptides instead of natural linear L peptides for detection of antibodies in the serum of autoimmune patients is shown. In all the cases examined in this work (antigenic regions 28–45 and 130–135 of H3, 277–291 of Ro52 and 304–324 of Ro60) it has been found that the retro-inverso peptides have an antigenic activity at least equal to or greater than that of the natural enantiomeric L peptide. This has allowed further detection of positive sera which react with each peptide, and in general a significant increase in the optical density values of individual sera with respect to peptide probes, without changing the threshold value of positivity determined with normal sera. It should be noted that the antibodies which react with the retro-inverso peptides do not constitute a sub-group of particular antibodies present in the sera of patients, given that bonding of the antibodies of patients to the retro-inverso analogues is inhibited just as much by the L peptides a by the retro-inverso peptides. This new development of retro-inverso peptides in diagnosis is therefore very promising.

As has been elaborated widely above, the success of this approach rests on perfect control of the probe peptides. It is therefore appropriate to pay particular attention to the inversion of the charges of the ends which may alter the antigenic reactivity of the retro-inverso peptides. For example, many of the enantiomers of biologically active peptides described in the literature for use in pharmacology are not active at all. A certain number of approaches have been proposed to bypass this problem (Goodman, M., and Chorev, M. (1979) On the concept of linear modified retro-peptide structures. Acc. Chem. res. 12: 1–7; (Chorev, M., and Goodman, M. (1993) A dozen years of retro-inverso peptidomimetics. Acc. Chem. Res., 26: 266–273). For example, a gem-diaminoalkyl residue can be introduced at the N-terminal end of the retro-inverso peptide and malonic acid substituted in the 2-position may be introduced at the carboxy-terminal end. However, monoacyl-gem-diaminoalkyls are hydrolysable, and it must be expected from this that the half-life of peptides including such residues will be 10 to 50 hours at 25° C. (Loudon, G. M., Merrick, R. A. and Jacob, J. N. (1981) Mechanism of hydrolysis of N-(1-aminoalkyl) amides. J. Am. Chem. Soc., 103: 4508–4515). Consequently, in the case of retro-inverso peptides 130–135 of H3 and 277–291 of Ro52, a carboxamide termination was chosen instead of a free amino group of the parent peptides. The malonic acid substituted on C-2 is incorporated into these peptides in the form of the racemate to mimic the C-terminal end of the L peptides. It should be noted that in the case of the retro-inverso analogue of Ro60 304–324, it was found that the retro-inverso analogue with non-blocked inverted terminal ends was recognized better than the L peptide (FIG. 8), suggesting that for this particular peptide, inversion of the terminal groups does not affect its antigenicity.

In comparison with the parent peptides with free N- and C-terminal ends, it was found that the blocked peptides 304–324 of Ro60 and 28–45 of H3 are recognized better by the antibodies of autoimmune sera. This may be correlated with the fact that the antibodies are probably induced to proteins complexed with other proteins or with nucleic acids (DNA or RNA). If the internal sequences in the primary structure of the protein are recognized specifically by the autoantibodies, it may be that the peptides containing blocked amino and carboxyl groups mimic the internal region of the protein better (Gras-Masse, H. S., Jolivet, M. E., Audibert, F. M., Beachey, E. H., Chedid, L. A. and Tartar, A. L. (1986) Influence of COHN$_2$ or COOH as C-terminus groups on the antigenic characters of immunogenic peptides. Molec. Immunol., 23: 1391–1395). In correlation with that stated above regarding the presence of inverted terminal ends in the blocked retro-inverso analogues, it was found again that inversion of the terminal ends has no effect on the antigenicity. However, it is advisable to check this result for any new peptide tested.

The presence of threonine and isoleucine residues which contain two chiral centres may also present a problem in observing the correct chirality of the retro-inverso compound. The peptide Ro60 304–324 contains two isoleucine residues in positions 319 and 324, and two retro-inverso analogues were synthesized with D-Ile and with D-allo-Ile, and it was found that the retro-inverso D-allo-Ile analogue was recognized slightly better by the antibodies of patients than the retro-inverso analogue containing the D-Ile residues. However, it should be noted that the two peptides 277–291 of Ro52 and 28–45 of H3 contain 2 threonine residues, and this apparently does not seem to affect their antigenic activity.

Finally, in the case of peptides containing proline residues, the retro-inverso analogue may present local conformation restraints at this level (Goodman, M., and Chorev, M. (1979) On the concept of linear modified retro-peptide structures. Acc. Chem. Res. 12: 1–7; (Chorev, M., and Goodman, M. (1993) A dozen years of retro-inverso peptidomimetics. Acc. Chem. Res., 26: 266–273), which may influence bonding of the retro-inverso peptide to the antibody. Given that the retro-inverso peptide of Ro60 304–324, which contains a proline residue in position 321, is recognized very well by the autoantibodies and can effectively bond zinc, this suggests that this proline residue 321 in the zinc-finger domain (FIG. 8) serves solely to keep the 2 histidine residues at a suitable difference, and that it compromises neither bonding of metallic ions nor interactions with antibodies.

TABLE 6

Primary sequence of the four antigenic domains studied by means of the natural L peptides and the retro-inverso analogues[1].

C-terminal peptide 130–135 of histone H3 (6 residues)[2]
L peptide

H-Cys → Gly → Gly → Ile → Arg → Gly → Glu → Arg → Ala-OH (SEQ ID NO:5)
RI peptide H$_2$N-D-Cys ← Gly ← Gly ← D-Ile ← D-Arg ← Gly ← D-Glu ← D-Arg ← R,S-mAla-OH
Internal domain 277–291 of 52kD SSA/Ro (Ro52) protein (15 residues)
L peptide (SEQ ID NO:10)

H → Gly → Leu → Lys → Lys→ Nle → Leu → Arg → Thr → Cys → Ala → Val → His → Ile → Thr → Leu → OH
RIa and RIb peptides H$_2$N-Gly ← D-Leu ← D-Lys ← D-Lys ← D-Nle ← D-Leu ← D-Arg ← D-Thr ← D-Cys ← D-Ala ← D-Val ← D-His ← D-Ile ← D-Thr ← (R,S)-mLeu-OH
Internal domain 304–324 of 60kD SSA/Ro protein (21 residues)
L peptide (SEQ ID NO:11)

H-Val → Cys → Glu → Lys → Leu → Cys → Asn → Glu → Lys → Leu → Leu → Lys → Lys → Ala → Arg → Ile → His → Pro → Phe → His → Ile-OH
RI peptide HO-D-Val ← D-Cys ← D-Glu ← D-Lys ← D-Leu ← D-Cys ← D-Asn ← D-Glu ← D-Lys ← D-Leu ← D-Leu ← D-Lys ← D-Lys ← D-Ala ← D-Arg ← D-Ile ← D-His ← D-Pro ← D-Phe ← D-His ← D-Ile-H
RI D-allo-Ile peptide HO-D-Val ← D-Cys ← D-Glu ← D-Lys- ← D-Leu ← D-Cys ← D-Asn ← D-Glu ← D-Lys ← D-Leu ← D-Leu ← D-Lys ← D-Lys ← D-Ala ← D-Arg ← D-a-Ile ← D-His ← D-Pro ← D-Phe ← D-His← D-a-Ile-H
Blocked L peptide CH$_3$CO-Val → Cys → Glu → Lys → Leu → Cys → Asn → Glu → Lys → Leu → Leu → Lys → Lys → Ala → Arg → Ile →
His → Pro → Phe → His → Ile-NH$_2$
Blocked RI peptide H$_2$N-D-Val ← D-Cys ← D-Glu ← D-Lys ← D-Leu ← D-Cys ← D-Asn ← D-Glu ← D-Lys ← D-Leu ← D-Leu ← D-Lys ← D-Lys ← D-Ala ← D-Arg ← D-Ile ← D-His ← D-Pro ← D-Phe ← D-His ← D-Ile-COCH$_3$
Internal domain 28–45 of histone H3 (18 residues)
L peptide (SEQ ID NO:12)

H-Ser → Ala → Pro → Ala → Thr → Gly → Gly → Val → Lys → Lys → Pro → His → Arg → Tyr → Arg → Pro → Gly → Thr-OH
Carboxamidated L peptide H-Ser → Ala → Pro → Ala → Thr → Gly → Gly → Val → Lys → Lys → Pro → His → Arg → Tyr → Arg → Pro → Gly → Thr-NH$_2$
Blocked L peptide CH$_3$CO-Ser → Ala → Pro → Ala → Thr → Gly → Gly → Val → Lys → Lys → Pro → His → Arg → Tyr → Arg → Pro → Gly → Thr-NH$_2$
Blocked RI peptide H$_2$N-D-Ser ← D-Ala ← D-Pro ← D-Ala ← D-Thr ← Gly ← Gly ← D-Val ← D-Lys ← D-Lys ← D-Pro ← D-His ← D-Arg ← D-Tyr ← D-Arg ← D-Pro ← Gly ← D-Thr-COCH$_3$

[1]The arrows indicate the direction of the CO-NH bond in the peptide skeleton.
[2]A CGG sequence is added during the synthesis to enable the peptide to be conjugated to the carrier protein by its thiol group by means of SPDP.

TABLE 7

ELISA reactivity of sera of lupous mice with the natural C-terminal peptide 130–135 of histone H3 and with the retro-inverso peptide.

| Mice (NZB/W) F1 | L peptide | Retro-inverso peptide | Wells without antigen |
|---|---|---|---|
| 11/3 | >3 | >3 | 0.07 |
| 33/1 | 1.92 | 2.12 | 0.15 |
| 33/2 | 2.22 | 2.70 | 0.14 |
| 33/5 | 0.39 | 0.41 | 0.08 |
| 66/2 | 0.97 | 0.63 | 0.13 |
| 22/5 | 0.12 | 0.10 | 0.11 |

EXAMPLE 3

Retro-Inverso Peptides and Vaccine

By way of illustration in the field of vaccination, the invention more particularly relates to totally retro-partly inverso peptides corresponding to the major antigenic determinant situated on the protein $VP_1$ of the virus of aphthous fever (foot-and-mouth disease virus, FMDV).

Aphthous fever remains one of the main diseases affecting animals such as cattle, sheep and goats, and may give rise to considerable economic losses. Although this disease rarely causes the death of the animal, production losses remain very high and the numerous after-effects necessitate slaughter of the animals.

FMDV belongs to the family of Picornaviridae, which is a collective name for the simplest viruses known. Only a chemical approach has enabled the exact structure of FMDV to be understood: the envelope is made up of a combination of 60 copies of each of the 4 proteins called $VP_1$, $VP_2$, $VP_3$ and $VP_4$. It is now known that it is protein $VP_1$ which triggers synthesis of neutralizing antibodies (Ab).

Vaccines exist conventionally in two forms, attenuated or inactivated, but their preparation and their handling present many disadvantages. For some time, a new generation of more reliable and more stable vaccines than the traditional products has been about to be revealed. Thus, in the case of FMDV, several groups of researchers have studied the possibility of producing significant quantities of the protein $VP_1$ by means of genetic engineering techniques. However, the doses needed to induce protection in cattle, as for the natural protein $VP_1$ isolated from viral particles, is still too high.

In parallel, another proposed approach has constituted imitation of the fragment 141–160 of the protein $VP_1$ by chemical synthesis. This fragment in fact corresponds to a particular region of the protein $VP_1$, to which the neutralizing antibody(bodies) attach(es) specifically. On the other hand, this same peptide coupled to a carrier protein induces an immune response in the guinea-pig such that the immunized animal is protected against aphthous fever (these animals are a very good biological model for study of the disease). It has been found that a single injection of conjugated peptide was sufficient to protect infected animals.

However, fundamental research is still necessary to provide these synthetic peptides with their entire effectiveness as vaccines. In fact, it often proves to be difficult or even impossible to obtain sufficient neutralizing titres of anti-peptide Ab. This could be related to the problems relating to stabilization of an "optimum" conformation of a linear sequence, as well as to the rapid degradation of peptides injected into the animal. In the context of the invention, a study of the antigenic and immunogenic properties of retro-inverso (RI) analogues derived from the immunodominant loop of three variants of serotype A12 of FMDV was therefore undertaken. The sequences of these peptides and of the corresponding RI analogues are shown on Table 8 (note: the parent sequence of the peptide studied covers the region 141–159; a cysteine residue is added in the N-terminal position at the end of coupling).

TABLE 8

Sequences of synthetic peptides (region 141–159) derived from the immunodominant loop of three variants of serotype A12 of the virus of aphthous fever (FMDV).

FP peptide C-G$^{141}$-S-G-V-R-G-D-F-G-S-L-A-P-R-V-A-R-Q-L$^{159}$
(strain USA) (SEQ ID NO:7)
FL peptide C-G$^{141}$-S-G-V-R-G-D-F-G-S-L-A-L-R-V-A-R-Q-L$^{159}$
(SEQ ID NO:8)
SL peptide C-G$^{141}$-S-G-V-R-G-D-S-G-S-L-A-L-R-V-A-R-Q-L$^{159}$
(strain A) (SEQ ID NO:9)
Sequences of the corresponding retro-inverso analogues
HO-m(R or S)Leu-q-r-a-v-r-(*)-a-l-s-G-()-d-G-r-v-G-s-G-c-NH$_2$ (): f f s
(*): p l l The study is divided into 3 parts:

1) Study of the Anti Genic Properties of the Analogues.

Sera of guinea-pigs immunized against the virus ("anti-virion"), protein $VP_1$ ("anti-protein $VP_1$"), against peptide 141–159 (variant USA; "anti-FP peptide") and serum originating from guinea-pigs infected with the virus ("convalescent") are available. Normal serum (negative batch) of the guinea-pig serves as a control. The results are shown on Table 9. The two RIa and RIb diastereomers were separated, purified by HPLC and tested separately in ELISA. The RI isomer eluted fastest by HPLC is called RIa, and the 2nd peak eluted (isomer eluted slowest) comprises the isomer called RIb. Only the results with the FP system are shown.

It will be noted that the RI analogues are recognized as well as and often better than the parent FP-L peptide. The results are analogous in the case of the FL and SL peptides.

Inhibition studies were carried out in the BIAcore system. Table 10 shows the amounts of analogues which are necessary to inhibit by 50% the bonding of the various antibodies to the parent FP-L peptide immobilized on the dextran matrix (by cysteine). In this series of experiments, the effect of the position of the cysteine in N-t or C-t and the effect of blocking the C-t end or the 2 N- and C-t ends were studied.

It will be noted that the blocked or non-blocked RI analogues are all competitors which are as good as the parent FP-L peptide.

TABLE 9

ELISA reactivity with the parent peptide and the retro-inverso analogues of anti-peptide 141–159 (FMDV, serotype A12, variant U.S.A.), anti-protein $VP_1$ and anti-virion antisera of guinea-pigs, and of convalescent guinea-pig sera

| | | Peptides (0.2 μM) | | | |
|---|---|---|---|---|---|
| Sera | Dilution serum | FP-L | FP-RIa | FP-RIb | No Ag |
| normal | 1/5,000 | 0.06 | 0.04 | 0.11 | 0.02 |
| anti-FP peptide | 1/20,000 | 1.24 | 1.22 | 2.41 | 0.09 |
| anti-protein $VP_1$ | 1/20,000 | 1.09 | 1.57 | 1.22 | 0.01 |

TABLE 9-continued

ELISA reactivity with the parent peptide and the retro-inverso analogues of anti-peptide 141–159 (FMDV, serotype A12, variant U.S.A.), anti-protein $VP_1$ and anti-virion antisera of guinea-pigs, and of convalescent guinea-pig sera

| | | Peptides (0.2 µM) | | | |
|---|---|---|---|---|---|
| Sera | Dilution serum | FP-L | FP-RIa | FP-RIb | No Ag |
| anti-virion | 1/20,000 | 0.86 | 1.23 | 2.47 | 0.01 |
| convalescent | 1/20,000 | 1.23 | 2.31 | 1.91 | 0.01 |

| non-conjugated peptide 0.2 µM coating at 4° C. for 1 night | PBS-T-gelatin 3% 1 h; 37° guinea-pig serum various dilutions diluted in PBS-T-gelatine 1% 1 h, 37° C. | conjugated anti guinea-pig IgG coupled to peroxidase 30 min, 37° C. | substrate: $TMB/H_2O_2$ 15 min, 37° C. TMB = tetramethyl-benzidine | reading at 450 nm |

TABLE 10

Recognition in the BIAcore competition test of FP peptide and analogues by polyclonal antibodies

| Guinea-pig antiserum | Amount of inhibitor peptides (in µg) required to inhibit by 50% bonding of the antibodies to the (c) FP-L peptide | | | | | | |
|---|---|---|---|---|---|---|---|
| | (c) FP-L | (c) FP-RIa | (c) FP-RIb | FP(c)-L | FP* (c)-L | *FP* (c)-L | *FP* (c)-RI |
| anti-FP peptide | 25 | — | 25 | 25 | 25 | 20 | 20 |
| anti-protein VP1 | 40 | 30 | 130 | 55 | 40 | 150 | 30 |
| convalescent | 25 | 25 | 25 | 25 | 20 | 20 | 20 |
| | 30 | 25 | 120 | 50 | 40 | 140 | 25 |

The guinea-pig antisera were diluted to 1:10
*blocked ends (acetyl N-t; carboxamide C-t)
Principle of the test  antiserum + competition peptides
(various concentrations)
FP-L 2) Study of the Immunogenic Properties of the Analogues.

The parent (L) peptide and the RIa and RIb analogues were injected into rabbits and the ELISA response with respect to the homologous peptides was measured.

The results are shown with the FL peptide on Table 11. It will be noted that the FL-RIb peptide induced antibody titres 8 times higher in the "Cannes" rabbit. Furthermore, even though the animal was no longer reimmunized, the titre falls slowly in the "Cannes" rabbit, whereas it falls very quickly in the anti-FL-L peptide rabbits ("Antibes"), reaching zero at day 143 (at the same time, the antibody titre in the "Cannes" rabbit is still 6,000).

TABLE 11

ELISA test on the sera of rabbits immunized against the parent FL peptide and the RI analogues of FL peptide.

| Blood sampes (2) | | Antibes rabbit Anti-FL-L/FL-L | Romarin rabbit Anti-FL-RIa/ FL-RIa | Cannes rabbit Anti-FL-RIb/ FL-RIb |
|---|---|---|---|---|
| 1 | days  23 | 0 (3) | 250 | 4,000 |
| 2 | 37 | 4,000 | 6,000 | 6,000 |
| 3 | 52 | 8,000 | 16,000 | 100,000 |
| 4 | 64 | 24,000 | 24,000 | 200,000 |
| 5 | 78 | 550 | 4,000 | 64,000 |
| 6 | 113 | 275 | 500 | 48,000 |
| 7 | 143 | 0 | 0 | 6,000 |
| 8 | 173 | 0 | 0 | 1,000 |
| 9 | 203 | 0 | 0 | 0 |

(1) The rabbits were immunized on days 0, 14, 30, 43 and 58 with the peptide analogues (60 µg/injection) coupled covalently to small unilamellar liposomes containing monophosphoryl-lipid A as an adjuvant (subcutaneous injections).

(2) Days after the first injection.

(3) The values are expressed as titres (the highest dilution of serum at which the ELISA absorbance value is 1.0). The blood samples are tested by ELISA using 2 µM of peptide-BSA conjugates to sensitize the plates.

Principle of the test:

| peptides coupled to BSA by cysteine (by means of SPDP) 2 µM one night at 37° C. | anti-peptide serum variable conc. 1 h, 37° C. | anti-rabbit IgG peroxidase 1:40,000 30 min, 37° C. | $TMB/H_2O_2$ 15 min, 37° C. |

SPDP=N-succinimidyl-3-(2-pyridyldithio)propionate

The recognition of the various analogues by the rabbit anti-peptide antibodies were tested by the same principle as that shown on Table 10 using the analogues in solution in the BIAcore system (Table 12, competition test).

TABLE 12

Recognition in a BIAcore competition test of FL peptide and analogues by the polyclonal antibodies.

| Rabbit antisera | Amount of inhibitor peptides (in µg) required to inhibit by 50% bonding of the antibodies to the (c) FL-L peptid | | | | | |
|---|---|---|---|---|---|---|
| | (c) FL-L | (c) FL-RIa | (c) FL-RIb | (c) FP-L | (c) FP-Ria | (c) FP-RIb |
| Antibes [anti-(c) FL-L] | 80 | 80 | 60 | 85 | 70 | 60 |
| Cannes [anti-(c) FL-RIb] | 25 | 60 | 50 | 30 | 60 | 50 |

The rabbit antisera were diluted to 1:2.

It is noted that the anti-FL Ab recognized the peptides of the FL series and of the FP series equally well, and that there is a cross-reaction between the L, RIa and RIb peptides of the two series FL and FP.

3) Study of the Immunogenic Properties of the Analogues: Neutralizing Response.

The L and RIb FP peptides were injected into guinea-pigs and the neutralizing response on the virus was measured in vitro. The preparations used correspond to peptide analogues bonded to liposomes of the small unilamellar liposome type prepared by the process described by Benkirane et al. (J. Biol.

Chem., 268: 26279–26285, 1993). The neutralization test was carried out by the method of Francis and Black (1983) J. Hyg. Camb., 91: 329–334. The results are shown on Table 13.

TABLE 13

Results of in vitro neutralization of the 1st and 2nd blood sample (3 animals per peptide)

| | 1st blood sample | 2nd blood sample |
|---|---|---|
| FP-L | zero | 1.0 |
| | 1.0 | 2.0 |
| | zero | — |
| FP-RI | 0.5 | 1.0 |
| | 0.5 | 1.5 |
| | 0.5 | 2.5 |

1st injection: d0
1st blood sample: d20
2nd injection: d43
2nd blood sample: d74

The results are expressed as $\log_{10}$ and correspond to the difference between the titre of the virus incubated with normal serum and that of the virus incubated with serum of the immunized guinea-pig (dilution of the sera 1/20).

The tests were carried out in the laboratory of Professor F. Brown (American Department of Agriculture, Centre for Animal Diseases of Plum Island, Greenport, N.Y. 11944, USA).

It is noted that the effectiveness of the FP-L peptide is similar to that of the same peptide described previously (Rowlands et al., Nature, 306: 694–697, 1983) and that these results are reproduced entirely with the RI FP peptide.

Other results obtained in induction of neutralizing antibodies are given hereafter.

The in vitro neutralization titers of the sera taken at various intervals were followed for 362 days. The animals received a single dose of 100 µg of peptide with aluminium hydroxyde gel as adjuvant. The results showed that the level of the response to the retro-inverso peptide $NH_2$—(C)141–159—OH was similar to that obtained with the L-peptides H—141–159(C)—$NH_2$ and H—(C)141–159—OH up to around 50 days after the inoculation. However, compared with the response to the L-peptides, the response against retro-inverso $NH_2$—(C)141–159—OH peptide continued to increase beyond 50 days (the neutralizing indices are at least 10-fold higher at 100 days). In the samples collected 262 days after inoculation of the animals, the neutralizing indices of the sera from guinea pigs that received the retro-inverso peptide were still significantly higher than those of the sera from responder animals inoculated with the L-peptides.

4) Protection of Swine from Foot-And-Mouth Disease with One Dose of the All-D Retro Peptide Corresponding to the Immunodominant GH Loop Encompassing Residues 141–159 of Capsid Protein VP1 of Foot-And-Mouth Disease Virus Serotype A, Sub-Type12 (FP peptide).

It has been shown that the retro-inverso FP peptide (serotype A) allows to obtain good results in the pig vaccination. The summary of the obtained results are given below.

Nine pigs were given a single inoculum of 100 μg of the retro-inverso peptide corresponding to the immunodominant GH loop encompassing residues 141–159 of capsid protein VP1 of foot-and-mouth disease virus serotype A, sub-type 12. The peptide was conjugated to activated keyhole limpet haemocyanin and oil-adjuvanted before inoculation. The animals were challenged eleven weeks post-vaccination by exposing them to a pig which had been infected with the virus by inoculation. Two naive animals were included in the challenge study as controls. One of the vaccinated animals was completely unprotected and two developed very small lesions. None of the six remaining animals exhibited any clinical signs but two developed antibodies against non-structural proteins indicating that replication of the virus had occurred. No evidence of replication could be detected in the remaining four animals, either by rise in neutralizing antibody titre or by production of antibodies against non-structural proteins specific for virus replication.

EXAMPLE 4

Therapeutic Immunomodulation

The phenomenon of TCR (T cell receptor) antagonism by peptide analogues of the T epitopes has recently been shown and the use of specific TCR antagonists has been described (De Magistris, M. T., Alexander, J., Coggeshall, M., Altmon, A., Gaeta, F. C. A., Grey, H. M. and Sette, A. (1992) Cell 68: 625). These peptides are capable of inhibiting proliferation of T cells induced by an antigen. Such antagonist peptides are obtained by replacement of an amino acid among the antigen peptide residues in contact with the T cell, or by incorporation of residues in contact with the TCR into a sequence of poly-alanines.

The present invention maintains its originality in the fact that it relates precisely to the use of immunoretroids corresponding to TCR-agonist or -antagonist peptides to obtain "medicaments" intended for viral treatment (agonist effect on suppressive T cells) or for treatment of autoimmune diseases (antagonist effect on the auxiliary or "helper" T cells, for example).

EXAMPLE 4A

Figure 10:
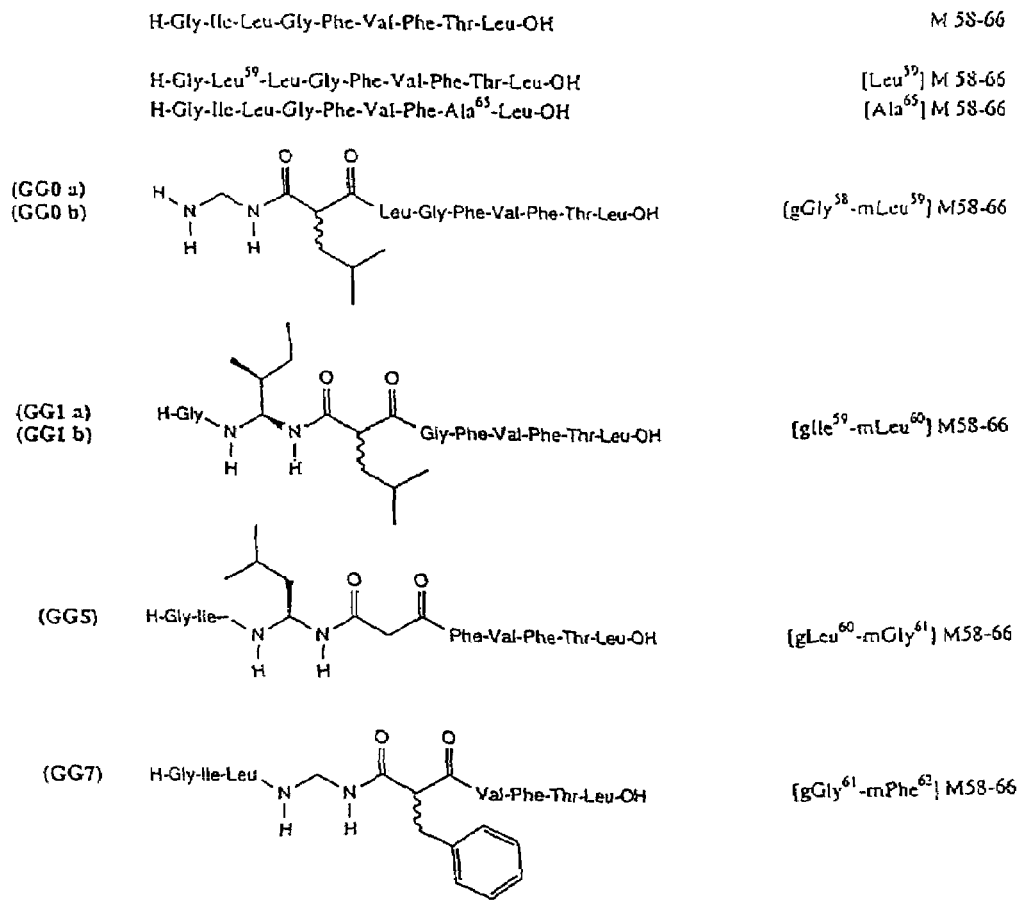
FIG. 10 shows the list of peptides synthesized for the therapeutic immunomodulation tests (wherein Gly Ile Leu Gly Phe Val Phe Thr Leu is (SEQ ID NO:3); Gly Leu Leu Gly Phe Val Phe Thr Leu is (SEQ ID NO:19); and Gly Ile Leu Gly Phe Val Phe Ala Leu is (SEQ ID NO:20)).

The partly retro-inverso immunoretroids of a cytotoxic T epitope (epitope 56–68) of the matrix of the influenza virus recognized by the molecule HLA-A2 (molecule of class I) has been taken as an example. In this work, the amide bonds of the parent peptides were replaced systematically, one by one, by retro-inverso bonds. The pseudopeptides used in this study were synthesized by the solution methodology as described above. The list of these peptides is shown on FIG. 10. The terminology a, b has been used if the two optical isomers could be separated by HPLC. On FIG. 10, the content of the parentheses preceding M58–66 indicates the position of the retro-inverso bond. By way of example, for the peptide GG5, [gLeu$^{60}$–mGly$^{61}$] M58–66 means that the retro-inverso bond is between amino acid 60 and amino acid 61. It should be noted that if the retro-inverso bond relates to Gly-Ile, Ile has been replaced by Leu (cf. peptides GG0a and GG0b), and if the retro-inverso bond relates to Phe-Thr, Thr has been replaced by Ala (cf. peptide GG11), for easiness of synthesis, given that this mutation does not affect bonding to the HLA molecule.

The interaction of each immunoretroid with the molecule presenting the peptide HLA-A2 was first studied, and each peptide capable of bonding was then tested for its capacity for inhibition or activation of the cytotoxic T response.

The first test (test of bonding of the peptides to the molecule HLA-A2) is carried out as follows:

1. Source of HLA-A2

1.1 From the T2 Cell Line.

T2 is a variant of the T1 line produced by fusion of a T lymphoma cell (CEM) and of a lymphoblastoid B cell line (721.174). Virtually no HLA molecules of class I are detected on the surface of the T2 by immunofluorescence. This is due to a mutation causing the absence of peptide carriers in the endoplasmic reticulum. As there are no peptides to stabilize the combination of the heavy chain and β2microglobulin (β2m), apart from perhaps a few endogenous signal peptides, these cells are regarded as an excellent source of "empty" HLA molecules of class I ready to receive exogenous peptides in their acceptor site.

By adding exogenous peptide, the HLA molecules are stabilized.

1.2 From purified HLA Molecules.

1.2.1 Purification of HLA Molecules of Class I.

The HLA molecules were purified on an affinity column starting from lymphoblastoid B cells immortalized by the Epstein-Barr virus (EBV). For this, the cells were lysed in a buffer of 50 mM Tris-HCl, 150 mM NaCl, 5 mM EDTA (ethylenediaminetetraacetic acid) and 0.5% Nonidet P40 (NP40), containing protease inhibitors. The lysates were then passed over a series of columns on which are fixed anti-HLA antibodies. The molecules of MHC fixed on these affinity columns were collected by elution at a basic pH.

1.2.2 Denaturation of the HLA Molecules of Class I.

The purified HLA molecules of class I should be "emptied" of their endogenous peptides before they can be tested for linkage with the exogenous peptides. For this, denaturation is carried out with 12.5 mM NaOH, 1.5 mM urea and very pure bovine serum albumin (BSA) (Sigma) 1%, for 1 h at 4° C. The heavy chains are recovered after passage of the denatured HLA molecules over a column of G25/PD10 Sephadex (Pharmacia). The peptides which could reform a tri-complex with the heavy chain and the β2m are removed by retention in the column. The light chains of β2m (12 kd) should leave the column with the heavy chains (exclusion<10 kd), but since some are potentially retained, exogenous β 2m (2 μg/ml, SIGMA) is added secondarily.

2. Antibodies.

The following monoclonal antibodies were used to trap the heavy chains of the HLA molecules in the course of the affinity chromatography stages and during point 3. below:

W6/32 and B9.12.1, which are antibodies to all types of HLA but which recognize distinct epitopes,
B1.23.2 for the HLA-B,
BB7.2, specific to HLA-A2,
A111.1, specific to HLA-A3, A11 and A24,
M28, which recognizes β2m.

3. Detection of the HLA-Peptide Linkage.

With cells deficient in peptide carriers: 800,000 cells were lysed for 1 h at 37° C. in a buffer of 50 mM Tris-HCl, 150 mM NaCl, 5 mM EDTA and 0.5% Nonidet P40, with protease inhibitors in the presence or absence of exogenous peptide at the desired concentration. After centrifugation, the supernatants were collected and made up to 200 μl with phosphate-buffered saline (PBS) of 0.05% Tween, 1% BSA, 1 mM PMSF (phenylmethylsulphonyl fluoride) and 10 mg/ml of trypsin inhibitor (TI).

With purified and denatured HLA: aliquot fractions of 1 μg of HLA were incubated in the presence or absence of exogenous peptide at the desired concentration for 24 or 48 h at 4° C. The renaturation products were made up to a volume of 200 μl with PBS of 0.05% Tween, 1% BSA, 1 mM PMSF and 10 mg/ml of TI.

In all cases, the samples were deposited for one night at 4° C. in duplicate in an amount of 100 μl in the wells of microplates sensitized with monoclonal antibodies specific to the heavy chains of the HLA studied. These antibodies had been immobilized beforehand in an amount of 10 μg/ml in PBS for 2 h at 37° C. or overnight at 4° C., and saturation was then achieved with PBS containing 1% BSA for 1 h at 22° C.

Since fixing of the β2m to the heavy chain of an HLA takes place only if a peptide is present to stabilize the complex, only the HLA bonded to a peptide due to the M28 antibody is revealed. This anti-β2m antibody is coupled to the alkaline phosphate. The presence of the enzyme, and thus of the antibody, was revealed by its action on the substrate 4-methylumbelliferyl-P (MuP, Sigma), which is transformed into methylumbelliferone. The latter emits a fluorescence signal when excited at $^{405}/_{492}$ nm. The signal was read with a Fluoscan apparatus (Millipore).

Figure 11:
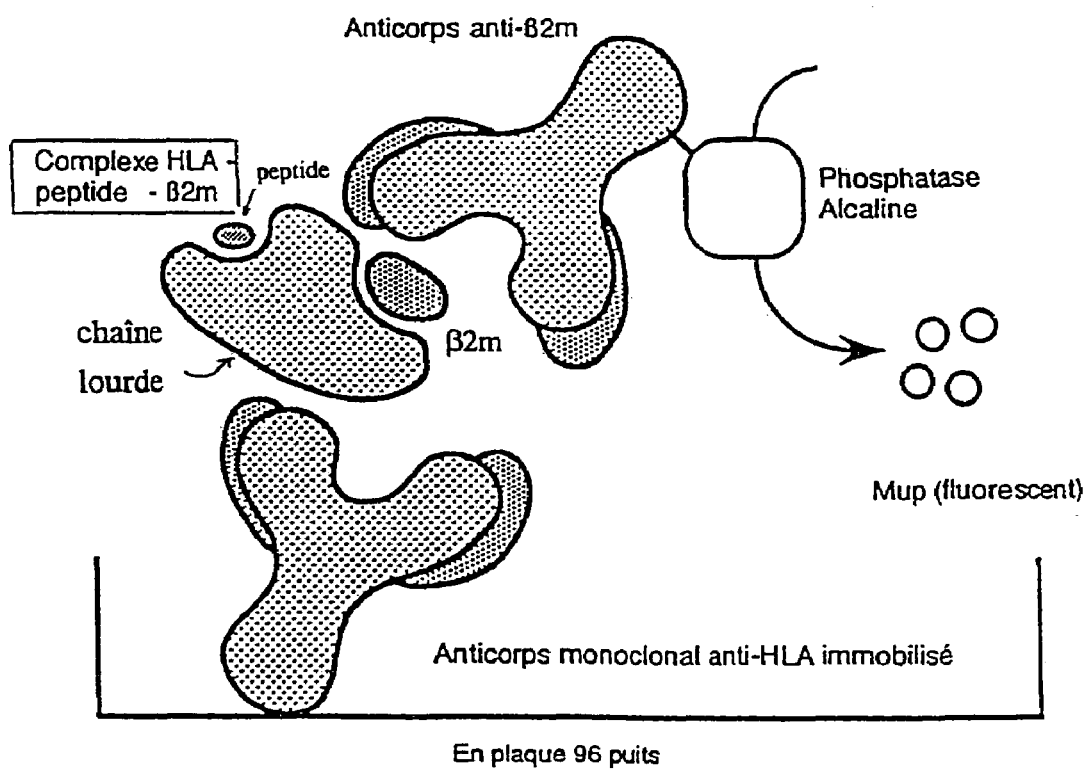
FIG. 11 shows a diagram of the principle of detection of the HLA-peptide linkage.

FIG. 11 summarizes the detection principle.

The results are shown on FIG. 12: it can be seen that the retro-inverso peptide GG0a is at least as active as the parent peptide M58–66 (the Leu 59 and Ala 65 peptides which contain the changes Ile→Leu in position 59 and Thre→Ala in position 65 are also very active). The RI GG0b, GG7, GG10 and GG11 analogues are slightly less active, but bond significantly to the HLA-A2 molecule. The other RI analogues (GG1, GG5, GG8 and GG12) do not bond to the HLA-A2 molecule.

To be effective in immunomodulation, it is not sufficient for a peptide to bond to the HLA molecule, and it must also be recognized by the TCR. The second test is therefore a biological test, the principle of which is as follows:

| EFFECTOR: | TARGET: |
|---|---|
| T lymphocytes of an individual of type HLA A2 having recently had influenza (cells stimulated several times by the peptide 58–66 in the presence of irradiated B and T cells) | T lymphocytes of the same donor treated with Epstein-Barr virus + peptides<br>1 μg/ml<br>GG0a<br>GG10<br>GG7 |
| mixture of the effector and the target measurement of the cytolysis | |

The results are shown on FIG. 13: the peptide GG0a is at least as effective as (if not more than) the parent peptide M58–66 in inhibiting cytolysis. The peptide GG10 is less effective. The peptide GG7 does not induce cytolysis. The latter peptide is thus just as interesting as GG0a. It is deduced that GG0a seems to be a very good agonists of cytolysis and that GG7 could be an antagonist of cytolysis.

EXAMPLE 4B

The retro-inverso analogue of the parent L-peptide 103–115 of poliovirus VP1, the sequence of which is:
 RI-peptide: $CH_3CO$-(D)Thr-(D)Asp-(D)Lys-(D)Tyr-(D)Thr-(D)Ile-(D)Lys-(D)Trp-(D)Val-(D)Ala-(D)Phe-(D)Leu-(D)Lys-$NH_2$,
and the retro-inverso analogue of the parent L-peptide 435–446 from the third constant region of mouse heavy chain IgG2a allopeptide $\gamma 2a^b$, the sequence of which is:
 RI-peptide: $CH_3CO$-(D)Cys-(D)Ser-(D)Lys-(D)Gln-(D)Val-(D)Arg-(D)Leu-(D)Lys-(D)Ser-(D)Tyr-(D)Met-(D)Phe-(D)Tyr-$NH_2$, have been analyzed for their antigenic and in vivo immunogenic properties in the MHCII and Th cell response context (Mézière et al., In Vivo T Helper Cell Response to Retro-Inverso peptidomimetics, The journal of Immunology, 1997, 159: 3230–3237).

In a competition assay performed in vitro using reference hybridomas of known MHC class II restriction, both retro-inverso analogues bound (although more weakly in our test) to $I-A^d$ and/or $I-E^d$ class II molecules. However, in both cases, this lower affinity was apparently largely compensated in vivo as a T-cell response (with IL-2 secretion), equivalent to that obtained with the wild-type peptides, was observed following immunisation of BALB/c mice with the retro-inverso analogues. Moreover, these T-cells proliferated and produced IL-2 in response to the cognate peptides. It is concluded that the T-cell receptors of T-cells primed in vivo with the retro-inverso analogues readily cross-react with parent and retro-inverso analogue-MHC complexes.

1. Materials and Methods 1.1 Synthetic Peptides.

In the two series of peptides (L-peptide and RI-peptide 435–446 of the $\gamma 2a^b$ allotype, and L-peptide and RI-peptide 103–115 of poliovirus type 1 VP1) the $NH_2$— and —COOH termini of the parent and retro-inverso peptides were acetylated and carboxamidated, respectively. These blocked peptides were assembled in Fmoc chemistry on a Fmoc-2,4-dimethoxy-4'-(carboxymethyloxy)-benzhydrylamine resin. With respect to the parent peptide sequences, the retro-inverso peptides were assembled in a reverse order of amino acids with Fmoc-D-amino acid derivatives. In the poliovirus retro-inverso peptide, D-allo-Ile was introduced instead of D-Ile. Assembly of the protected peptide chains was carried out on a 50 μmol scale according to a classical Fmoc protocol on a multichannel peptide synthesizer (Neimark, J. and J.-P. Briand. 1993. Development of a fully automated multichannel peptide synthesizer with integrated TFA cleavable capability. *Peptide Res.* 6: 219). Retro-inverso analogues were assembled using a semi-automatic mode. An additional cysteine residue has been added at the C-terminus of $\gamma 2a^b$ peptides for coupling purposes. Peptide resins were cleaved with reagent K (King, D., C. Fields, and G. Fields. 1990. A cleavage method which minimizes side reactions following Fmoc solid-phase peptide synthesis. *Int. J. Pept. Protein Res.* 36: 255.) for 2 h, and each peptide was collected in a tube filled with cold t-butyl methyl ether. After centrifugation, pellets were washed twice with cold ether. After the last centrifugation, each peptide was dissolved in an aqueous solution and lyophilized. The crude peptides were finally purified on an Aquapore C18 ODS column (100×10 mm) using a preparative HPLC apparatus (Perkin Elmer, St. Quentin en Yvelines, France). The identity of the purified peptides was finally assessed by matrix assisted laser desorption ionization mass spectrometry using a Protein TOF™ apparatus (Bruker Spectrospin, Bremen, Germany). To induce anti-peptide antibodies, L- and retro-inverso $\gamma 2a^b$ peptides were conjugated to ovalbumin using as coupling agent Imject® maleimide activated ovalbumin from Pierce (Rockford, Il; final molar ratio: 10 peptides/ovalbumin). The peptide 12–26 (LEDARRLKAIYEKKK) of bacteriophage λ repressor (cI) was synthesized and purified using standard procedures as described above.

1.2 Immunization of Mice.

Female BALB/c mice (H-2d), 8 week-old, were purchased from IFFA Credo (St. Germain-sur-L'Arbresle, France). Anti-peptide antisera were raised by immunizing BALB/c mice with $\gamma 2a^b$ peptides coupled to ovalbumin and with poliovirus peptides mixed with methylated BSA (Calbiochem, La Jolla, Calif.; ratio: 100 μg peptide/ 1 mg mBSA). For each peptide, two mice were injected intraperitoneally with 100 μg peptide/mouse/injection. Mice received three injections at days 0, 15 and 30; the first one was given in the presence of complete Freund's adjuvant (CFA; Difco, West Molesey, UK) and the subsequent ones were in the presence of incomplete Freund's adjuvant (Difco). Mice were bled at days 20, 35 and then every two weeks until day 80. A last bleeding was done at day 115. Each mouse was bled before the beginning of immunization and the sera were used as control in each ELISA.

To test the ability of peptides to elicit a $CD4^+$ T-cell response, BALB/c mice (2 or 3 animals per peptide and per experiment) were immunized subcutaneously at the base of the tail and hind footpads with 100 μg of unconjugated peptide diluted in $H_2O$ and mixed (v/v) with CFA. Ten days later, inguinal, popliteal and periaortic lymph nodes were removed and the proliferation assay was performed using the unfractionated lymph node cell population.

1.3 Enzyme-Linked Immunosorbent Assay (ELISA).

The ELISA procedures were performed as described previously (Benkirane, N., M. Friede, G. Guichard, J.-P. Briand, M. H. V. Van Regenmortel, and S. Muller. 1993. Antigenicity and immunogenicity of modified synthetic peptides containing D-amino acid residues. *J. Biol. Chem.* 268: 26279).

1.4 Lymph Node Cell Proliferation Assays.

Peptide-induced proliferation assay of primed lymph node cells was performed using standard methods (Corradin, G., H.-M. Etlinger, and J. M. Chiller. 1977. Lymphocyte specificity to protein antigens. I. Characterization of the antigen-induced in vitro T cell-dependent proliferative response with lymph node cells from primed mice. *J.*

*Immunol.* 119: 1048.) Briefly, the inguinal, popliteal and periaortic lymph nodes removed 10 days after immunization of mice were washed in L-alanyl-L-glutamine enriched RPMI 1640-Glutamax I (Gibco, Cergy-Pontoise, France) containing 10% foetal calf serum (DAP, Vogelgrun, France), 10 μg/ml gentamycine (Gibco), 10 mM HEPES (Gibco) and β-mercaptoethanol ($5 \times 10^{-5}$ M). Cells were then resuspended at a concentration of $1 \times 10^7$ cells/ml in the same culture medium and 100 μl of this suspension were added to microtiter wells (96-well flat bottom culture plates; Costar, Cambridge, Mass.) containing 100 μl of medium containing different concentrations of immunizing (homologous) or heterologous peptides (0.03–100 μg/ml). Each concentration was tested in triplicate and tests were repeated 2–4 times. The cells were cultured at 37° C. in 5.5% $CO_2$. After 24 h, 50 μl supernatant were taken off to test the production of IL-2 and after 48 h, another aliquot of 50 μl was collected to test the production of IL-4. After 54 h, the cultures were pulsed during 18 h with tritiated thymidine (methyl [$^3$H]-thymidine, 2% ethanol, 6.7 Ci/mmole, 1 μCi/well; ICN, Orsay, France). The cells were subsequently harvested on filter with an automatic cell-harvesting device (Packard, Meriden, Conn.) and DNA-incorporated radioactivity was measured using a Matrix 9600 direct beta counter (Packard). The results are expressed as the arithmetic mean of thymidine uptake expressed as cpm. Proliferative responses were considered to be significantly positive if the [$^3$H]-thymidine uptake was equal to or above twice the uptake by lymph node cells cultured in medium alone without peptide. The SD of triplicate cultures was always below 20% of the mean. Control tests were performed by adding 100 μl/well of a 5 μg/ml hamster monoclonal antibody to mouse CD3 (Caltag, San Francisco, Calif.) and concanavalin A (Con A; 5 μg/ml; Sigma, St Louis, Mo.) to cells during the time (72 h) of the culture.

1.5 IL-2 and IL-4 Assays.

Secretion of IL-2 by activated T-helper cells was assayed by addying 50 μl culture supernatants to $1 \times 10^4$ IL-2-dependent CTL-L cells (provided by D. Raulet) during 24 h. The cells were harvested after an additional 6-h incubation in the presence of 1 μCi/well tritiated thymidine. All experiments (in triplicate) were repeated two to four times. A standard curve performed with known concentrations of recombinant IL-2 (0—30 U/ml; PharMingen, San Diego, Calif.) was used as internal control.

Secretion of IL-4 was assayed by adding culture supernatant to $1 \times 10^4$ IL-4-dependent CT4.S cells/well (Hu-Li, J., J. Ohara, C. Watson, W. Tsang, and W. E. Paul. 1989. Derivation of a T-cell line that is highly responsive to IL-4 and IL-2 (CT.4R) and of an IL-2 hyporesponsive mutant of that line (CT.4S). *J. Immunol.* 142: 800). Recombinant IL-4 used to establish the standard curve was from PharMingen. IL-4 secretion was also assayed by a double sandwich ELISA: polyvinyl microtiter plates (Falcon, Oxnard, Calif.) were coated overnight at 4° C. with 50 μl of a rat anti-mouse IL-4 (PharMingen) at 2 μg/ml in 0.05 M carbonate buffer, pH 9.6. After three washings of microtiter plates with phosphate-buffered saline containing 0.05% Tween (PBS-T), bovine serum albumin (1% w/v) in PBS-T (PBS-T-BSA) was added for 2 h at room temperature (RT). After repeated washings, 50 μl supernatant or 50 μl recombinant IL-4 (0–300 U/ml; PharMingen) used as control were added for 4h at RT. After three washings with PBS-T, 100 μl of a rat anti-mouse IL-4 conjugated to biotin (PharMingen) diluted 1/1000 in PBS-T-BSA were added for 45 min at RT. After repeated washings, positive reactions were detected by adding avidine conjugated to peroxidase (Sigma) at a 1/50 000 dilution for 30 min at RT. The final reaction was visualized by incubation with 3, 3', 5, 5'-tetramethylbenzidine in the presence of $H_2O_2$. The resulting absorbance was measured at 450 nm.

1.6 Binding of Peptide Analogues to I-$A^d$ and I-$E^d$ Class II Molecules.

The MHC class II I-$A^d$ and I-$E^d$ restriction elements involved in the presentation of peptide analogues were determined by measuring the capacity of analogues to compete with the cI peptide 12–26 for binding to I-$A^d$ or I-$E^d$ restricted antigen presenting cells (APC) (Guillet, J.-G., M.-Z. Lai, T. J. Briner, S. Buus, A. Sette, H. M. Grey, J. A. Smith, and M. L. Gefter. 1987. Immunological self, nonself discrimination. Science 235: 865). Mouse L fibroblasts transfected by either I-$A^d$ (RT 2.3.3 H) or I-$E^d$ (RT 10.3H2; $5 \times 10^4$ cells/well), provided by R. Germain (Bethesda, Md.), were incubated with various concentrations (0–100 μg/ml; 50 μl/well) of peptide. After 15–30 min at 37° C., 50 μl peptide 12–26 of cI (0.3 or 1 μg/ml) and 50 μl T-cell hybridomas B26.1 or B26.2 were added ($5 \times 10^4$ cells/well). Hybridomas B26.1 and B26.2 are derived from BALB/c mice immunized with the cI peptide 12–26 and recognize this peptide in the I-$E^d$ and I-$A^d$ context, respectively (Frandji P., C. Oskéritzian, F. Cacaraci, J. Lapeyre, R. Peronet, B. David, J.-G. Guillet, and S. Mécheri. 1993. Antigen-dependent stimulation by bone marrow-derived mast cells of MHC class II-restricted T cell hybridoma *J. Immunol.* 151, 6318.) After 24 h in culture, 50 μl aliquots of medium were removed from each well, and tested for their content in IL-2 as described above.

1.7 T Cell Antagonism Proliferation Assay.

T cell antagonism was detected in a prepulsed proliferation assay as described by De Magistris et al. and Karin et al. (Karin, N., D. J. Mitchell, S. Brocke, N. Ling, and L. Steinman. 1994. Reversal of experimental autoimmune encephalomyelitis by a soluble peptide variant of a myelin basic protein epitope: T-cell receptor antagonism and reduction of interferon γ and tumor necrosis factor α production. *J. Exp. Med.* 180: 2227; De Magistris, M. T., J. Alexander, M. Coggeshall, A. Altman, F. C. A. Gaeta, H. M. Grey, and A. Sette. 1992. Antigen analog-major histocompatibility complexes act as antagonists of the T-cell receptor. *Cell* 68: 625) with some modifications. Lymph node cells ($1 \times 10^7$/ml; used as a source of APCs) from mice immunized with either the parent peptides or the peptide analogues were first pulsed with 100 μg/ml homologous peptides for 15 min at 25° C., washed with culture medium and then incubated with four concentrations (3, 10, 30 and 100 μg/ml) of respective heterologous peptides for 15 min at 25° C. The cells were subsequently washed and treated with mitomycin C for 20 min at 25° C. Cultures were finally incubated with respective lymph node cells ($1 \times 10^7$/ml; used as responder T-cells) at 37° C., and IL-2 secretion (24 h incubation) and [$^3$H]-thymidine uptake (72 h incubation) were determined.

2. Results 2.1 Binding of Parent and Retro-Inverso Peptides to Class II MHC Molecules.

Peptide 103–115 of poliovirus VP1 contains an immunodominant I-$E^d$-restricted T-cell epitope (Leclerc, C., E. Deriaud, V. Mimic, and S. Van der Werf. 1991. Identification of a T-cell epitope adjacent to neutralization antigenic site 1 of poliovirus type 1. *J. Virol.* 65: 711) and peptide 435–451 of γ$2a^b$ encompasses a T-cell epitope containing an I-$A^d$ allele-specific motif. We have examined the consequences of introducing retro-inverso modification in parent peptides on the ability of peptide analogues to bind I-$A^d$ and I-$E^d$ molecules. This was tested by using mouse L-fibroblasts transfected with I-$A^d$ and I-$E^d$ molecules as APCs, and T-cell hybridomas B26.2 and B26.1 recognizing cI peptide 12–26 in the context of I-$A^d$ and I-$E^d$, respectively. APCs were first incubated with various concentrations of $\gamma 2a^b$ and polio peptides for 15–30 min and then co-incubated with cI peptide 12–26 and T-hybridomas for an additional 24 h. As shown in FIG. 18A, preincubation of fibroblasts transfected by I-$A^d$ with L-peptide 435–446 $\gamma 2a^b$ reduced the IL-2 production level by >88%, indicating that, as previously described (Bartnes, K., Ø. Rekdal, J.-P. Briand, and K. Hannestad. 1993. Th1 clones that suppress IgG2$a^b$ specifically recognize an allopeptide determinant comprising residues 435–451 of $\gamma 2a^b$. Eur. J. Immunol. 23: 2655), the $\gamma 2a^b$ L-peptide binds to I-$A^d$ molecules. In this test, the retro-inverso analogue 435–446 of $\gamma 2a^b$ was significantly less efficient since almost no inhibition was observed when up to 30 µg analogue were used. Preincubation of I-$A^d$ transfected fibroblasts with 100 µg retro-inverso analogue was necessary to reduce the IL-2 production by about 35%. L- and retro-inverso peptides 435–446 of $\gamma 2a^b$ were also able to interact with I-$E^d$ transfected fibroblasts (FIG. 18B). Compared to I-$A^d$, the binding of both peptides to I-$E^d$ appeared even stronger. Up to 84% and 48% inhibition with 100 µg/ml of L- and retro-inverso peptides were obtained respectively.

FIG. 18D shows that both L- and retro-inverso peptides 103–115 of poliovirus VP1 hampered the binding of cI 12–26 to I-$E^d$ transfected fibroblasts (up to 77% inhibition with 100 µg/ml of L-peptide and up to 56% inhibition with 100 µg/ml of retro-inverso peptide). Neither the L- nor the retro-inverso peptides bound to I-$A^d$ transfected fibroblasts (FIG. 18C).

2.2 Proliferative Responses of Peptide-Primed T-Lymphocytes.

BALB/c mice were immunized against the parent and modified peptides. As expected, the parent peptide 103–115 of poliovirus VP1 induced a proliferative T-cell response in immunized mice. Inguinal, popliteal and periaortic lymph node cells, removed ten days after in vivo priming and cultured for either 24 h (IL-2 assay) or 72 h (proliferation assay) with the same peptide, proliferated and produced significant levels of IL-2 (FIGS. 19A and 20A). In contrast, lymph node cells of these immunized mice did not proliferate in vitro when stimulated by the retro-inverso peptide 103–115. No IL-2 production was observed in these cultures (FIGS. 19B and 20A). This finding was confirmed using three I-$E^d$-restricted T-cell hybridomas specific for the L-peptide 103–115. T-cell hybridomas 45G10, 44B1 and 41C1 produced high levels of IL-2 when stimulated by the parent peptide 103–115 but did not respond to the retro-inverso analogue. In contrast, the retro-inverso peptide analogue 103–115 of polio VP1 was found to be immunogenic since it induced, in draining lymph nodes, T-lymphocytes which proliferated in response to the homologous peptide (FIGS. 19 and 20B). Interestingly, a good proliferative response and IL-2 production were also found when the L-peptide was added to these cell cultures.

Cross-reactivity was also observed in BALB/c mice immunized with the peptides 435–446 of $\gamma 2a^b$. The parent peptide induced a proliferative T-cell response which was stimulated both by the homologous and heterologous peptides (FIG. 19A). IL-2 production by these cells was however only observed after stimulation by the parent peptide (FIG. 19B). No IL-2 production was observed after stimulation with the retro-inverso analogue tested over a period of 4 to 48 h (not shown). In mice immunized with the retro-inverso analogue, proliferation of lymph node cells and IL-2 production were observed both after stimulation with the L- or retro-inverso peptides.

IL-4 secretion was tested in these cell culture supernatants using both an ELISA test and CT4.S cells responsive to IL-4. We found no significant secretion of IL-4 in any of these cell cultures stimulated either with L- or retro-inverso peptide.

2.3 Cross-Recognition of Retro-Inverso Polio Peptide Analogue by TCR.

It has been shown above (FIG. 19) that the retro-inverso peptide 435–446 of the $\gamma 2a^b$ allotype was able to induce the proliferation of T-lymphocytes from BALB/c mice immunized against the corresponding parent peptide but failed to induce detectable IL-2 secretion. In contrast, the retro-inverso peptide 103–115 of poliovirus VP1 did not induce significant proliferation or IL-2 production by cells from mice immunized against the parent peptide (FIGS. 19 and 20). The unresponsiveness of lymph node T-cells to the retro-inverso peptides was not due to induction of cell death, as these cells were viable after the rest period and showed a good proliferation in response to Con A or anti-CD3 antibodies (FIG. 19). In addition, T-cells from these mice could be stimulated by the respective L-peptides, whereas retro-inverso peptides could stimulate T-cells from mice immunized against the respective retro-inverso peptides.

It has been thus tested whether the retro-inverso peptide 103–115 of poliovirus VP1 could function as antagonist ligand for TCR. T-cell antagonism was detected in a prepulsed (antigen prior to the addition of the competitor) proliferation assay as previously described. In this assay, antigen-presenting lymph node cells from mice primed with either the parent peptide or the peptide analogue were first pulsed shortly (15 min instead of 24 h) with the respective homologous peptides (suboptimal conditions). Cells were then washed and incubated for 15 min with different concentrations of respective heterologous peptides ranging from 3 to 100 μg/ml. The cells were subsequently washed and the mixtures were treated for 20 min with mitomycin C. Cultures were finally incubated with respective lymph node cells used as responder T-cells. Cell responsiveness was determined in a proliferative assay and by measuring IL-2 secretion with CTL-L cells. In this test, if the T-cell response against the parent peptide is antagonized by a particular analogue, then the initial levels of proliferation and IL-2 production are significantly reduced in a peptide dose-dependent manner. Conversely, a further increase of the initial proliferative response is elicited by agonist peptides. As shown in FIG. 21A, the IL-2 secretion by T-cells from mice immunized against the L-peptide 103–115 remains unchanged in the absence or presence of the retro-inverso polio peptide (a third possibility) suggesting that the retro-inverso analogue is not recognized by TCRs of T-cells primed with the L-peptide 103–115. In contrast, the IL-2 production by T-cells primed with the retro-inverso analogue 103–115 was significantly increased in response to incubation of prepulsed T-cells with the L-peptide 103–115 (FIG. 21B).

2.4 Induction of Antibodies to L- and Retro-Inverso Peptides 435–446 of $\gamma 2a^b$ and 103–115 of Poliovirus VP1.

Groups of two BALB/c mice were immunized against the L- and retro-inverso peptides 435–446 of $\gamma 2a^b$ conjugated to ovalbumin through the free SH group of peptides, and the L- and retro-inverso peptides 103–115 of poliovirus VP1 mixed to methylated BSA. The production and cross-reactivity of antibodies to the four peptides were measured in a direct ELISA format in which the unconjugated peptides were passively adsorbed on plastic (FIG. 22). In general after two injections, a good IgG response was already found against the four peptides. Antibodies raised against the γ2a$^b$ L-peptide showed no cross-reaction in ELISA with the corresponding retro-inverso analogue (FIG. 22A) while antibodies raised against the poliovirus L-peptide cross-reacted, although less efficiently, with the homologous retro-inverso peptide (FIG. 22C). In contrast, antibodies induced against the retro-inverso analogues cross-reacted equally well and even significantly better with the parent, wild-type peptides (FIGS. 22, B and D).

What is claimed is:

1. A vaccine comprising an immunoretroid form of an immunologically active peptide, said immunoretroid being a derivative of said peptide which binds to an antibody or an antibody fragment to said peptide with at least an equal affinity as said peptide; wherein said immunoretroid form is a retro-inverso peptide or a retro-peptide of a peptide, wherein said immunoretroid form of said peptide has the following formula II:

$$A—CH(R_i)—NH—[CO—CH(R_k)—NH]_{j-i}—CO—CH(R_{j+1})—B \quad (II)$$

wherein
n, which is the number of aminoacyl residues in formula II, is 20, and $R_i$, $R_k$, and $R_{j+1}$ are side chains of the aminoacyl residues,
i, j and k are whole numbers
wherein $1 \leq i \leq j < n$, and
if i=j, k=0; and
if i<j, $i+1 \leq k \leq j$;
such that,
where i=1 and j+1=n, A is Q and B is M;
where i=1 and j+1≠n, A is Q and B is L;
where i≠1 and j+1=n, A is T and B is M; and
where i≠1 and j+1≠n, A is T and B is L;
Q being selected from the group consisting of H—, H₂N—, P—HN—, RR'N—, H₂NCO—, RR'NCO—, RCO—;
M being selected from the group consisting of H—, —COOH, —COOR, —CONH₂, —CONRR' and —NHCOR;
L being —CO—NH—CH($R_{j+2}$)—CO— ... —NH—CH ($R_n$)—CO—Y
wherein Y is selected from the group consisting of —OH, —OR, —NH₂, and —NRR'; and
T being X—HN—CH($R_1$)—CO— ... —NH—CH($R_{i-1}$)—CO—NH—
wherein X is selected from the group consisting of H—, P—, R— and RCO—;
wherein
R and R' are independently selected from the group consisting of hydrogen, $C_{1-25}$ alkyl, $C_{3-25}$ allyl, $C_{6-25}$ aryl, benzyl, 2-phenyl-ethyl, methyl-fluorenyl, glycolamide and benzhydrylglycolamide; and
P is a protecting group; and
and wherein said immunoretroid form is a retro-inverso peptide or a retro-peptide of a peptide selected from the group consisting of FP peptide of serotype A12 of foot-and-mouth disease virus,
FL peptide of serotype A12 of foot-and-mouth disease virus,
SL peptide of serotype A12 of foot-and-mouth disease virus,
said vaccine further comprising a physiologically acceptable vehicle.

2. The vaccine of claim 1 wherein said immunoretroid form of said immunologically active peptide is bound to a liposome.

3. The vaccine of claim 1 further comprising an adjuvant.

4. A vaccine of claim 1 wherein R and R' are independently selected from the group consisting of methyl, ethyl, isopropyl, tert-butyl and phenyl.

5. A vaccine of claim 1 wherein P is selected from the group consisting of tert-butyloxycarbonyl, fluorenylmethyloxycarbonyl, benzyloxycarbonyl, and allyloxycarbonyl.

6. A vaccine of claim 3 wherein R and R' are independently selected from the group consisting of methyl, ethyl, isopropyl, tert-butyl and phenyl.

7. A vaccine of claim 3 wherein P is selected from the group consisting of tert-butyloxycarbonyl, fluorenylmethyloxycarbonyl, benzyloxycarbonyl, and allyloxycarbonyl.

8. A composition comprising an immunoretroid form of a peptide selected from the group consisting of FP peptide of serotype A12 of foot-and-mouth disease virus, FL peptide of serotype A12 of foot-and-mouth disease virus, and SL peptide of serotype A12 of foot-and-mouth disease virus, said immunoretroid being a derivative of said peptide which binds to an antibody or an antibody fragment to said peptide with at least an equal affinity as said peptide; wherein said immunoretroid form is a retro-inverso peptide or a retro-peptide of a peptide, wherein said immunoretroid form of said peptide has the following formula II:

$$A—CH(R_i)—NH—[CO—CH(R_k)—NH]_{j-i}—CO—CH(R_{j+1})—B \quad (II)$$

wherein
n, which is the number of aminoacyl residues in formula II, is 20, and $R_i$, $R_k$, and $R_{j+1}$ are side chains of the aminoacyl residues,
i, j and k are whole numbers
wherein
$1 \leq i \leq j < n$, and
if i=j, k=0; and
if i<j, $i+1 \leq k \leq j$;

such that,
where i=1 and j+1=n, A is Q and B is M;
where i=1 and j+1≠n, A is Q and B is L;
where i≠1 and j+1=n, A is T and B is M; and
where i≠1 and j+1≠n, A is T and B is L;
Q being selected from the group consisting of H—, H$_2$N—, P—HN—, RR'N—, H$_2$NCO—, RR'NCO—, RCO—;
M being selected from the group consisting of H—, —COOH, —COOR, —CONH$_2$, —CONRR' and —NHCOR;
L being —CO—NH—CH(R$_{j+2}$)—CO— ... —NH—CH(R$_n$)—CO—Y wherein Y is selected from the group consisting of —OH, —OR, —NH$_2$, and —NRR'; and
T being X—HN—CH(R$_1$)—CO— ... —NH—CH(R$_{i-1}$)CO—NH— wherein X is selected from the group consisting of H—, P—, R— and RCO—;
wherein
R and R' are independently selected from the group consisting of hydrogen, C$_{1-25}$ alkyl, C$_{3-25}$ allyl, C$_{6-25}$ aryl, benzyl, 2-phenyl-ethyl, methyl-fluorenyl, glycolamide and benzhydrylglycolamide; and
P is a protecting group;
said composition further comprising a diluent.

9. A composition comprising an immunoretroid form of a peptide selected from the group consisting of FP peptide of serotype A12 of foot-and-mouth disease virus, FL peptide of serotype A12 of foot-and-mouth disease virus, and SL peptide of serotype A12 of foot-and-mouth disease virus, said immunoretroid being a derivative of said peptide which binds to an antibody or an antibody fragment to said peptide with at least an equal affinity as said peptide; wherein said immunoretroid form is a retro-inverso peptide or a retro-peptide of a peptide, wherein said immunoretroid form of said peptide has the following formula II:

$$A—CH(R_i)—NH—[CO—CH(R_k)—NH]_{j-i}—CO—CH(R_j+1)—B \quad (II)$$

wherein
n is 20,
i is a whole number in the range of 1–19,
j is a whole number in the range of 1–19,
k is 0 or whole number in the range of 2–19,
and R$_i$, R$_k$, and R$_{j+1}$ are side chains of the aminoacyl residues of said SEQ ID NO:7, SEQ ID NO:8 or SEQ ID NO:9,
wherein
$1 \leq i \leq j < n$, and
if i=j, k=0; and
if i<j, $i+1 \leq k \leq j$;
such that,
where i=1 and j+1=n, A is Q and B is M;
where i=1 and j+1≠n, A is Q and B is L;
where i≠1 and j+1=n, A is T and B is M; and
where i≠1 and j+1≠n, A is T and B is L;
Q being selected from the group consisting of H—, H$_2$N—, P—HN—, RR'N—, H$_2$NCO—, RR'NCO—, RCO—;
M being selected from the group consisting of H—, —COOH, —COOR, —CONH$_2$, —CONRR' and —NHCOR;
L being —CO—NH—CH(R$_{j+2}$)—CO— ... —NH—CH(R$_n$)—CO—Y wherein Y is selected from the group consisting of —OH, —OR, —NH$_2$, and —NRR'; and
T being X—HN—CH(R$_1$)—CO— ... —NH—CH(R$_{i-1}$)CO—NH— wherein X is selected from the group consisting of H—, P—, R— and RCO—;
wherein
R$_1$ is CH$_2$SH, R$_2$ is H, R$_3$ is CH$_2$OH, R$_4$ is H, R$_5$ is CH(CH$_3$)$_2$, R$_6$ is (CH$_2$)$_3$NHC(NH)NH$_2$, R$_7$ is H, R$_8$ is CH$_2$COOH, R$_9$ is CH$_2$(C$_6$H$_5$) or CH$_2$OH, R$_{10}$ is H, R$_{11}$ is CH$_2$OH, R$_{12}$ is CH$_2$CH(CH$_3$)$_2$, R$_{13}$ is CH$_3$, R$_{14}$ is C$_3$H$_6$ or CH$_2$CH(CH$_3$)$_2$, R$_{15}$ is (CH$_2$)$_3$NHC(NH)NH$_2$, R$_{16}$ is CH(CH$_3$)$_2$, R$_{17}$ is CH$_3$, R$_{18}$ is (CH$_2$)$_3$NHC(NH)NH$_2$, R$_{19}$ is CH$_2$CH$_2$C(O)NH$_2$ and R$_{20}$ is CH$_2$CH(CH$_3$)$_2$,
R and R' are independently selected from the group consisting of hydrogen, C$_{1-25}$ alkyl, C$_{3-25}$ allyl, C$_{6-25}$ aryl, benzyl, 2-phenyl-ethyl, methyl-fluorenyl, glycolamide and benzhydrylglycolamide;
P is a protecting group;
said composition further comprising a diluent.

10. The composition of claim 8 or claim 9 wherein said immunoretroid form of said immunologically active peptide is bound to a liposome.

11. The composition of claim 8 or claim 9 further comprising an adjuvant.

12. The composition of claim 8 or claim 9 wherein R and R' are independently selected from the group consisting of methyl, ethyl, isopropyl, tert-butyl and phenyl.

13. A composition of claim 8 or claim 9 wherein P is selected from the group consisting of tert-butyloxycarbonyl, fluorenylmethyloxycarbonyl, benzyloxycarbonyl, and allyloxycarbonyl.

14. The composition of claim 11 wherein R and R' are independently selected from the group consisting of methyl, ethyl, isopropyl, tert-butyl and phenyl.

* * * * *